US012806269B2

(12) United States Patent
Zang

(10) Patent No.: US 12,806,269 B2
(45) Date of Patent: Nov. 24, 2026

(54) CHIMERIC ANTIGEN RECEPTORS TARGETING B7-H3 (CD276) AND ASSOCIATED METHODS

(71) Applicant: Albert Einstein College of Medicine, Bronx, NY (US)

(72) Inventor: Xingxing Zang, New York, NY (US)

(73) Assignee: Albert Einstein College of Medicine, Bronx, NY (US)

(*) Notice: Subject to any disclaimer, the term of this patent is extended or adjusted under 35 U.S.C. 154(b) by 1109 days.

(21) Appl. No.: 17/757,249

(22) PCT Filed: Dec. 18, 2020

(86) PCT No.: PCT/US2020/066002
§ 371 (c)(1),
(2) Date: Jun. 13, 2022

(87) PCT Pub. No.: WO2021/127428
PCT Pub. Date: Jun. 24, 2021

(65) Prior Publication Data

US 2025/0320269 A1 Oct. 16, 2025

Related U.S. Application Data

(60) Provisional application No. 62/949,717, filed on Dec. 18, 2019.

(51) Int. Cl.

| | |
|---|---|
| ***A61K 40/31*** | (2025.01) |
| ***A61K 40/11*** | (2025.01) |
| ***A61K 40/42*** | (2025.01) |
| ***C07K 14/705*** | (2006.01) |
| ***C07K 14/71*** | (2006.01) |
| ***C07K 16/28*** | (2006.01) |

(52) U.S. Cl.

CPC .............. *A61K 40/11* (2025.01); *A61K 40/31* (2025.01); *A61K 40/421* (2025.01); *C07K 14/7051* (2013.01); *C07K 14/70517* (2013.01); *C07K 14/70521* (2013.01); *C07K 14/71* (2013.01); *C07K 16/2827* (2013.01); *A61K 2239/47* (2023.05); *C07K 2317/24* (2013.01); *C07K 2319/03* (2013.01)

(58) Field of Classification Search

None

See application file for complete search history.

(56) References Cited

U.S. PATENT DOCUMENTS 8,802,374 B2 * 8/2014 Jensen .................. A61K 40/31 530/395
2017/0355769 A1 * 12/2017 Benatuil ................ A61P 35/00

FOREIGN PATENT DOCUMENTS

| | | | |
|---|---|---|---|
| CN | 109929039 A | * | 6/2019 |
| WO | 2015/142675 | | 9/2015 |
| WO | 2017/044699 | | 3/2017 |
| WO | 2017/180813 | | 10/2017 |
| WO | 2018/023025 | | 2/2018 |

OTHER PUBLICATIONS

Rudikoff et al. Proc Natl Acad Sci. 1982. 79: 1979-1983 (Year: 1982).*
Bedouelle et al. Fees J. Jan. 2006;273(1):34-46 (Year: 2006).*
Vajdos et al. J Mol Biol. Jul. 5, 2002;320(2):415-28 (Year: 2002).*
Tang et al. Mol Ther Oncol. Sep. 2019. 14:279-287 (Year: 2019).*
Ahmed et al. J Biol Chem. Dec. 11, 2015. 290(50):30018-30029. (Year: 2015).*
English Translation of Li in CN109929039A published on Jun. 25, 2019. (Year: 2019).*
International Search Report and Written Opinion for PCT/US2020/066002, dated Mar. 22, 2021, 9 pages.
Baral et al. B7-H3 and B7-H1 expression in cerebral spinal fluid and tumor tissue correlates with the malignancy grade of glioma patients. Oncol Lett 8:1195-1201 (2014).
Brentjens et al. Genetically targeted T cells eradicate systemic acute lymphoblastic leukemia xenografts. Clin Cancer Res 13(18 Pt 1):5426-5435 (2007).
Chen et al. The coexpression and clinical significance of costimulatory molecules B7-H1, B7-H3, and B7-H4 in human pancreatic cancer. Onco Targets Ther 7:1465-1472 (2014).
Dossett et al. Adoptive immunotherapy of disseminated leukemia with TCR-transduced, CD8+ T cells expressing a known endogenous TCR. Mol Ther 17(4):742-749 (2009).
Floros & Tarhini. Anticancer Cytokines: Biology and Clinical Effects of Interferon-α2, Interleukin (IL)-2, IL-15, IL-21, and IL-12. Semin Oncol 42(4):539-548 (2015).
Guest et al. The role of extracellular spacer regions in the optimal design of chimeric immune receptors: evaluation of four different scFvs and antigens. J Immunother 28(3):203-211 (2005).
Harris & Kranz. Adoptive T Cell Therapies: A Comparison of T Cell Receptors and Chimeric Antigen Receptors. Trends Pharmacol Sci 37(3):220-230 (2016).
Hu et al. Expression of costimulatory molecule B7-H3 and its prognostic implications in human acute leukemia. Hematology 20:187-195 (2015).
Ingebrigtsen et al. B7-H3 expression in colorectal cancer: associations with clinicopathological parameters and patient outcome. BMC Cancer 14:602 (2014).
Kuball et al. Facilitating matched pairing and expression of TCR chains introduced into human T cells. Blood 109(6):2331-2338 (2007).

(Continued)

*Primary Examiner* — Anne M. Gussow

(74) *Attorney, Agent, or Firm* — Ashurst Perkins Coie US LLP

(57) ABSTRACT

In various embodiments, the present disclosure provides chimeric antigen receptors (CAR)s which bind to B7-H3. The B7-H3 CARs comprise an extracellular region comprising a binding domain that specifically binds to at least a portion of B7-H3, a transmembrane region, and an intracellular region comprising an effector domain or a portion or variant thereof and a costimulatory domain or a portion or variant thereof. Recombinant host cells expressing the CARs are also provided, as well as compositions and methods comprising the same.

18 Claims, 6 Drawing Sheets

Specification includes a Sequence Listing.

(56) References Cited

OTHER PUBLICATIONS

Leen et al. Improving T cell therapy for cancer. Annu Rev Immunol 25:243-265 (2007).
Patel et al. Impact of chimeric immune receptor extracellular protein domains on T cell function. Gene Therapy 6(3):412-419 (1999).
Picarda et al. Molecular Pathways: Targeting B7-H3 (CD276) for Human Cancer Immunotherapy. Clin Cancer Res 22:3425-3431 (2016).
Qin et al. B7-H3 is a new cancer-specific endothelial marker in clear cell renal cell carcinoma. Onco Targets Ther 6:1667-1673 (2013).
Sadelain et al. The basic principles of chimeric antigen receptor design. Cancer Discov 3(4):388-398 (2013).
Scatchard et al. The attractions of proteins for small molecules and ions. Ann. N.Y. Acad. Sci. 51:660 (1949).
Schmitt et al. T cell receptor gene therapy for cancer. Hum Gene Ther 20(11):1240-1248 (2009).
Scholten et al. Codon modification of T cell receptors allows enhanced functional expression in transgenic human T cells. Clin Immunol 119(2):135-145 (2006).
Stone et al. A novel T cell receptor single-chain signaling complex mediates antigen-specific T cell activity and tumor control. Cancer Immunol Immunother 63(11):1163-1176 (2014).
Sun et al. B7-H3 and B7-H4 expression in non-small-cell lung cancer. Lung Cancer 53:143-151 (2006).
Sun et al. B7-H3 is expressed in human hepatocellular carcinoma and is associated with tumor aggressiveness and postoperative recurrence. Cancer Immunol Immunother 61:2171-2182 (2012).
Sun et al. B7-H3 expression in breast cancer and upregulation of VEGF through gene silence. Onco Targets Ther 7:1979-1986 (2014).
Till et al. Adoptive immunotherapy for indolent non-Hodgkin lymphoma and mantle cell lymphoma using genetically modified autologous CD20-specific T cells. Blood 112(6):2261-2271 (2008).
Vigdorovich et al. Structure and T cell inhibition properties of B7 family member, B7-H3. Structure 21:707-717 (2013).
Walseng et al. A TCR-based Chimeric Antigen Receptor. Sci Rep 7(1):10713 (2017).
Wang et al. Optimizing adoptive polyclonal T cell immunotherapy of lymphomas, using a chimeric T cell receptor possessing CD28 and CD137 costimulatory domains. Hum Gene Ther 18:712-725 (2007).
Wang et al. B7-H3 associated with tumor progression and epigenetic regulatory activity in cutaneous melanoma. J Invest Dermatol 133:2050-2058 (2013).
Wang et al. B7-H3 is overexpressed in patients suffering osteosarcoma and associated with tumor aggressiveness and metastasis. PLoS One 8:e70689 (2013).
Wilson. Tech.Sight. Analyzing biomolecular interactions. Science 295(5562):2103-2105 (2002).
Wolff et al. Monoclonal antibody homodimers: enhanced antitumor activity in nude mice. Cancer Res 53(11):2560-2565 (1993).
Xylinas et al. Association of T-cell co-regulatory protein expression with clinical outcomes following radical cystectomy for urothelial carcinoma of the bladder. Eur J Surg Oncol 40:121-127 (2014).
Zang & Allison. The B7 family and cancer therapy: costimulation and coinhibition. Clin Cancer Res 13:5271-5279 (2007).
Zang et al. B7-H3 and B7x are highly expressed in human prostate cancer and associated with disease spread and poor outcome. Proc Natl Acad Sci USA 104:19458-19463 (2007).
Zang et al. Tumor associated endothelial expression of B7-H3 predicts survival in ovarian carcinomas. Mod Pathol 23:1104-1112 (2010).
Zhao et al. HHLA2 is a member of the B7 family and inhibits human CD4 and CD8 T-cell function. Proc Natl Acad Sci USA 110:9879-9884 (2013).

* cited by examiner

CHIMERIC ANTIGEN RECEPTORS TARGETING B7-H3 (CD276) AND ASSOCIATED METHODS

CROSS-REFERENCE TO RELATED APPLICATIONS

The present application 371 National Phase Application of PCT Application No. PCT/US2020/066002, entitled "CHIMERIC ANTIGEN RECEPTORS TARGETING B7-H3 (CD276) AND ASSOCIATED METHODS" filed on Dec. 18, 2020, which claims priority to U.S. Provisional Application No. 62/949,717, filed Dec. 18, 2019, which is incorporated herein by reference in its entirety, including the drawings.

STATEMENT REGARDING FEDERAL FUNDING

This invention was made with government support under CA175495 and DK100525 awarded by the National Institutes of Health. The government has certain rights in this invention.

SEQUENCE LISTING

This application contains a Sequence Listing, which was submitted in ASCII format via Patent Center, and is hereby incorporated by reference in its entirety. The ASCII copy, created on Apr. 15, 2022, is name Sequence_Listing.txt and is 72 KB in size.

BACKGROUND

Adoptive transfer of chimeric antigen receptor (CAR) modified T cells or NK cells is a potent antigen-specific therapy for treating diseases, such as human malignancies. CAR expressing T cells or NK cells target a specific antigen expressed on a malignant cell's surface. Since CAR T or NK cell-based therapeutic strategies target a specific antigen that is already expressed on a cell's surface, issues associated with tumor escape mechanisms involving major histocompatibility complexes can be overcome.

One cell surface antigen expressed by malignant cells is B7-H3 (also known as CD276), a Type I transmembrane protein that belongs to the B7 family. The extracellular portion of B7-H3 is composed of four or two immunoglobulin domains, either two variable domains and two constant domains (e.g., IgV-IgC-IgV-IgC) or one variable domain and one constant domain (e.g., IgV-IgC). The FG loop of the IgV domain(s) is involved in B7-H3-mediated T cell suppression (Vigdorovich et al., 2013).

B7-H3 is an immune checkpoint protein used by cancer cells to inhibit immune cell functions and is overexpressed in human malignancies (Picarda et al., 2006; Zang et al., 2007) including prostate cancer (Zang et al., 2007), liver cancer (Sun et al., 2012), melanoma (Wang et al., 2013), leukemia (Hu et al., 2015), breast cancer (Sun et al., 2014), ovarian cancer (Zang et al., 2010), pancreatic cancer (Chen et al., 2014), colorectal cancer (Ingebrigtsen et al., 2014), lung cancer (Sun et al., 2006), bladder cancer (Xylinas et al., 2014), renal cancer (Qin et al., 2013), brain cancer (Baral et al., 2014), osteosarcoma (Wang et al., 2013), and other cancers. High expression of B7-H3 often correlates with poor prognosis and an unfavorable clinical outcome (Picarda et al., 2006; Zang et al., 2007).

New strategies for treating human malignancies are needed, especially those involving CAR modified T cells or NK cells targeting B7-H3.

SUMMARY

In some aspects, the present disclosure provides a chimeric antigen receptor (CAR), comprising (a) an extracellular region comprising a binding domain that specifically binds to at least a portion of B7-H3, (b) a transmembrane region; and (c) an intracellular region comprising an effector domain or a portion or variant thereof and a costimulatory domain or a portion or variant thereof.

In some embodiments, the binding domain is an scFv.

In some embodiments, the scFv includes at least a $V_L$ chain of an antibody which binds to B7-H3 or a portion or variant thereof and a $V_H$ chain of an antibody which binds to B7-H3 or a portion or variant thereof. In some embodiments, the $V_L$ chain includes at least complement determining regions (CDR) 1, CDR 2, and CDR 3, and at least framework regions (FR) 1, FR 2, FR 3, and FR 4. In some embodiments, the $V_H$ chain includes at least CDR 1, CDR 2, and CDR 3, and at least FR 1, FR 2, FR 3, and FR 4. In some embodiments, the $V_L$ chain comprises an amino acid sequence having at least 75% identity to the amino acid sequences shown in SEQ ID NO: 8, 10, 12, 14, 16, or 18. In some embodiments, the $V_L$ chain comprises an amino acid sequence selected from the group consisting of SEQ ID NO: 8, 10, 12, 14, 16, or 18. In some embodiments, the $V_H$ chain comprises an amino acid sequence having at least 75% identity to the amino acid sequences shown in SEQ ID NO: 7, 9, 11, 13, 15, or 17. In some embodiments, the $V_H$ chain comprises an amino acid sequence selected from the group consisting of SEQ ID NO: 7, 9, 11, 13, 15, or 17.

In some embodiments, the extracellular region further comprises a linker or a portion or variant thereof. In some embodiments, the linker is a glycine-serine linker. In some embodiments, the glycine-serine linker comprises $Gly_xSer_y$ or about two to about ten repeats of $Gly_xSer_y$. In some embodiments, the linker is disposed between the $V_L$ and $V_H$ domains.

In some embodiments, the extracellular region further comprises a leader or a portion or variant thereof. In some embodiments, the leader is disposed N-terminal of the $V_L$ domain. In some embodiments, the leader is a $V_K$ domain of IgG1 or a portion or variant thereof.

In some embodiments, the transmembrane region comprises or is a combination of (i) a CD8α hinge or a portion or variant thereof and (ii) CD8α transmembrane region or a portion or variant thereof. In some embodiments, the transmembrane region comprises an amino acid sequence having at least 75% identity to the amino acid sequence shown in SEQ ID NO: 1.

In some embodiments, the effector domain or portion or variant thereof is CD3ζ or a portion or variant thereof. In some embodiments, the effector domain comprises an amino acid sequence having at least 75% identity to the amino acid sequence shown in SEQ ID NO: 4.

In some embodiments, the costimulatory domain or portion or variant thereof is a CD28 costimulatory domain or a portion or variant thereof, a 4-1 BB costimulatory domain or a portion or variant thereof, or a combination thereof. In some embodiments, the CD28 costimulatory domain comprises an amino acid sequence having at least 75% identity to the amino acid sequence shown in SEQ ID NO: 2. In some embodiments, the 4-1BB costimulatory domain comprises an amino acid sequence having at least 75% identity to the amino acid sequence shown in SEQ ID NO: 3. In some embodiments, the costimulatory domain comprises a CD28 costimulatory domain or a portion or variant thereof and the effector domain comprises CD3ζ or a portion or variant thereof. In some embodiments, the costimulatory domain comprises an amino acid sequence having at least 75% identity to the amino acid sequence shown in SEQ ID NO: 2 and the effector domain comprises an amino acid sequence having at least 75% identity to the amino acid sequence shown in SEQ ID NO: 4. In some embodiments, the costimulatory domain comprises a 4-1 BB costimulatory domain or a portion or variant thereof and the effector domain comprises CD3ζ or a portion or variant thereof. In some embodiments, the costimulatory domain comprises an amino acid sequence having at least 75% identity to the amino acid sequence shown in SEQ ID NO: 3 and the effector domain comprises an amino acid sequence having at least 75% identity to the amino acid sequence shown in SEQ ID NO: 4. In some embodiments, the costimulatory domain comprises a CD28 costimulatory domain or a portion or variant thereof and a 4-1 BB costimulatory domain or a portion or variant thereof, and the effector domain comprises CD3ζ or a portion or variant thereof. In some embodiments, the costimulatory domain comprises an amino acid sequence having at least 75% identity to the amino acid sequence shown in SEQ ID NO: 2 and an amino acid sequence having at least 75% identity to the amino acid sequence shown in SEQ ID NO: 3, and the effector domain comprises an amino acid sequence having at least 75% identity to the amino acid sequence shown in SEQ ID NO: 4.

In some embodiments, the binding domain is chimeric, human, or humanized.

In some aspects, the present disclosure provides an isolated polynucleotide, encoding any of the CARs described herein.

In some aspects, the present disclosure provides an expression vector, comprising any of the isolated polynucleotides described herein operably linked to an expression control sequence. In some embodiments, the expression control sequence is a promoter.

In some embodiments, the expression vector further comprises an isolated polynucleotide encoding a self-cleaving peptide. In some embodiments, the self-cleaving peptide is a 2A self-cleaving peptide. In some embodiments, the 2A self-cleaving peptide is a P2A peptide. In some embodiments, the isolated polynucleotide encoding the self-cleaving peptide is 3' of the polynucleotide encoding the CAR. In some embodiments, the isolated polynucleotide encoding the self-cleaving peptide is 5' of the isolated polynucleotide encoding the marker polypeptide.

In some embodiments, the expression vector further comprises an isolated polynucleotide encoding a transduction marker polypeptide. In some embodiments, the transduction marker polypeptide is a truncated form of epidermal growth factor receptor (EGFRt) or a portion or variant thereof or GFP or a portion or variant thereof. In some embodiments, the EGFRt or a portion or variant thereof comprises an amino acid sequence having at least 75% identity to the amino acid sequence shown in SEQ ID NO: 6.

In some embodiments, the expression vector is capable of delivering the isolated polynucleotides to a host cell.

In some embodiments, the vector is a viral vector.

In some aspects, the present disclosure provides a host cell expressing any of the CARs of the present disclosure, and/or comprising any of the isolated polynucleotides of the present disclosure, and/or comprising the expression vector of the present disclosure.

In some embodiments, the host cell is a T cell, a natural killer (NK) cell, a γδT cell, an NKT cell, a B cell, a macrophage, a dendritic cell, or an innate lymphoid cell. In some embodiments, the T cell is a CD4+ T cell, a CD8+ T cell, a $CD4^-$ $CD8^-$ double negative T cell, a γδT cell, an NKT cell, or any combination thereof. In some embodiments, the T cell is a naïve T cell, a central memory T cell, a stem cell memory T cell, an effector memory T cell, a γδT cell, an NKT cell, or any combination thereof.

In some embodiments, the host cell further expresses a transduction marker at its cell surface. In some embodiments, the transduction marker is a truncated form of epidermal growth factor receptor (EGFRt) or a portion or variant thereof or GFP or a portion or variant thereof. In some embodiments, the EGFRt or a portion or variant thereof comprises an amino acid sequence having at least 75% identity to the amino acid sequence shown in SEQ ID NO: 6.

In some aspects, the present disclosure provides a composition, comprising a host cell of the present disclosure and a pharmaceutically acceptable carrier, pharmaceutically acceptable excipient, and/or pharmaceutically acceptable diluent.

In some aspects, the present disclosure provides a method of treating a disease or condition in a subject, the method comprising administering to the subject an effective amount of the host cell of the present disclosure, wherein the disease or condition is diagnosed in the subject by the presence of B7-H3.

In some embodiments, the disease or condition is a malignancy. In some embodiments, the malignancy is a cancer. In some embodiments, the cancer is selected from the group consisting of prostate cancer, liver cancer, melanoma, leukemia, breast cancer, ovarian cancer, pancreatic cancer, colorectal cancer, lung cancer, bladder cancer, renal cancer, brain cancer, rectal cancer, cancer of the small intestine, cancer of the esophagus, bone cancer, skin cancer, cancer of the head or neck, uterine cancer, cancer of the anal region, stomach cancer, testicular cancer, cancer of the fallopian tubes, cancer of the endometrium, cancer of the cervix, cancer of the vagina, cancer of the vulva, cancer of the endocrine system, cancer of the thyroid gland, cancer of the parathyroid gland, cancer of the adrenal gland, sarcoma of soft tissue, cancer of the urethra, cancer of the penis, solid tumors of childhood, neoplasm of the central nervous system (CNS), primary CNS lymphoma, tumor angiogenesis, spinal axis tumor, squamous cell cancer, osteosarcoma, Kaposi's sarcoma, epidermoid cancer, environmentally induced cancers, combinations of the cancers, and metastatic lesions of the cancers. In some embodiments, the cancer comprises a solid tumor.

In some embodiments, the cancer is a human hematologic malignancy. For example, in certain embodiments the human hematologic malignancy may be selected from myeloid neoplasm, acute myeloid leukemia (AML), AML with recurrent genetic abnormalities, AML with myelodysplasia-related changes, therapy-related AML, acute leukemias of ambiguous lineage, myeloproliferative neoplasm, essential thrombocythemia, polycythemia vera, myelofibrosis (MF), primary myelofibrosis, systemic mastocytosis, myelodysplastic syndromes (MDS), myeloproliferative/myelodysplastic syndromes, chronic myeloid leukemia, chronic neutrophilic leukemia, chronic eosinophilic leukemia, myelodysplastic syndromes (MDS), refractory anemia with ringed sideroblasts, refractory cytopenia with multilineage dysplasia, refractory anemia with excess blasts (type 1), refractory anemia with excess blasts (type 2), MDS with isolated del (5q), unclassifiable MDS, myeloproliferative/myelodysplastic syndromes, chronic myelomonocytic leukemia, atypical chronic myeloid leukemia, juvenile myelomonocytic leukemia, unclassifiable myeloproliferative/myelodysplatic syndromes, lymphoid neoplasms, precursor lymphoid neoplasms, B lymphoblastic leukemia, B lymphoblastic lymphoma, T lymphoblastic leukemia, T lymphoblastic lymphoma, mature B-cell neoplasms, diffuse large B-cell lymphoma, primary central nervous system lymphoma, primary mediastinal B-cell lymphoma, Burkitt lymphoma/leukemia, follicular lymphoma, chronic lymphocytic leukemia, small lymphocytic lymphoma, B-cell prolymphocytic leukemia, lymphoplasmacytic lymphoma, Waldenström macroglobulinemia, mantle cell lymphoma, marginal zone lymphomas, post-transplant lymphoproliferative disorders, HIV-associated lymphomas, primary effusion lymphoma, intravascular large B-cell lymphoma, primary cutaneous B-cell lymphoma, hairy cell leukemia, multiple myeloma, monoclonal gammopathy of unknown significance (MGUS), smoldering multiple myeloma, or solitary plasmacytomas (solitary bone and extramedullary).

In some aspects, the present disclosure provides a method of eliciting an immune response against B7-H3 that requires binding of any of the CARs of the present disclosure to B7-H3, the method comprising administering to a subject having a disease or condition diagnosed by expression of B7-H3 an effective amount of any of the host cells of the present disclosure.

In some embodiments, methods of the present disclosure further comprise administering at least one-unit dose of any of the host cells of the present disclosure to the subject. In some embodiments, a second unit dose is administered to the subject about two, three, four, five, six, seven, eight, nine, ten, eleven, twelve, thirteen, fourteen, fifteen, sixteen or more weeks after a first unit dose is administered to the subject. In some embodiments, the at least one-unit dose, first unit dose, and/or second unit dose comprises about $10^5$ cells/$m^2$ to about $10^{11}$ cells/$m^2$, inclusive.

In some aspects, the present disclosure provides a use of any of the CARs of the present disclosure, or any of the expression vector of the present disclosure, or any of the host cells of the present disclosure, in the manufacture of a medicament for the treatment of a disease or condition diagnosed by expression of B7-H3 on at least one proliferative cell.

In some embodiments, the at least one proliferative cell is a malignant cell. In some embodiments, the malignant cell is a cancer cell.

These and other embodiments of the present disclosure will be disclosed in further detail herein below.

DETAILED DESCRIPTION

Figure 1B:
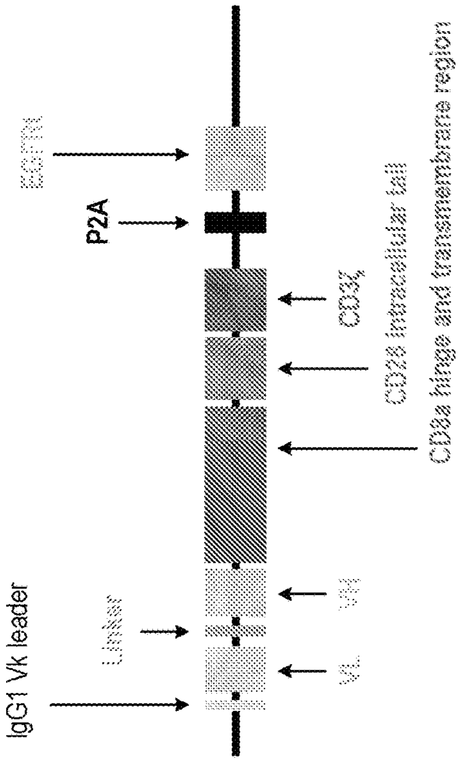
FIG. 1B is a schematic representation of a tagged variant of the B7-H3 CAR of FIG. 1A in accordance with an embodiment of the present disclosure.
Figure 1A:
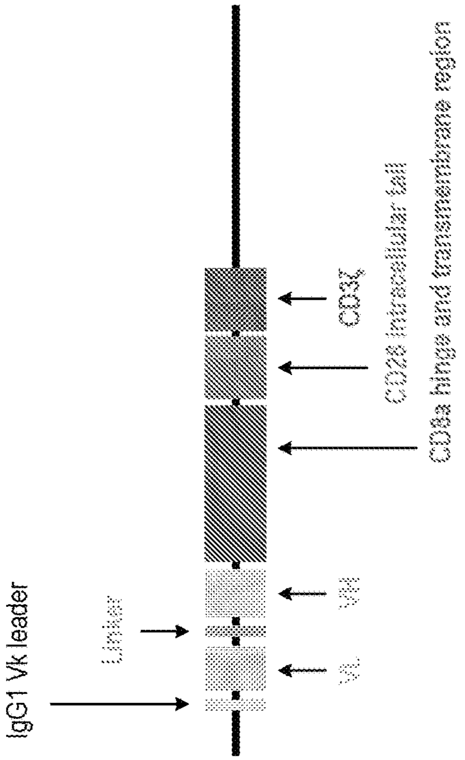
FIG. 1A is a schematic representation of a B7-H3 chimeric antigen receptor (CAR) in accordance with an embodiment of the present disclosure.
Figure 1C:
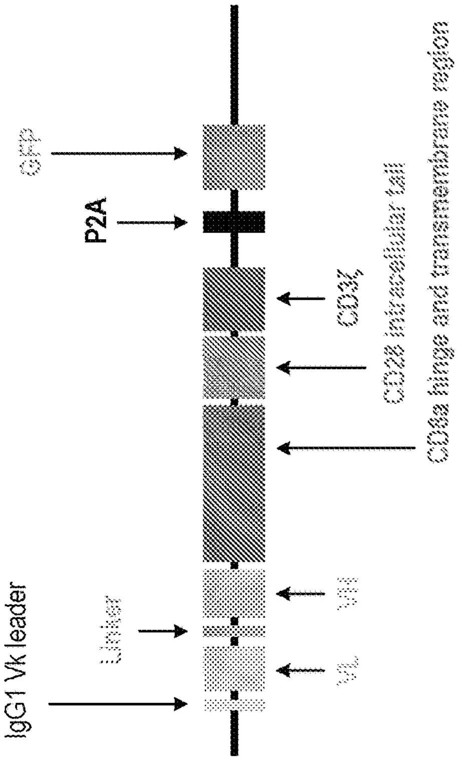
FIG. 1C is a schematic representation of another tagged variant of the B7-H3 CAR of FIG. 1A in accordance with an embodiment of the present disclosure.
Figure 2A:
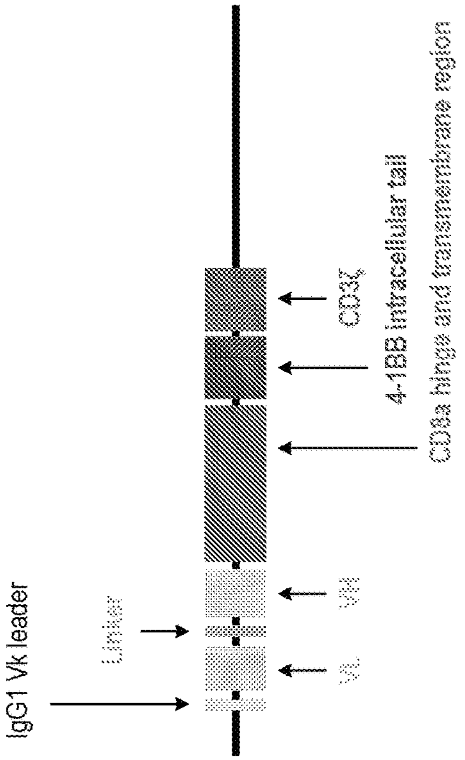
FIG. 2A is a schematic representation of another B7-H3 CAR in accordance with an embodiment of the present disclosure.
Figure 2B:
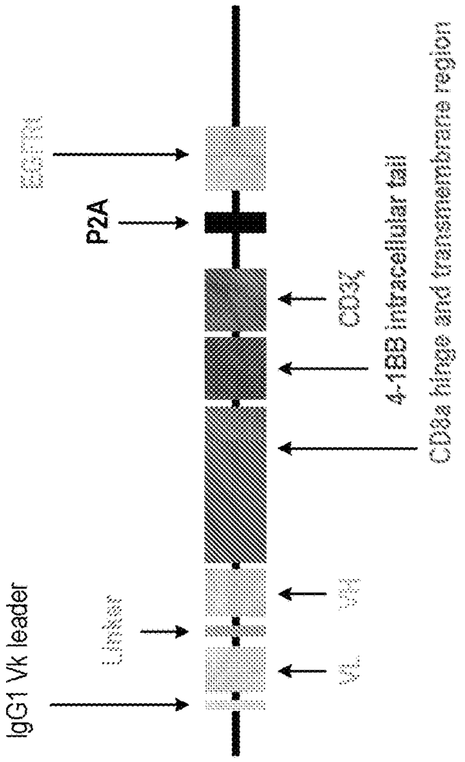
FIG. 2B is a schematic representation of a tagged variant of the B7-H3 CAR of FIG. 2A in accordance with an embodiment of the present disclosure.
Figure 2C:
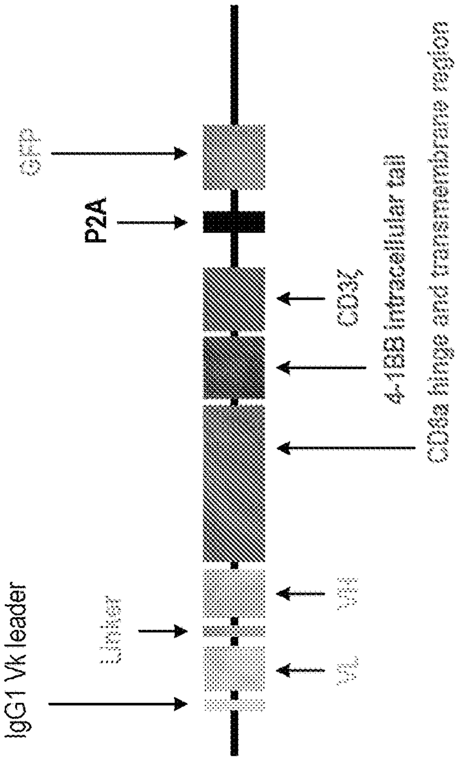
FIG. 2C is a schematic representation of another tagged variant of the B7-H3 CAR of FIG. 2A in accordance with an embodiment of the present disclosure.
Figure 3B:
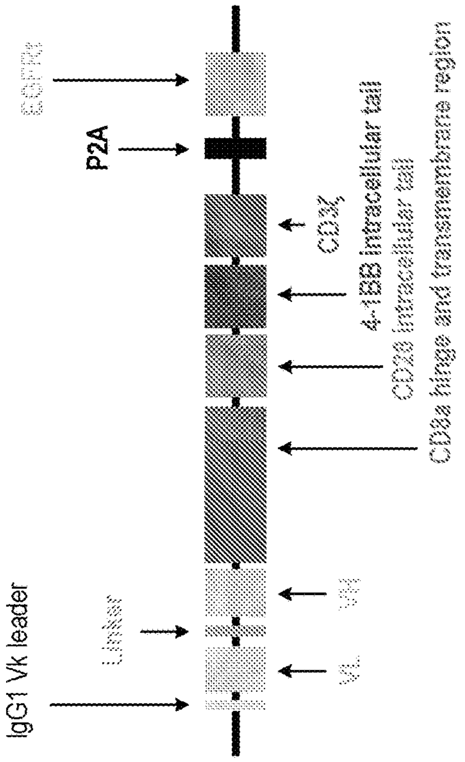
FIG. 3B is a schematic representation of a tagged variant of the B7-H3 CAR of FIG. 3A in accordance with an embodiment of the present disclosure.
Figure 3A:
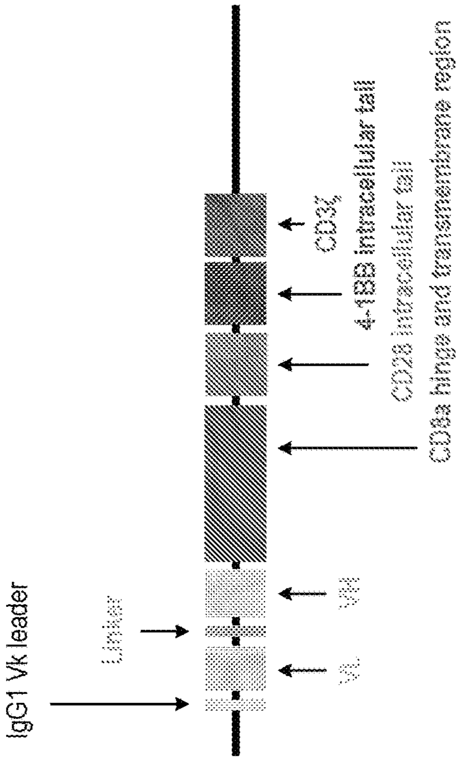
FIG. 3A is a schematic representation of yet another B7-H3 CAR in accordance with an embodiment of the present disclosure.
Figure 3C:
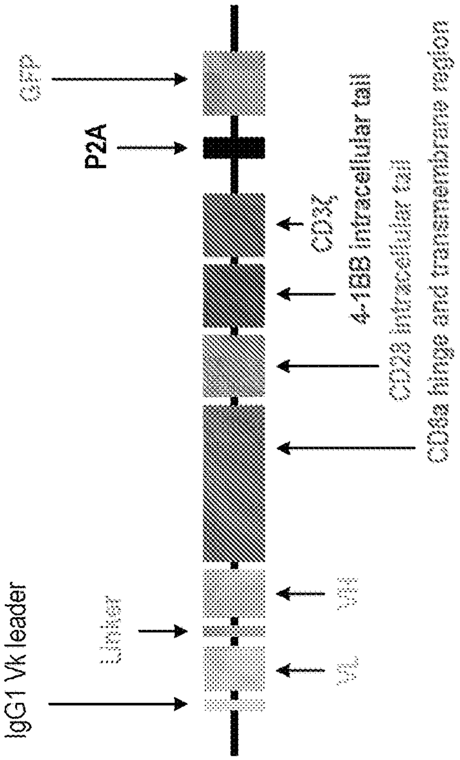
FIG. 3C is a schematic representation of another tagged variant of the B7-H3 CAR of FIG. 3A in accordance with an embodiment of the present disclosure.

The present disclosure provides chimeric antigen receptors (CARs) which bind to B7-H3, cells expressing these CARs, and methods of using these CARs and cells expressing the same.

When expressed by a cell and bound to B7-H3 expressed by a target cell, the B7-H3 CARs provided herein induce initiation, propagation, and/or magnification of a molecular signal in the cell, such as cytotoxicity, proliferation, and/or survival. Exemplary CARs of the present disclosure comprise (a) an extracellular region comprising a binding domain (e.g., an scFv) that specifically binds to B7-H3; (b) a transmembrane region; and (c) an intracellular region comprising an effector domain or a portion or variant thereof, and a costimulatory domain or a portion or variant thereof.

The B7-H3 CARs of the present disclosure are useful in cellular immunotherapies (e.g., T cells, NK cells, γδT cells, NKT cells, B cells, macrophages, dendritic cells, and innate lymphoid cells) for treating a disease or condition associated with B7-H3 expression, such as, a malignancy. In some embodiments, when administered to a subject having target cells (e.g., malignant cells) that express B7-H3, cells expressing B7-H3 CARs of the present disclosure reduce and/or suppress growth, area, volume, and/or spread of the malignant cells, eliminate (e.g., kill) malignant cells, and/or increase survival of the subject to a greater degree and/or for a longer period of time than cells that do not comprise a B7-H3 CAR of the present disclosure.

In some embodiments, a T cell, a NK cell, a γδT cell, an NKT cell, a B cell, a macrophage, a dendritic cell, or an innate lymphoid cell expressing a B7-H3 CAR described herein demonstrates increased and/or sustained cell signaling, such as cytokine production and/or release, phosphorylation of one or more proteins associated with a T cell response to antigen-binding, and/or activity, such as mobilization of intracellular calcium, cytotoxic activity, secretion of a cytokine, proliferation, and/or activation following stimulation. One or more of these effects occurring in response to B7-H3 binding is improved relative to a T cell and/or a NK cell that does not express a B7-H3 CAR of the present disclosure.

The following description of the present disclosure is merely intended to illustrate various embodiments of the present disclosure. As such, the specific modifications discussed herein are not to be construed as limitations on the scope of the present disclosure. It will be apparent to one skilled in the art that various equivalents, changes, and modifications may be made without departing from the scope of the present disclosure, and it is understood that such equivalent embodiments are to be included herein.

Reference throughout this specification to "one example," "an example," "one embodiment," "an embodiment," "one aspect," or "an aspect" means that a particular feature, structure, or characteristic described in connection with the example is included in at least one example of the present disclosure. Thus, the occurrences of the phrases "in one example," "in an example," "one embodiment," "an embodiment," "one aspect," or "an aspect" in various places throughout this specification are not necessarily all referring to the same example, embodiment, and/or aspect.

The headings provided herein are for convenience only and are not intended to limit or interpret the scope or meaning of the present disclosure.

Definitions

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein is to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated regions. Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense that one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense that one having skill in the art would understand the convention (e.g., "a system having at least one of A, B, or C" would include but not be limited to systems that have A alone, B alone, C alone, A and B together, A and C together, B and C together, and/or A, B, and C together, etc.). As used herein, the terms "include," "have," and "comprise" are used synonymously, which terms and variants thereof are intended to be construed as non-limiting.

The terms "peptide," "polypeptide," and "protein" are used interchangeably to refer to a polymer of amino acid residues, and are not limited to a minimum length, though a number of amino acid residues may be specified. Polypeptides may include amino acid residues including natural and/or non-natural amino acid residues. The terms also include post-expression modifications of the polypeptide, for example, glycosylation, sialylation, acetylation, phosphorylation, and the like. In some embodiments, the polypeptides may contain modifications with respect to a native or natural sequence, as long as the protein maintains the desired activity. These modifications may be deliberate, as through site-directed mutagenesis, or may be accidental, such as through mutations of hosts which produce the proteins or errors due to PCR amplification.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified. Amino acid analogs refer to compounds that have the same basic chemical structure as a naturally occurring amino acid. Such analogs have modified R groups or modified peptide backbones, but retain the same basic chemical structure as a naturally occurring amino acid. Amino acid mimetics refer to chemical compounds that have a structure that is different from the general chemical structure of an amino acid, but that function in a manner similar to a naturally occurring amino acid.

The term "acidic residue" refers to amino acid residues in D- or L-form having sidechains comprising acidic groups. Exemplary acidic residues include D and E.

The term "amide residue" refers to amino acids in D- or L-form having sidechains comprising amide derivatives of acidic groups. Exemplary residues include N and Q.

The term "aromatic residue" refers to amino acid residues in D- or L-form having sidechains comprising aromatic groups. Exemplary aromatic residues include F, Y, and W.

The term "basic residue" refers to amino acid residues in D- or L-form having sidechains comprising basic groups. Exemplary basic residues include H, K, and R.

The term "hydrophilic residue" refers to amino acid residues in D- or L-form having sidechains comprising polar groups. Exemplary hydrophilic residues include C, S, T, N, and Q.

The term "nonfunctional residue" refers to amino acid residues in D- or L-form having sidechains that lack acidic, basic, or aromatic groups. Exemplary nonfunctional amino acid residues include M, G, A, V, I, L and nor leucine (Nle).

The term "neutral hydrophobic residue" refers to amino acid residues in D- or L-form having sidechains that lack basic, acidic, or polar groups. Exemplary neutral hydrophobic amino acid residues include A, V, L, I, P, W, M, and F.

The term "polar hydrophobic residue" refers to amino acid residues in D- or L-form having sidechains comprising polar groups. Exemplary polar hydrophobic amino acid residues include T, G, S, Y, C, Q, and N.

The term "hydrophobic residue" refers to amino acid residues in D- or L-form having sidechains that lack basic or acidic groups. Exemplary hydrophobic amino acid residues include A, V, L, I, P, W, M, F, T, G, S, Y, C, Q, and N.

A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally, or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company. Variant proteins, peptides, polypeptides, and amino acid sequences of the present disclosure can, in certain embodiments, comprise one or more conservative substitutions relative to a reference amino acid sequence.

"Nucleic acid molecule" or "polynucleotide" refers to a polymeric compound including covalently linked nucleotides comprising natural subunits (e.g., purine or pyrimidine bases). Purine bases include adenine, and guanine, and pyrimidine bases including uracil, thymine, and cytosine. Nucleic acid molecules include polyribonucleic acid (RNA), polydeoxyribonucleic acid (DNA), which includes cDNA, genomic DNA, and synthetic DNA, either of which may be single or double-stranded. A nucleic acid molecule encoding an amino acid sequence includes all nucleotide sequences that encode the same amino acid sequence.

As used herein, the terms "homologous," "homology," or "percent homology" when used herein to describe to a nucleic acid sequence, relative to a reference sequence, can be determined using the formula described by Karlin & Altschul 1990, modified as in Karlin & Altschul 1993. Percent homology of sequences can be determined using the most recent version of BLAST, as of the filing date of this application.

"Percent (%) sequence identity" with respect to a reference polypeptide sequence is the percentage of amino acid residues in a candidate sequence that is identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are known, for instance, using publicly available computer software such as BLAST, BLAST-2, ALIGN or Megalign (DNASTAR) software, or other software appropriate for nucleic acid sequences. Appropriate parameters for aligning sequences are able to be determined, including algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a some % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

As used herein, "mutation" refers to a change in the sequence of a polynucleotide molecule or polypeptide molecule as compared to a reference or wild-type polynucleotide molecule or polypeptide molecule, respectively. A mutation can result in several different types of change in sequence, including substitution, insertion or deletion of nucleotide(s) or amino acid(s).

The term "isolated" means that the material is removed from its original environment (e.g., the natural environment if it is naturally occurring). Such nucleic acid could be part of a vector and/or such nucleic acid or polypeptide could be part of a composition (e.g., a cell lysate), and still be isolated in that such vector or composition is not part of the natural environment for the nucleic acid or polypeptide.

"Exogenous" with respect to a nucleic acid or polynucleotide indicates that the nucleic acid is part of a recombinant nucleic acid construct or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid also can be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. The exogenous elements may be added to a construct, for example, using genetic recombination. Genetic recombination is the breaking and rejoining of DNA strands to form new molecules of DNA encoding a novel set of genetic information.

A "functional variant" refers to a polypeptide or polynucleotide that is structurally similar or substantially structurally similar to a parent or reference compound of this disclosure, but differs, in some contexts slightly, in composition (e.g., one base, atom or functional group is different, added, or removed; or one or more amino acids are mutated, inserted, or deleted), such that the polypeptide or encoded polypeptide is capable of performing at least one function of the encoded parent polypeptide with at least 50% efficiency of activity of the parent polypeptide.

As used herein, a "functional portion" or "functional fragment" refers to a polypeptide or polynucleotide that comprises only a domain, motif, portion or fragment of a parent or reference compound, and the polypeptide or encoded polypeptide retains at least 50% activity associated with the domain, portion or fragment of the parent or reference compound. In certain embodiments, a functional portion refers to a "signaling portion" of an effector molecule, effector domain, costimulatory molecule, or costimulatory domain.

The term "expression," as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof. An expressed nucleic acid molecule is typically operably linked to an expression control sequence (e.g., a promoter).

The term "operably linked" refers to the association of two or more nucleic acid molecules on a single nucleic acid fragment so that the function of one is affected by the other.

As used herein, "expression vector" refers to a DNA construct containing a nucleic acid molecule that is operably linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself. Here, "plasmid," "expression plasmid," "virus" and "vector" are often used interchangeably.

The term "introduced" in the context of inserting a nucleic acid molecule into a cell, means "transfection," or "transformation" or "transduction" and includes reference to the incorporation of a nucleic acid molecule into a eukaryotic cell wherein the nucleic acid molecule may be incorporated into the genome of a cell and converted into an autonomous replicon. As used herein, the term "engineered," "recombinant" or "non-natural" refers to an organism, microorganism, cell, nucleic acid molecule, or vector that includes at least one genetic alteration or has been modified by introduction of an exogenous nucleic acid molecule, wherein such alterations or modifications are introduced by genetic engineering. Genetic alterations include, for example, modifications introducing expressible nucleic acid molecules encoding proteins, CARs or enzymes, or other nucleic acid molecule additions, deletions, substitutions or other functional disruption of a cell's genetic material.

The term "construct" refers to any polynucleotide that contains a recombinant nucleic acid molecule. A construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, an RNA vector or a linear or circular DNA or RNA molecule that may include chromosomal, non-chromosomal, semi-synthetic or synthetic nucleic acid molecules. Exemplary vectors are those capable of autonomous replication (episomal vector), capable of delivering a polynucleotide to a cell genome (e.g., viral vector), or capable of expressing nucleic acid molecules to which they are linked (expression vectors).

As used herein, the term "host" refers to a cell or microorganism targeted for genetic modification with a heterologous nucleic acid molecule to produce a polypeptide of interest. In certain embodiments, a host cell may optionally already possess or be modified to include other genetic modifications that confer desired properties related or unrelated to, biosynthesis of the heterologous protein.

As used herein, "enriched" or "depleted" with respect to amounts of cell types in a mixture refers to an increase in the number of the "enriched" type, a decrease in the number of the "depleted" cells, or both, in a mixture of cells resulting from one or more enriching or depleting processes or steps. In certain embodiments, amounts of a certain cell type in a mixture will be enriched and amounts of a different cell type will be depleted, such as enriching for $CD4^+$ cells while depleting $CD8^+$ cells, or enriching for $CD8^+$ cells while depleting $CD4^+$ cells, or combinations thereof.

"Chimeric antigen receptor" (CAR) refers to a CAR of the present disclosure engineered to contain two or more naturally occurring (or engineered) amino acid sequences linked together in a way that does not occur naturally or does not occur naturally in a host cell, which CAR can function as a receptor when present on a surface of a cell. CARs of the present disclosure include an extracellular portion comprising an antigen-binding domain, such as one obtained or derived from an immunoglobulin, such as an scFv derived from an antibody linked to a transmembrane region and one or more intracellular signaling domains (optionally containing co-stimulatory domain(s)) (see, e.g., Sadelain et al., 2013; see also Harris & Kranz, 2016; Stone et al., 2014).

The term "variable region" or "variable domain" refers to an antibody heavy or light chain, that is involved in binding to antigen. Variable domains of antibody heavy ($V_H$) and light ($V_L$) chains each generally comprise four generally conserved framework regions (FRs) and three CDRs. Framework regions separate CDRs, and CDRs are situated between framework regions.

The terms "complementarity determining region," and "CDR," are synonymous with "hypervariable region" or "HVR," and are known in the art to refer to sequences of amino acids within antibody variable regions, which, in general, confer antigen specificity and/or binding affinity and are separated from one another in primary structure by framework sequence. In some cases, framework amino acids can also contribute to binding. In general, there are three CDRs in each variable region. Variable domain sequences can be aligned to a numbering scheme (e.g., Kabat, EU, International Immunogenetics Information System (IMGT) and Aho), which can allow equivalent residue positions to be annotated and for different molecules to be compared using Antigen receptor Numbering And Receptor Classification (ANARCI) software tool (2016, Bioinformatics 15:298-300).

"Antigen" as used herein refers to an immunogenic molecule that provokes an immune response. This immune response may involve antibody production, activation of specific immunologically-competent cells, or both. An antigen may be, for example, a peptide, glycopeptide, polypeptide, glycopolypeptide, polynucleotide, polysaccharide, lipid or the like. It is readily apparent that an antigen can be synthesized, produced recombinantly, or derived from a biological sample. Exemplary biological samples that can contain one or more antigens include tissue samples, tumor samples, cells, biological fluids, or combinations thereof. Antigens can be produced by cells that have been modified or genetically engineered to express an antigen.

The term "epitope" includes any molecule, structure, amino acid sequence or protein determinant that is recognized and specifically bound by a cognate binding molecule, such as a chimeric antigen receptor, or other binding molecule, domain or protein.

A "binding domain" (also referred to as a "binding region"), as used herein, refers to a molecule or portion thereof that possesses the ability to specifically and non-covalently associate, unite, or combine with a target, such as an scFv. A binding domain includes any naturally occurring, synthetic, semi-synthetic, or recombinantly produced binding partner for a biological molecule, a molecular complex, or other target of interest. Exemplary binding domains include single chain immunoglobulin variable regions, receptor ectodomains, ligands, or synthetic polypeptides selected for their specific ability to bind to a biological molecule, a molecular complex or other target of interest.

As used herein, an "effector domain" is an intracellular portion or domain of a CAR or receptor that can directly or indirectly promote a biological or physiological response in a cell when receiving an appropriate signal. In certain embodiments, an effector domain is from a protein or portion thereof or protein complex that receives a signal when bound to a target or cognate molecule, or when the protein or portion thereof or protein complex binds directly to a target or cognate molecule and triggers a signal from the effector domain.

A "transmembrane region," as used herein, is a portion of a transmembrane protein that can insert into or span a cell membrane.

"Treat" or "treatment" or "ameliorate" refers to medical management of a disease, disorder, or condition of a subject. In general, an appropriate dose or treatment regimen comprising a host cell expressing a CAR of the present disclosure, and optionally an adjuvant, is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease; stabilization of disease state; delay of disease progression; remission; survival; prolonged survival; or any combination thereof.

As used herein, "hyperproliferative disorder" and "proliferative disorder" refer to excessive growth or proliferation as compared to a normal or undiseased cell. Exemplary hyperproliferative disorders and proliferative disorders include tumors, cancers, neoplastic tissue, carcinoma, sarcoma, malignant cells, pre malignant cells.

Furthermore, "cancer" may refer to any accelerated proliferation of cells, including solid tumors, ascites tumors, blood or lymph or other malignancies; connective tissue malignancies; metastatic disease; minimal residual disease following transplantation of organs or stem cells; multi-drug resistant cancers, primary or secondary malignancies, angiogenesis related to malignancy, or other forms of cancer.

A "therapeutically effective amount" or "effective amount" of a host cell expressing a CAR of this disclosure, refers to an amount of CAR expressing host cells sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient or a cell expressing a single active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially or simultaneously.

The term "pharmaceutically acceptable excipient or carrier" or "physiologically acceptable excipient or carrier" refer to biologically compatible vehicles, which are described in greater detail herein, that are suitable for administration to a human or other non-human mammalian subject and generally recognized as safe or not causing a serious adverse event.

As used herein, the term "adoptive immune therapy" or "adoptive immunotherapy" refers to administration of naturally occurring or genetically engineered, disease-antigen-specific immune cells, such as T cells. Adoptive cellular immunotherapy may be autologous (immune cells are from the recipient), allogeneic (immune cells are from a donor of the same species) or syngeneic (immune cells are from a donor genetically identical to the recipient).

A "T cell" or "T lymphocyte" is an immune system cell that matures in the thymus and produces T cell receptors (TCRs), including αβT cells and γδT cells. T cells can be naïve (not exposed to antigen; increased expression of CD62L, CCR7, CD28, CD3, CD127, and CD45RA, and decreased expression of CD45RO as compared to $T_{CM}$), memory T cells ($T_M$) (antigen-experienced and long-lived), and effector cells (antigen-experienced, cytotoxic). $T_M$ can be further divided into subsets of central memory T cells ($T_{CM}$, increased expression of CD62L, CCR7, CD28, CD127, CD45RO, and CD95, and decreased expression of CD54RA as compared to naïve T cells) and effector memory T cells (TEM, decreased expression of CD62L, CCR7, CD28, CD45RA, and increased expression of CD127 as compared to naïve T cells or $T_{CM}$).

A natural killer cell ("NK cells") as used herein refers to cells which are activated in response to interferons or macrophage-derived cytokines, contain viral infections while the adaptive immune response is generating antigen-specific cytotoxic T cells that can clear the infection, and express CD56.

In addition, it should be understood that the individual constructs, or groups of constructs, derived from the various combinations of the structures and subunits described herein, are disclosed by the present disclosure to the same extent as if each construct or group of constructs was set forth individually. Thus, selection of particular structures or particular subunits is within the scope of the present disclosure.

The terminology used in the description is intended to be interpreted in its broadest reasonable manner, even though it is being used in conjunction with a detailed description of identified embodiments.

Chimeric Antigen Receptors (CARs)

Aspects of the present disclosure are directed to chimeric antigen receptors (CAR) which bind to at least a portion of B7-H3 that is expressed at least partially on an extracellular surface of a cell, such as a malignant cell.

In certain aspects, the present disclosure provides CARs comprising (a) an extracellular region comprising a binding domain that specifically binds to at least a portion of B7-H3, (b) a transmembrane region, and (c) an intracellular region comprising an effector domain or a portion or variant thereof and a costimulatory domain or a portion or variant thereof.

B7-H3 binding domains disposed in the (a) extracellular regions of the present disclosure are, in some embodiments, scFvs which comprise at least a portion of an antibody $V_L$ chain, at least a portion of an antibody $V_H$ chain, and a linker domain. In some embodiments, the at least a portion of the antibody $V_L$ chain is a $V_L$ domain and the at least a portion of the $V_H$ chain is the $V_H$ domain. In some embodiments, the linker domain is a peptide linker disposed between the $V_L$ domain and the $V_H$ domain. For example, the B7-H3 scFvs may be designed so that the C-terminal end of the $V_L$ domain is linked to the N-terminal end of the $V_H$ domain by the peptide linker ((N)$V_L$(C)-linker-(N)$V_H$(C)) or such that the C-terminal end of the $V_H$ domain is linked to the N-terminal end of the $V_L$ domain by the peptide linker (N)$V_H$(C)-linker-(N)$V_L$(C). Exemplary linkers include those having a glycine-serine amino acid chain having from one to about ten repeats of $Gly_xSer_y$, wherein x and y are each independently an integer from 0 to 10, provided that x and y are not both 0 (e.g., $(Gly_4Ser)_2$; $(Gly_3Ser)_2$; $Gly_2Ser$; or a combination thereof, such as $(Gly_3Ser)_2Gly_2Ser$). Linker length may be varied to maximize B7-H3 antigen recognition based on B7-H3, the selected binding epitope of B7-H3, or B7-H3 antigen binding domain size and affinity (Guest et al., 2005; Patel et al. 1999; PCT Publ. No. WO 2014/031687.

Sources of binding domains specific for B7-H3 are known in the art, including known antibodies, methods of generating B7-H3 antibodies, and B7-H3 binding domains described herein. Exemplary binding domains specific for B7-H3 antigens, including CDRs thereof, are disclosed at SEQ ID NOs: 7-18. In certain embodiments, the B7-H3 scFV or variant thereof comprises or consists of an amino acid sequence having at least 75%, 80%, 85%, 90%, 91%, 92%, 93%, 94%, 95%, 96%, 97%, 98%, 99%, or more identity to any one of SEQ ID NOs: 7-18.

B7-H3 CARs of the present disclosure comprise one or more CDRs, such as three heavy chain CDRs and three light chain CDRs, according to any one of these exemplary binding domain SEQ ID NOs: 7-18, or can comprise a portion or a variant sequence thereof. B7-H3 binding domain affinities can be determined using a variety of known assays, such as Western blot, ELISA, analytical ultracentrifugation, spectroscopy and surface plasmon resonance (Biacore®) analysis (see, e.g., Scatchard et al. 1949; Wilson 2002; Wolff et al., 1993; and U.S. Pat. Nos. 5,283,173, 5,468,614, or the equivalent).

In some embodiments, the (a) extracellular region further comprises a leader domain, which includes but is not limited to, a leader peptide. For example, the leader peptide can be an IgG1 $V_K$ leader domain, or a portion or variant thereof bound to the N-terminal end of the $V_H$ domain or the $V_L$ domain of the B7-H3 scFv.

In some embodiments, the (c) intracellular region effector domain is from CD3ζ or a functional portion or variant thereof. An exemplary CD3ζ effector domain is disclosed at SEQ ID NO: 4. In certain embodiments, the CD3ζ effector domain portion or variant thereof comprises or consists of an amino acid sequence having at least 75%, 80%, 85%, 90%, 91%, 92%, 93%, 94%, 95%, 96%, 97%, 98%, 99%, or more identity to SEQ ID NO: 4.

In some embodiments, the (c) intracellular region costimulatory domain is an intracellular tail from CD28 or portion or variant thereof and/or from an intracellular tail from 4-1 BB or portion or variant thereof. The costimulatory domain is disposed between the CD8α transmembrane domain or portion or variant thereof and the CD3ζ effector domain portion or variant thereof. When the costimulatory domain comprises both the intracellular tail from CD28 or portion or variant thereof and the intracellular tail from 4-1 BB or portion or variant thereof, the CD28 intracellular tail or portion or variant thereof can be N-terminal or C-terminal to the 4-1BB intracellular tail or portion or variant thereof. In certain embodiments, the intracellular tail from CD28 or portion or variant thereof comprises or consists of an amino acid sequence having at least 75%, 80%, 85%, 90%, 91%, 92%, 93%, 94%, 95%, 96%, 97%, 98%, 99%, or more identity to SEQ ID NO: 2. In certain embodiments, the intracellular tail from 4-1 BB or portion or variant thereof comprises or consists of an amino acid sequence having at least 75%, 80%, 85%, 90%, 91%, 92%, 93%, 94%, 95%, 96%, 97%, 98%, 99%, or more identity to SEQ ID NO: 3.

The (a) extracellular region and the (c) intracellular region of the present disclosure are connected by the (b) transmembrane region. For example, the (b) a transmembrane region is disposed between a C-terminal end of the B7-H3 scFv and an N-terminal end of the (c) intracellular region. In certain embodiments, the transmembrane region comprises or is derived from a known transmembrane protein, such as a CD8α transmembrane region. In some embodiments, the (b) transmembrane region comprises a known hinge domain and a known transmembrane domain, such as the hinge domain and the transmembrane domain of CD8α, or a portion or variant thereof. An exemplary CD8α hinge domain and CD8α transmembrane domain are disclosed at SEQ ID NO: 1. In certain embodiments, the CD8α hinge domain and CD8α transmembrane domain portion or variant thereof comprises or consists of an amino acid sequence having at least 75%, 80%, 85%, 90%, 91%, 92%, 93%, 94%, 95%, 96%, 97%, 98%, 99%, or more identity to SEQ ID NO: 1.

Polypeptide markers are unique peptide sequences that are co-expressed in a cell, such as a host cell, along with one or more B7-H3 CARs. Unlike B7-H3 CARs of the present disclosure, polypeptide markers are recognized or bound by, for example, an antibody or detected by an emitted signal, such as fluorescence. Polypeptide markers can be useful for detecting, identifying, isolating, tracking, purifying, enriching for, targeting, or biologically or chemically modifying tagged proteins of interest, particularly when a tagged protein is part of a heterogeneous population of cell proteins or cells, such as a biological sample like peripheral blood. Exemplary polypeptide markers of the present disclosure include green fluorescent protein (GFP) and a truncated form of epidermal growth factor receptor (EGFRt). Amino acid sequences of GFP are generally known in the art and an exemplary EGFRt amino acid sequence is shown as SEQ ID NO: 6.

Table 1 below lists amino acid sequences of various 1B7-H-3 CAR components. For each mAb sequence, the leader sequence is shown italicized, the FR1-4 sequences are shown underlined, and the CDR1-3 sequences are shown in bold.

TABLE 1

B7-H3 CAR Amino Acid Sequences

| SEQ ID NO. | NAME | SEQUENCE |
|---|---|---|
| 1 | CD8α hinge and CD8α transmembrane region | TTTPAPRPPTPAPTIASQPLSLRPEACRPAAGGAVHTRGLDFACDIYIWAPLAGTCGVLLLSLVITLYC |
| 2 | CD28 intracellular tail | RSKRSRLLHSDYMNMTPRRPGPTRKHYQPYAPPRDFAAYRS |
| 3 | 4-1BB intracellular tail | KRGRKKLLYIFKQPFMRPVQTTQEEDGCSCRFPEEEEGGCEL |
| 4 | CD3ζ | RVKFSRSADAPAYQQGQNQLYNELNLGRREEYDVLDKRRGRDPEMGGKPQRRKNPQEGLYNELQKDKMAEAYSEIGMKGERRRGKGHDGLYQGLSTATKDTYDALHMQALPPR |
| 5 | P2A | GSGATNFSLLKQAGDVEENPGP |
| 6 | EGFRt | RKVCNGIGIGEFKDSLSINATNIKHFKNCTSISGDLHILPVAFRGDSFTHTPPLDPQELDILKTVKEITGFLLIQAWPENRTDLHAFENLEIIRGRTKQHGQFSLAVVSLNITSLGLRSLKEISDGDVIISGNKNLCYANTINWKKLFGTSGQKTKIISNRGENSCKATGQVCHALCSPEGCWGPEPRDCVSCRNVSRGRECVDKCNLLEGEPREFVENSECIQCHPECLPQAMNITCTGRGPDNCIQCAHYIDGPHCVKTCPAGVMGENNTLVWKYADAGHVCHLCHPNCTYGCTGPGLEGCPTNGPKIPSIATGMVGALLLLLVVALGIGLFM |
| 7 | 1G5 mAb ($V_H$ chain; leader sequence, CDRs 1-3, and FRs 1-4) | *MGWSYIILFLVATATGVH*SQVQLQQPGAELVKPGASVKLSCKAS**GYTFTSYWMH**WVKQRPGQGLEWIG**MIHPNSGSTNYNEKFKS**KATLTVDKSSSTAYMQLSSLTSEDSAVYYCAR**GGYFDY**WGQGTTLTVSS |
| 8 | 1G5 mAb ($V_L$ chain; leader sequence, CDRs 1-3, and FRs 1-4) | *MKTQTQVFVYMLLWLSGVDG*DIVMTQSQKFMSTSVGDRVSVTC**KASQNVGTNVA**WYQQKPGQSPKALIY**SASYRYS**GVPDRFTGSGSGTDFTLTISNVQSEDLAEYFC**QQYNSYPYT**FGGGTKLEIKR |
| 9 | 23B2 mAb ($V_H$ chain; leader sequence, CDRs 1-3, and FRs 1-4) | *MGWSCIMLFLVATATGVHS*QVQLQQPGAELVKPGASVKLSCKAS**GYTFTSYWMH**WVKQRPGQGLEWIG**MIHPNSGSTNYNEKFKS**KATLTVDKSSSTAYMQLSSLTSEDSAVYYC**ARESRQLDY**WGQGTTLTVSS |
| 10 | 23B2 mAb ($V_L$ chain; leader sequence, CDRs 1-3, and FRs 1-4) | *MDLQVQIFSFLLISASVILSRG*QIVLTQSPAIMSASPGEKVTMTC**SASSSISYMH**WYQQKPGTSPKRWIY**DTSKLAS**GVPARFSGSGSGTSYSLTISSMEAEDAATYYC**HQRSSYPLT**FGAGTKLELK |
| 11 | 15F9 mAb ($V_H$ chain; leader sequence, CDRs 1-3, and FRs 1-4) | *MGWSCIMFFLVATATGVHS*QVQLQQPGAELVKPGASVKLSCKAS**GYTFTNYWMH**WVKQRPGQGLEWIG**MIHPNSGSTNYNEKFKS**KATLTVDKSSSTAYMQLSSLTSEDSAVYYCAR**RGDGDY**WGQGTTLTVSS |
| 12 | 15F9 mAb ($V_L$ chain; leader sequence, CDRs 1-3, and FRs 1-4) | *MVLISLLFWFPGTRC*DIQMTRHPSSLSASMGERVSLTC**RASQEISGYLS**WLQQKPDGTIKRLIY**AASTLDS**GVPKRFSGSRSGSDYSLTISSLESEDFADYYC**LQYASYPYT**FGGGTKLEI |

TABLE 1-continued

| B7-H3 CAR Amino Acid Sequences | | |
|---|---|---|
| SEQ ID NO. | NAME | SEQUENCE |
| 13 | 8B12 mAb ($V_H$ chain; leader sequence, CDRs 1-3, and FRs 1-4) | *MEWSWVILILVAAATGVHS*QVQLQQPGAELVKPGASVKMSCKASG**YTFTSYWIT**WVKQRPGQGLEWIG**DIYPGSGSTNYNEKFKS**KATLTVDTSSSTAYMQLSSLTSEDSAVYYC**ARGGTRFSPFAY**WGQGTLVTVSAA |
| 14 | 8B12 mAb ($V_L$ chain; leader sequence, CDRs 1-3, and FRs 1-4) | *MKMPVRLLVLMFWIPASSS*DVLMTQTPLSLPVSLGDQASISC**RSSQSIVHSNGNTYLE**WYLQKPGQSPKLLIY**KVSNRFS**GVPDRFSGSGSGTDFTLKISRVEAEDLGVYYC**FQGSHVPWT**FGGGTKLEIKRADA |
| 15 | 12B4 mAb ($V_H$ chain; leader sequence, CDRs 1-3, and FRs 1-4) | *MGWSCIMFFLVATATGVHS*QVQLQQPGAELVKPGASVKLSCKAS**GYTFTSYWMH**WVKQRPGQGLEWIG**MIHPNSGSTNYNEKFKS**KATLTVDKSSSTAYMQLSSLTSEDSAVYYCAR**YYYGSSYAMDY**WGQGTSVTVS |
| 16 | 12B4 mAb ($V_L$ chain; leader sequence, CDRs 1-3, and FRs 1-4) | *MDFQVQIFSFLLISASVIMSRG*QIVLTQSPAIMSASPGEKVTITC**SASSSVSYMH**WFQQKPGTSPKLWIY**STSNLAS**GVPARFSGSGSGTSYSLTISRMEAEDAATYYC**QQRSSYPYT**FGGGTKLEIKRAD |
| 17 | 24D12 mAb ($V_H$ chain; leader sequence, CDRs 1-3, and FRs 1-4) | *MGWSCIMFFLVATATGVHS*QVQLQQPGAELVKPGASVKLSCKAS**GYTFTSYWMH**WVKQRPGQGLEWIG**MIHPNSGSTNYNEKFKS**KATLTVDKSSSTAYMQLSSLTSEDSAVYYCAN**YYGTNV**WGTGTTVTVS |
| 18 | 24D12 mAb ($V_L$ chain; leader sequence, CDRs 1-3, and FRs 1-4) | *METDTLLLWVLLLWVPGSTG*DIVLTQSPASLAVSLGQRATISYRAS**KSVSTSGYSYMH**WNQQKPGQPPRLLIY**LVSNLES**GVPARFSGSGSGTDFTLNIHPVEEEDAATYYC**QHIREAYT**FGRGDQSWK |

Polynucleotides, Vectors, and Host Cells

Nucleic acid molecules and polynucleotides are provided that encode any one or more of the 1B7-H-3 CARs or variants or portions thereof as described herein. In certain embodiments, a polynucleotide encoding at least a portion of the 1B7-H-3 CARs of the present disclosure comprises, or consists of, a polynucleotide having at least 70%, 75%, 80%, 85%, 90%, 91%, 92%, 93%, 94%, 95%, 96%, 97%, 98%, 99%, or more identity to the nucleotide sequence set forth in any one of SEQ ID NOs: 19-22 and 25-36.

In certain embodiments, a polynucleotide encoding a B7-H3 CAR comprises a polynucleotide that encodes a CD3ζ domain that has at least 70%, 75%, 80%, 85%, 90%, 91%, 92%, 93%, 94%, 95%, 96%, 97%, 98%, 99%, or more identity to SEQ ID NO: 22.

In certain embodiments, a polynucleotide encoding a B7-H3 CAR comprises a polynucleotide that encodes a 4-1 BB intracellular tail that has at least 70%, 75%, 80%, 85%, 90%, 91%, 92%, 93%, 94%, 95%, 96%, 97%, 98%, 99%, or more identity to SEQ ID NO: 21.

In certain embodiments, a polynucleotide encoding a B7-H3 CAR comprises a polynucleotide that encodes a CD28 intracellular tail that has at least 70%, 75%, 80%, 85%, 90%, 91%, 92%, 93%, 94%, 95%, 96%, 97%, 98%, 99%, or more identity to SEQ ID NO: 20.

In certain embodiments, a polynucleotide encoding a B7-H3 CAR comprises a polynucleotide that encodes a CD8α hinge and CD8α transmembrane region that has at least 70%, 75%, 80%, 85%, 90%, 91%, 92%, 93%, 94%, 95%, 96%, 97%, 98%, 99%, or more identity to SEQ ID NO: 19.

In certain embodiments, a polynucleotide encoding a B7-H3 CAR comprises a polynucleotide that encodes at least a portion of a B7-H3 binding domain that has at least 70%, 75%, 80%, 85%, 90%, 91%, 92%, 93%, 94%, 95%, 96%, 97%, 98%, 99%, or more identity to any one or more of SEQ ID NOs: 25-36, such as, but not limited to, SEQ ID NO: 25 and SEQ ID NO: 26, SEQ ID NO: 27 and SEQ ID NO: 28, SEQ ID NO: 29 and SEQ ID NO: 30, SEQ ID NO: 31 and SEQ ID NO: 32, SEQ ID NO: 33 and SEQ ID NO: 34, or SEQ ID NO: 35 and SEQ ID NO: 36.

Polynucleotides of the present disclosure further include polynucleotides encoding a marker, such as GFP and/or EGFRt. In certain embodiments, a polynucleotide encoding EGFRt comprises a polynucleotide that has at least 70%, 75%, 80%, 85%, 90%, 91%, 92%, 93%, 94%, 95%, 96%, 97%, 98%, 99%, or more identity to SEQ ID NO: 24.

In some embodiments, polynucleotides of the present disclosure further include polynucleotides encoding a self-cleaving peptide, such as a 2A peptide. An exemplary 2A peptide is P2A encoded by a polynucleotide that has at least 70%, 75%, 80%, 85%, 90%, 91%, 92%, 93%, 94%, 95%, 96%, 97%, 98%, 99%, or more identity to SEQ ID NO: 23.

Table 2 below lists the nucleotide sequences of various B7-H3 CAR components. For each mAb sequence, the leader sequence is shown italicized, the FR1-4 sequences are shown underlined, and the CDR1-3 sequences are shown in bold.

TABLE 2

B7-H3 CAR Nucleotide Sequences

| SEQ ID NO. | NAME | SEQUENCE |
|---|---|---|
| 19 | CD8α hinge and CD8α transmembrane region | accacgacgccagcgccgcgaccaccaacaccggcgcccaccatcgcgtcgc<br>agcccctgtccctgcgcccagaggcgtgccggccagcggcgggggcgcagt<br>gcacacgagggggctggacttcgcctgtgatatctacatctgggcgcccttggccg<br>ggacttgtggggtccttctcctgtcactggttatcaccctttactgc |
| 20 | CD28 intracellular tail | aggagtaagaggagcaggctcctgcacagtgactacatgaacatgactccccg<br>ccgccccgggcccacccgcaagcattaccagccctatgccccaccacgcgactt<br>cgcagcctatcgctcc |
| 21 | 4-1BB intracellular tail | aaacggggcagaaagaaactcctgtatatattcaaacaaccatttatgagacca<br>gtacaaactactcaagaggaagatggctgtagctgccgatttccagaagaagaa<br>gaaggaggatgtgaactg |
| 22 | CD3ζ | agagtgaagttcagcaggagcgcagacgcccccgcgtaccagcagggccag<br>aaccagctctataacgagctcaatctaggacgaagagaggagtacgatgttttgg<br>acaagagacgtggccgggaccctgagatgggggggaaagccgcagagaagg<br>aagaaccctcaggaaggcctgtacaatgaactgcagaaagataagatggcgg<br>aggcctacagtgagattgggatgaaaggcgagcgccggaggggcaaggggc<br>acgatggcctttaccagggtctcagtacagccaccaaggacacctacgacgccc<br>ttcacatgcaggccctgccccctcgctaa |
| 23 | P2A | ggaagcggagctactaacttcagcctgctgaagcaggctggagacgtggagga<br>gaaccctggacct |
| 24 | EGFRt | cgcaaagtgtgtaacggaataggtattggtgaatttaaagactcactctccataaat<br>gctacgaatattaaacacttcaaaaactgcacctccatcagtggcgatctccacat<br>cctgccggtggcatttaggggtgactccttcacacatactcctcctctggatccaca<br>ggaactggatattctgaaaaccgtaaaggaaatcacagggtttttgctgattcagg<br>cttggcctgaaaacaggacggacctccatgcctttgagaacctagaaatcatacg<br>cggcaggaccaagcaacatggtcagttttctcttgcagtcgtcagcctgaacataa<br>catccttgggattacgctccctcaaggagataagtgatggagatgtgataatttcag<br>gaaacaaaaatttgtgctatgcaaatacaataaactggaaaaaactgtttgggac<br>ctccggtcagaaaaccaaaattataagcaacagaggtgaaaacagctgcaag<br>gccacaggccaggtctgccatgccttgtgctcccccgagggctgctggggcccg<br>gagcccagggactgcgtctcttgccggaatgtcagccgaggcagggaatgcgtg<br>gacaagtgcaaccttctggagggtgagccaagggagtttgtggagaactctgagt<br>gcatacagtgccacccagagtgcctgcctcaggccatgaacatcacctgcacag<br>gacggggaccagacaactgtatccagtgtgcccactacattgacggcccccact<br>gcgtcaagacctgcccggcaggagtcatgggagaaaacaacaccctggtctgg<br>aagtacgcagacgccggccatgtgtgccacctgtgccatccaaactgcacctac<br>ggatgcactgggccaggtcttgaaggctgtccaacgaatgggcctaagatcccgt<br>ccatcgccactgggatggtgggggccctcctcttgctgctggtggtggccctgggg<br>atcggcctcttcatg |
| 25 | 1G5 mAb ($V_H$ chain; leader sequence, CDRs 1-3, and FRs 1-4) | *atgggatggagctatatcatcctctttttggtagcaacagctacaggtgtccactcc*c<br>aggtccaactgcagcagcctggggctgagctggtaaagcctggggcttcagtga<br>agttgtcctgcaaggcttct**ggctacactttcaccagctactggatgcac**tgggt<br>gaagcagaggcctggacaaggccttgagtggattgga**atgattcatcctaatag**<br>**tggtagtactaactacaatgagaagttcaagagc**aaggccacactgactgta<br>gacaaatcctccagcacagcctacatgcaactcagcagcctgacatctgaggac<br>tctgcggtctattactgtgcaa**ggggggggtactttgactac**tggggccaaggc<br>accactctcacagtctcctca |
| 26 | 1G5 mAb ($V_L$ chain; leader sequence, CDRs 1-3, and FRs 1-4) | *atgaagacacagactcaggtctttgtatacatgttgctgtggttgtctggtgttgatgg*<br>*a*gacattgtgatgacccagtctcaaaaattcatgtccacatcagtaggagacagg<br>gtcagcgtcacctgc**aaggccagtcagaatgtgggtactaatgtagcc**tggta<br>tcaacagaaaccagggcaatctcctaaagcactgatttac**tcggcatcctaccg**<br>**gtacagt**ggagtccctgatcgcttcacaggcagtggatctgggacagatttcactc<br>tcaccatcagcaatgtgcagtctgaagacttggcagagtatttctgt**cagcaatata**<br>**acagctatccgtacacg**ttcggaggggggaccaagctggaaataaaacgg |
| 27 | 23B2 mAb ($V_H$ chain; leader sequence, CDRs 1-3, and FRs 1-4) | *atgggatggagctgtatcatgctctttttggtagcaacagctacaggtgtccactcc*c<br>aggtccaactgcagcagcctggggctgagctggtaaagcctggggcttcagtga<br>agttgtcctgcaaggcttct**ggctacactttcaccagctactggatgcac**tgggt<br>gaagcagaggcctggacaaggccttgagtggattgga**atgattcatcctaatag**<br>**tggtagtactaactacaatgagaagttcaagagc**aaggccacactgactgta<br>gacaaatcctccagcacagcctacatgcaactcagcagcctgacatctgaggac<br>tctgcggtctattactgt**gcaagagagagtagacagctcgactac**tggggcca<br>aggcaccactctcacagtctcctca |

TABLE 2-continued

| SEQ ID NO. | NAME | SEQUENCE |
|---|---|---|
| | | B7-H3 CAR Nucleotide Sequences |
| 28 | 23B2 mAb ($V_L$ chain; leader sequence, CDRs 1-3, and FRs 1-4) | *atggatttacaagtgcagattttcagcttcctgctaatcagtgcctcagtcatactgtc*<br>*cagagga*caaattgttctcacccagtctccagcaatcatg**tctgcatctccaggg**<br>**gagaaggtcaccatgacctgcagtgccagctcaagtataagttacatgcac**<br>tggtaccagcagaagccaggcacctcccccaaaagatggatttat**gacacatc**<br>**caaactggcttct**ggagtccctgctcgcttcagtggcagtgggtctgggacctctta<br>ttctctcacaatcagcagcatggaggctgaagatgctgccacttattactgc**catca**<br>**gcggagtagttacccgctcacg**ttcggtgctgggaccaagctggagctgaaa |
| 29 | 15F9 mAb ($V_H$ chain; leader sequence, CDRs 1-3, and FRs 1-4) | *atgggatggagctgtatcatgttctttttggtagcaacagctacaggtgtccactcc*c<br>aggtccaactgcagcagcctggggctgagctggtaaagcctggggcttcagtga<br>agttgtcctgcaaggcttct**ggctacactttcaccaactactggatgcac**tgggt<br>gaagcagaggcctggacaaggccttgagtggattgga**atgattcatcctaatag**<br>**tggtagtactaactacaatgagaagttcaagagc**aaggccacactgactgta<br>gacaaatcctccagcacagcctacatgcaactcagcagcctgacatctgaggac<br>tctgcggtctattactgtgcaagg**cgaggggacggggactac**tggggccaagg<br>caccactctcacagtctcctcag |
| 30 | 15F9 mAb ($V_L$ chain; leader sequence, CDRs 1-3, and FRs 1-4) | *atggttcttatttccttgctgttctggtttccaggtaccagatgt*gacatccagatgacc<br>cggcatccttcttctttatctgcctctatgggagaaagagtcagtctcacttgt**cgggc**<br>**aagtcaggaaattagtggttacttaagc**tggcttcagcagaaaccagatggaa<br>ctattaaacgcctgatttac**gccgcatccactttagattct**ggtgtcccaaaaagg<br>ttcagtggcagtaggtctgggtcagattattctctcaccatcagcagccttgagtctg<br>aagattttgcagactattactgt**ctacaatatgctagttatccgtacacg**ttcggag<br>gggggaccaagctggaaata |
| 31 | 8B12 mAb ($V_H$ chain; leader sequence, CDRs 1-3, and FRs 1-4) | *atggaatggagctgggtcatcctcatttttggtagcagcagctacaggtgtccactcc*<br>caggtccaactgcagcagcctggggctgagcttgtgaagcctggggcttcagtga<br>agatgtcctgcaaggcttct**ggctacaccttcaccagctactggataacc**tggg<br>tgaagcagaggcctggacaaggccttgagtggattgga**gatatttatcctggta**<br>**gtggtagtactaactacaatgagaagttcaagagc**aaggccactctgactgta<br>gacacatcctccagcacagcctacatgcagctcagcagcctgacatctgaggac<br>tctgcggtctattactgt**gcaagaggggtactagattcagcccctttgcttac**t<br>ggggccaagggactctggtcactgtctctgcagctac |
| 32 | 8B12 mAb ($V_L$ chain; leader sequence, CDRs 1-3, and FRs 1-4) | *atgaagatgcctgttaggctgttggtgctgatgttctggattcctgcttccagcagt*ga<br>tgttttgatgacccaaactccactctccctgcctgtcagtcttggagatcaagcctcc<br>atctcttgc**agatctagtcagagcattgtacatagtaatggaaacacctatttag**<br>**aa**tggtacctgcagaaaccaggccagtctccaaagctcctgatctac**aaagtttc**<br>**caaccgattttct**ggggtcccagacaggttcagtggcagtggatcagggacaga<br>tttcacactcaagatcagcagagtggaggctgaggatctgggagtttattactgc**ttt**<br>**caaggttcacatgttccgtggacg**ttcggtggaggcaccaagctggaaatcaa<br>acgggctgatgct |
| 33 | 12B4 mAb ($V_H$ chain; leader sequence, CDRs 1-3, and FRs 1-4) | *atgggatggagctgtatcatgttctttttggtagcaacagctacaggtgtccactcc*c<br>aggtccaactgcagcagcctggggctgagctggtaaagcctggggcttcagtga<br>agttgtcctgcaaggcttct**ggctacactttcaccagctactggatgcac**tgggt<br>gaagcagaggcctggacaaggccttgagtggattgga**atgattcatcctaatag**<br>**tggtagtactaactacaatgagaagttcaagagc**aaggccacactgactgta<br>gacaaatcctccagcacagcctacatgcaactcagcagcctgacatctgaggac<br>tctgcggtctattactgtgcaaga**tattactacggtagtagctatgctatggacta**<br>**c**tggggtcaaggaacctcagtcaccgtctctca |
| 34 | 12B4 mAb ($V_L$ chain; leader sequence, CDRs 1-3, and FRs 1-4) | *atggattttcaggtgcagattttcagcttcctgctaatcagtgcctcagtcataatgtcc*<br>*agagga*caaattgttctcacccagtctccagcaatcatgtctgcatctccagggga<br>gaaggtcaccataacctgc**agtgccagctcaagtgtaagttacatgcac**tggtt<br>ccagcagaagccaggcacttctcccaaactctggatttat**agcacatccaacct**<br>**ggcttct**ggagtccctgctcgcttcagtggcagtggatctgggacctcttactctctc<br>acaatcagccgaatggaggctgaagatgctgccacttattactgc**cagcaaagg**<br>**agtagttacccgtacacg**ttcggaggggggaccaagctggaaataaaacggg<br>ctgatg |
| 35 | 24D12 mAb ($V_H$ chain; leader sequence, CDRs 1-3, and FRs 1-4) | *atgggatggagctgtatcatgttctttttggtagcaacagctacaggtgtccactccc*<br>aggtccaactgcagcagcctggggctgagctggtaaagcctggggcttcagtga<br>agttgtcctgcaaggcttct**ggctacactttcaccagctactggatgcac**tgggt<br>gaagcagaggcctggacaaggccttgagtggattgga**atgattcatcctaatag**<br>**tggtagtactaactacaatgagaagttcaagagc**aaggccacactgactgta<br>gacaaatcctccagcacagcctacatgcaactcagcagcctgacatctgaggac<br>tctgcggtctattactgtgcaaat**tactacggtactaatgtc**tggggcacagggac<br>cacggtcaccgtctct |
| 36 | 24D12 mAb ($V_L$ chain; leader sequence, CDRs 1-3, and FRs 1-4) | *atggagacagacacactgctgctatgggtactgctgctctgggttccaggttccact*<br>*ggt*gacattgtgctgacacagtctcctgcttccttagctgtatctctggggcagaggg<br>ccaccatctcatacagggccagc**aaaagtgtcagtacatctggctatagttata**<br>**tgcac**tggaaccaacagaaaccaggacagccacccagactcctcatctat**cttg**<br>**tatccaacctagaatct**ggggtccctgccaggttcagtggcagtgggtctgggac |

TABLE 2-continued

B7-H3 CAR Nucleotide Sequences

| SEQ ID NO. | NAME | SEQUENCE |
|---|---|---|
| | | agacttcaccctcaacatccatcctgtggaggaggaggatgctgcaacctattact gt**cagcacattagggaagcttacacg**ttcggaagggggaccaaagctgga aa |

In any of the embodiments described herein, B7-H3 CARs, portions, or variants thereof may be codon-optimized for a host cell containing the polynucleotide using known techniques (Scholten et al., 2006). Codon optimization can be performed using, e.g., the GenScript® OptimumGene™ tool. Codon-optimized sequences include sequences that are partially or fully codon-optimized.

A polynucleotide encoding a B7-H3 CAR of this disclosure can be inserted into an expression vector, such as a viral vector, for transduction into a host cell, such as a T cell. In some embodiments, an expression construct of the present disclosure comprises a B7-H3 CAR polynucleotide (e.g., SEQ ID NOs: 19-22 plus one or more of SEQ ID NOs:25-36 or portions there) and optionally a P2A self-cleaving peptide (e.g., SEQ ID NO. 23) and optionally an EGFRt marker (e.g., SEQ ID No. 24) operably linked to an expression control sequence such as a promoter.

In certain embodiments, polynucleotides of the present disclosure may be operatively linked to certain elements of the vector. For example, polynucleotide sequences that are needed to affect the expression and processing of coding sequences to which they are ligated may be operatively linked. Expression control sequences may include appropriate transcription initiation, termination, promoter and enhancer sequences; efficient RNA processing signals such as splicing and polyadenylation signals; sequences that stabilize cytoplasmic mRNA; sequences that enhance translation efficiency; sequences that enhance protein stability; and possibly sequences that enhance protein secretion. Expression control sequences may be operatively linked if they are contiguous with the gene of interest and expression control sequences that act in trans or at a distance to control the gene of interest.

In certain embodiments, the expression construct is comprised in a vector which may integrate into a host cell's genome or promote integration of the polynucleotide insert upon introduction into the host cell and thereby replicate along with the host genome, such as a viral vector. Viral vectors include retrovirus, adenovirus, parvovirus, coronavirus, negative strand RNA viruses, positive strand RNA viruses, and double-stranded DNA viruses. (Coffin, J. M., Retroviridae: The viruses and their replication, In Fundamental Virology, Third Edition, B. N. Fields et al., Eds., Lippincott-Raven Publishers, Philadelphia, 1996).

Construction of an expression vector that is used for genetically engineering and producing a CAR of interest can be accomplished by using any suitable molecular biology engineering techniques known in the art. To obtain efficient transcription and translation, a polynucleotide in each recombinant expression construct includes at least one appropriate expression control sequence, such as a leader sequence and particularly a promoter operably linked to the nucleotide sequence encoding the immunogen. Methods for making CARs of the present disclosure are described, for example, in U.S. Pat. Nos. 6,410,319; 7,446,191; U.S. Patent Publ. No. 2010/065818; U.S. Pat. No. 8,822,647; PCT Publ. No. WO 2014/031687; U.S. Pat. No. 7,514,537; Brentjens et al., 2007; and Walseng et al., 2017; the techniques of which are herein incorporated by reference.

In certain embodiments, polynucleotides of the present disclosure are used to transfect/transduce a host cell, such as a T cell or an NK cell, for use in adoptive transfer therapy to target B7-H3. Cells may be induced to incorporate the vector or other material by use of a viral vector, transformation via calcium phosphate precipitation, DEAE-dextran, electroporation, microinjection, or other methods. (Sambrook et al., Molecular Cloning: A Laboratory Manual 2d ed. (Cold Spring Harbor Laboratory, 1989)). T cells and/or NK cells can be collected using known techniques, and the various subpopulations or combinations thereof can be enriched or depleted by known techniques, such as by affinity binding to antibodies, flow cytometry, or immunomagnetic selection. In certain embodiments, the T cell is a CD4+ T cell, a CD8+ T cell, a CD4− CD8− double negative T cell, a naïve T cell, a central memory T cell, an effector memory T cell, a stem cell memory T cell, or any combination thereof. Methods for transfecting/transducing T cells with polynucleotides have been previously described (U.S. Patent Application Pub. No. US 2004/0087025) as have adoptive transfer procedures using T cells of desired target-specificity (Schmitt et al. 2009; Dossett et al. 2009; Till et al. 2008; Wang et al. 2007; Kuball et al., 2007; Leen et al., 2007; U.S. Patent Publ. No. 2011/0243972; U.S. Patent Publ. No. 2011/0189141), such that adaptation of these methodologies to the presently disclosed B7-H3 CARs of the present disclosure is within the scope of the present disclosure.

In certain embodiments, a B7-H3 CAR of the instant disclosure is expressed by a host cell, such as a T cell and/or a NK cell, and the host cell recognizes and initiates an immune response to a target cell expressing B7-H3. As explained in greater detail below, the target cell includes malignant cells, such as cancer cells.

In any of the embodiments disclosed herein, B7-H3 CARs, when expressed by a host cell such as a T cell and/or a NK cell, results in at least one of the following outcomes (i) improved cell signaling, cytotoxic activity, proliferation, and/or survival in response to B7-H3 relative to a T cell and/or a NK cell that does not express the B7-H3 CAR of the present disclosure, wherein improved cell signaling optionally comprises increased and/or sustained cytokine production and/or release, and/or phosphorylation of one or more protein associated with an immune cell response to antigen-binding, or any combination thereof; (ii) improved cell activity in response to antigen relative to a T cell and/or a NK cell that does not express the B7-H3 CAR of the present disclosure, wherein improved cell signaling optionally comprises increased mobilization of intracellular calcium, killing activity, proliferation, earlier activation in response to antigen, or any combination thereof; (iii) improved cell signaling and/or activity, relative to a T cell and/or a NK cell that does not express the B7-H3 CAR of the present disclosure, upon binding to a target antigen that is expressed at a low level or an intermediate level on a target cell surface; (iv) reducing or suppressing growth, area, volume, and/or spread of a tumor that expresses an antigen that is recognized and/or specifically bound by the B7-H3 CAR, of killing tumor cells, and/or of increasing survival of the subject to a greater degree and/or for a longer period of time as compared to a T cell and/or a NK cell that does not express the B7-H3 CAR of the present disclosure; (iv) improved sensitivity to B7-H3 antigen expression compared to a T cell that does not express the B7-H3 CAR of the present disclosure; or (v) any combination of (i)-(iv).

Functional characterization of B7-H3 CARs described herein may be performed according to any art-accepted methodologies for assaying T cell and/or NK cell activity, including determination of T cell and/or NK cell binding, activation or induction and also including determination of T cell and/or NK cell responses that are antigen-specific. Examples include determination of intracellular calcium, T cell proliferation, T cell and/or NK cell cytokine release, antigen-specific T cell and/or NK cell stimulation, MHC-restricted T cell and/or NK cell stimulation, cytotoxic activity, changes in T cell and/or NK cell phenotypic marker expression, phosphorylation of certain T cell and/or NK cell proteins, and other measures of T cell and/or NK cell functions. Procedures for performing these and similar assays are described herein and/or may be found, for example, in Lefkovits (*Immunology Methods Manual: The Comprehensive Sourcebook of Techniques,* 1998). See, also, *Current Protocols in Immunology; Weir, Handbook of Experimental Immunology*, Blackwell Scientific, Boston, MA (1986); Mishell and Shigii (eds.) *Selected Methods in Cellular Immunology*, Freeman Publishing, San Francisco, CA (1979); Green and Reed, *Science* 281:1309 (1998) and references cited therein.

In some embodiments, kits are provided comprising (a) a B7-H3 CAR vector described herein, (b) a B7-H3 CAR polynucleotide (e.g., SEQ ID NOs: 19-22 plus one or more of SEQ ID NOs:25-36 or portions there), (c) marker peptide and self-cleaving peptide (SEQ ID NOs: 23 and 24), (d) instructions, and/or (e) one or more reagents for transducing the vector or polynucleotides into a host cell.

B7-H3 Binding Domain

In certain embodiments, the 1B7-H-3 binding domain comprises one or more heavy chain CDRs (e.g., one $V_H$ CDR, two $V_H$ CDRs, or three $V_H$ CDRs) and/or one or more light chain CDRs (e.g., one $V_L$ CDR, two $V_L$ CDRs, or three $V_L$ CDRs). Depending on the number of the CDRs, a corresponding number of FRs can be used. For example, if 3 CDRs are used for $V_H$ or $V_L$, 4 FRs are used for the corresponding $V_H$ or $V_L$, with an FR disposed at the N-terminus of the first CDR, between two CDRs, and/or at the C-terminus of the last CDR. In some embodiments, a leader having an amino acid sequence set forth by any one of SEQ ID NOs: 100-109 is added to the N-terminus of $V_H$, $V_L$, or both. In some embodiments, a linker is disposed between the $V_H$ and $V_L$ domains. Suitable linker sequences are disclosed in the foregoing section. One of ordinary skill in the art can select the CDR sequences from Table 3, FR sequences from Table 4, and leader sequences from Table 5 below to assemble a desirable scFv sequence.

TABLE 3

| Amino Acid Sequences of CDRs | | |
|---|---|---|
| $V_H$ CDR Sequences | | |
| CDR1 | CDR2 | CDR3 |
| GYTFTSYWMH (SEQ ID NO: 37) | MIHPNSG-STNYNEKFKS (SEQ ID NO: 46) | GGYFDY (SEQ ID NO: 54) |
| GYTFTSYWMH (SEQ ID NO: 37) | MIHPNSG-STNYNEKFKS (SEQ ID NO: 46) | ARESRQLDY (SEQ ID NO: 55) |
| GYTFTNYWMH (SEQ ID NO: 38) | MIHPNSG-STNYNEKFKS (SEQ ID NO: 46) | RGDGDY (SEQ ID NO: 56) |
| GYTFTSYWIT (SEQ ID NO: 39) | DIYPGSG-STNYNEKFKS (SEQ ID NO: 47) | ARGGTRFSPFAY (SEQ ID NO: 57) |
| GYTFTSYWMH (SEQ ID NO: 37) | MIHPNSG-STNYNEKFKS (SEQ ID NO: 46) | YYYGSSYAMDY (SEQ ID NO: 58) |
| GYTFTSYWMH (SEQ ID NO: 37) | MIHPNSG-STNYNEKFKS (SEQ ID NO: 46) | YYGTNV (SEQ ID NO: 59) |
| $V_L$ CDR Sequences | | |
| CDR1 | CDR2 | CDR3 |
| KASQNVGTNVA (SEQ ID NO: 40) | SASYRYS (SEQ ID NO: 48) | QQYNSYPYT (SEQ ID NO: 60) |
| SASSSISYMH (SEQ ID NO: 41) | DTSKLAS (SEQ ID NO: 49) | HQRSSYPLT (SEQ ID NO: 61) |
| RASQEISGYLS (SEQ ID NO: 42) | AASTLDS (SEQ ID NO: 50) | LQYASYPYT (SEQ ID NO: 62) |
| RSSQSIVHSNGNTYLE (SEQ ID NO: 43) | KVSNRFS (SEQ ID NO: 51) | FQGSHVPWT (SEQ ID NO: 63) |
| SASSSVSYMH (SEQ ID NO: 44) | STSNLAS (SEQ ID NO: 52) | QQRSSYPYT (SEQ ID NO: 64) |
| KSVSTSGYSYMH (SEQ ID NO: 45) | LVSNLES (SEQ ID NO: 53) | QHIREAYT (SEQ ID NO: 65) |

TABLE 4

| Amino Acid Sequences of FRs | | | |
|---|---|---|---|
| $V_H$ FR Sequences | | | |
| FR1 | FR2 | FR3 | FR4 |
| QVQLQQPGAELVKPG ASVKLSCKAS (SEQ ID NO: 66) | WVKQRPGQ GLEWIG (SEQ ID NO: 74) | KATLTVDKSSSTAYMQLSSL TSEDSAVYYCAR (SEQ ID NO: 81) | WGQGTTLT VSS (SEQ ID NO: 90) |

TABLE 4-continued

| Amino Acid Sequences of FRs | | | |
|---|---|---|---|
| QVQLQQPGAELVKPGASVKLSCKAS (SEQ ID NO: 66) | WVKQRPGQGLEWIG (SEQ ID NO: 74) | KATLTVDKSSSTAYMQLSSLTSEDSAVYYC (SEQ ID NO: 82) | WGQGTTLTVSS (SEQ ID NO: 90) |
| QVQLQQPGAELVKPGASVKLSCKAS (SEQ ID NO: 66) | WVKQRPGQGLEWIG (SEQ ID NO: 74 | KATLTVDKSSSTAYMQLSSLTSEDSAVYYCAR (SEQ ID NO: 81) | WGQGTTLTVSS (SEQ ID NO: 90) |
| QVQLQQPGAELVKPGASVKMSCKAS (SEQ ID NO: 67) | WVKQRPGQGLEWIG (SEQ ID NO: 74) | KATLTVDTSSSTAYMQLSSLTSEDSAVYYC (SEQ ID NO: 82) | WGQGTLVTVSAA (SEQ ID NO: 91) |
| QVQLQQPGAELVKPGASVKLSCKAS (SEQ ID NO: 66) | WVKQRPGQGLEWIG (SEQ ID NO: 74) | KATLTVDKSSSTAYMQLSSLTSEDSAVYYCAR (SEQ ID NO: 81) | WGQGTSVTVS (SEQ ID NO: 92) |
| QVQLQQPGAELVKPGASVKLSCKAS (SEQ ID NO: 66) | WVKQRPGQGLEWIG (SEQ ID NO: 74) | KATLTVDKSSSTAYMQLSSLTSEDSAVYYCAN (SEQ ID NO: 83) | WGTGTTVTVS (SEQ ID NO: 93) |
| $V_L$ FR Sequences | | | |
| FR1 | FR2 | FR3 | FR4 |
| DIVMTQSQKFMSTSVGDRVSVTC (SEQ ID NO: 68) | WYQQKPGQSPKALIY (SEQ ID NO: 75) | GVPDRFTGSGSGTDFTLTISNVQSEDLAEYFC (SEQ ID NO: 84) | FGGGTKLEIKR (SEQ ID NO: 94) |
| QIVLTQSPAIMSASPGEKVTMTC (SEQ ID NO: 69) | WYQQKPGTSPKRWIY (SEQ ID NO: 76) | GVPARFSGSGSGTSYSLTISSMEAEDAATYYC (SEQ ID NO: 85) | FGAGTKLELK (SEQ ID NO: 95) |
| DIQMTRHPSSLSASMGERVSLTC (SEQ ID NO: 70) | WLQQKPDGTIKRLIY (SEQ ID NO: 77) | GVPKRFSGSRSGSDYSLTISSLESEDFADYYC (SEQ ID NO: 86) | FGGGTKLEI (SEQ ID NO: 96) |
| DVLMTQTPLSLPVSLGDQASISC (SEQ ID NO: 71) | WYLQKPGQSPKLLIY (SEQ ID NO: 78) | GVPDRFSGSGSGTDFTLKISRVEAEDLGVYYC (SEQ ID NO: 87) | FGGGTKLEIKRADA (SEQ ID NO: 97) |
| QIVLTQSPAIMSASPGEKVTITC (SEQ ID NO: 72) | WFQQKPGTSPKLWIY (SEQ ID NO: 79) | GVPARFSGSGSGTSYSLTISRMEAEDAATYYC (SEQ ID NO: 88) | FGGGTKLEIKRAD (SEQ ID NO: 98) |
| DIVLTQSPASLAVSLGQRATISYRAS (SEQ ID NO: 73) | WNQQKPGQPPRLLIY (SEQ ID NO: 80) | GVPARFSGSGSGTDFTLNIHPVEEEDAATYYC (SEQ ID NO: 89) | FGRGDQSWK (SEQ ID NO: 99) |

TABLE 5

| Amino Acid Sequences of Leader Sequences |
|---|
| MGWSYIILFLVATATGVHS (SEQ ID NO: 100) |
| MGWSCIMLFLVATATGVHS (SEQ ID NO: 101) |
| MGWSCIMFFLVATATGVHS (SEQ ID NO: 102) |
| MEWSWVILILVAAATGVHS (SEQ ID NO: 103) |

TABLE 5-continued

| Amino Acid Sequences of Leader Sequences |
|---|
| MKTQTQVFVYMLLWLSGVDG (SEQ ID NO: 104) |
| MDLQVQIFSFLLISASVILSRG (SEQ ID NO: 105) |
| MVLISLLFWFPGTRC (SEQ ID NO: 106) |

TABLE 5-continued

| Amino Acid Sequences of Leader Sequences |
| --- |
| MKMPVRLLVLMFWIPASSS (SEQ ID NO: 107) |
| MDFQVQIFSFLLISASVIMSRG (SEQ ID NO: 108) |
| METDTLLLWVLLLWVPGSTG (SEQ ID NO: 109) |

In certain embodiments, the amino acid sequence of the binding domain comprises a $V_H$ sequence comprising a CDR1 selected from SEQ ID NOs: 37-39, a CDR2 selected from SEQ ID NOs: 46-47, or a CDR3 selected from SEQ ID NOs: 54-59.

In certain embodiments, the amino acid sequence of the binding domain comprises a $V_H$ sequence comprising a CDR1 selected from SEQ ID NOs: 37-39, a CDR2 selected from SEQ ID NOs: 46-47, and a CDR3 selected from SEQ ID NOs: 54-59.

In certain embodiments, the amino acid sequence of the binding domain comprises a $V_H$ sequence comprising a combination of CDR1, CDR2, and CDR3 included in Table 8. Each row of Table 8 illustrates a specific combination of CDR1, CDR2, and CDR3. For instance, the $V_H$ sequence comprises CDR1 set forth by SEQ ID NO: 37, CDR2 set forth by SEQ ID NO: 46, and CDR3 set forth by SEQ ID NO: 54.

In certain embodiments, the amino acid sequence of the binding domain comprises a $V_H$ sequence comprising an FR1 selected from SEQ ID NOs: 66-67, an FR2 represented by SEQ ID NO: 74, an FR3 selected from SEQ ID NOs: 81-83, or an FR4 selected from SEQ ID NOs: 90-93.

In certain embodiments, the amino acid sequence of the binding domain comprises a $V_H$ sequence comprising an FR1 selected from SEQ ID NOs: 66-67, an FR2 represented by SEQ ID NO: 74, an FR3 selected from SEQ ID NOs: 81-83, and an FR4 selected from SEQ ID NOs: 90-93.

In certain embodiments, the amino acid sequence of the binding domain comprises a $V_L$ sequence comprising a CDR1 selected from SEQ ID NOs: 40-45, a CDR2 selected from SEQ ID NOs: 48-53, or a CDR3 selected from SEQ ID NOs: 60-65.

In certain embodiments, the amino acid sequence of the binding domain comprises a $V_L$ sequence comprising a CDR1 selected from SEQ ID NOs: 40-45, a CDR2 selected from SEQ ID NOs: 48-53, and a CDR3 selected from SEQ ID NOs: 60-65.

In certain embodiments, the amino acid sequence of the binding domain comprises a $V_L$ sequence comprising a combination of CDR1, CDR2, and CDR3 included in Table 8. Each row of Table 8 illustrates a specific combination of CDR1, CDR2, and CDR3. For instance, the $V_L$ sequence comprises CDR1 set forth by SEQ ID NO: 40, CDR2 set forth by SEQ ID NO: 48, and CDR3 set forth by SEQ ID NO: 60.

In certain embodiments, the amino acid sequence of the binding domain comprises a $V_L$ sequence comprising an FR1 selected from SEQ ID NOs: 68-73, an FR2 selected from SEQ ID NOs: 75-80, an FR3 selected from SEQ ID NOs: 84-89, or an FR4 selected from SEQ ID NOs: 94-99.

In certain embodiments, the amino acid sequence of the binding domain comprises a $V_L$ sequence comprising an FR1 selected from SEQ ID NOs: 68-73, an FR2 selected from SEQ ID NOs: 75-80, an FR3 selected from SEQ ID NOs: 84-89, and an FR4 selected from SEQ ID NOs: 94-99.

In certain embodiments, the amino acid sequence of the binding domain comprises a $V_H$ sequence comprising a CDR1 selected from SEQ ID NOs: 37-39, a CDR2 selected from SEQ ID NOs: 46-47, and a CDR3 selected from SEQ ID NOs: 54-59; and a $V_L$ sequence comprising a CDR1 selected from SEQ ID NOs: 40-45, a CDR2 selected from SEQ ID NOs: 48-53, and a CDR3 selected from SEQ ID NOs: 60-65. In some embodiments, the $V_H$ sequence further comprises an FR1 selected from SEQ ID NOs: 66-67, an FR2 represented by SEQ ID NO: 74, an FR3 selected from SEQ ID NOs: 81-83, and an FR4 selected from SEQ ID NOs: 90-93. In some embodiments, the $V_L$ sequence further comprises an FR1 selected from SEQ ID NOs: 68-73, an FR2 selected from SEQ ID NOs: 75-80, an FR3 selected from SEQ ID NOs: 84-89, and an FR4 selected from SEQ ID NOs: 94-99. In some embodiments, the $V_H$ sequence further comprises a leader selected from SEQ ID NOs: 100-103. In some embodiments, the $V_L$ sequence further comprises a leader selected from SEQ ID NOs: 104-109.

This disclosure also encompasses a binding domain comprises various combinations of $V_H$ and $V_L$ sequences disclosed above. Each $V_H$ sequence disclosed above can be combined with various sequences of $V_L$s disclosed above. It is within the purview of one of ordinary skill in the art to select a $V_H$ sequence and a $V_L$ sequence based on the disclosure in this document to obtain a binding domain that specifically binds to at least a portion of B7-H3.

In certain embodiments, the binding domain comprises an scFv comprising a $V_H$ domain and a $V_L$ domain. The amino acid sequences of the $V_H$ domain and the $V_L$ domain are shown in Table 6 below. For each sequence, the FR1-4 sequences are shown underlined and the CDR1-3 sequences are shown in bold. In some embodiments, the binding domain comprises an scFv comprising a $V_H$ domain having an amino acid sequence selected from SEQ ID NOs: 110-115 and a $V_L$ domain having an amino acid sequence selected from SEQ ID NOs: 116-121.

For example, the scFv comprises a $V_H$ domain having an amino acid sequence represented by SEQ ID NO: 110 and a $V_L$ domain having an amino acid sequence represented by SEQ ID NO: 116; a $V_H$ domain having an amino acid sequence represented by SEQ ID NO: 110 and a $V_L$ domain having an amino acid sequence represented by SEQ ID NO: 117; a $V_H$ domain having an amino acid sequence represented by SEQ ID NO: 110 and a $V_L$ domain having an amino acid sequence represented by SEQ ID NO: 118; a $V_H$ domain having an amino acid sequence represented by SEQ ID NO: 110 and a $V_L$ domain having an amino acid sequence represented by SEQ ID NO: 119; a $V_H$ domain having an amino acid sequence represented by SEQ ID NO: 110 and a $V_L$ domain having an amino acid sequence represented by SEQ ID NO: 120; a $V_H$ domain having an amino acid sequence represented by SEQ ID NO: 110 and a $V_L$ domain having an amino acid sequence represented by SEQ ID NO: 121; a $V_H$ domain having an amino acid sequence represented by SEQ ID NO: 111 and a $V_L$ domain having an amino acid sequence represented by SEQ ID NO: 116; a $V_H$ domain having an amino acid sequence represented by SEQ ID NO: 111 and a $V_L$ domain having an amino acid sequence represented by SEQ ID NO: 117; a $V_H$ domain having an amino acid sequence represented by SEQ ID NO: 111 and a $V_L$ domain having an amino acid sequence represented by SEQ ID NO: 118; a $V_H$ domain having an amino acid sequence represented by SEQ ID NO: 111 and a $V_L$ domain having an amino acid sequence represented by SEQ ID NO:

119; a $V_H$ domain having an amino acid sequence represented by SEQ ID NO: 111 and a $V_L$ domain having an amino acid sequence represented by SEQ ID NO: 120; a $V_H$ domain having an amino acid sequence represented by SEQ ID NO: 111 and a $V_L$ domain having an amino acid sequence represented by SEQ ID NO: 121; a $V_H$ domain having an amino acid sequence represented by SEQ ID NO: 112 and a $V_L$ domain having an amino acid sequence represented by SEQ ID NO: 116; a $V_H$ domain having an amino acid sequence represented by SEQ ID NO: 112 and a $V_L$ domain having an amino acid sequence represented by SEQ ID NO: 117; a $V_H$ domain having an amino acid sequence represented by SEQ ID NO: 112 and a $V_L$ domain having an amino acid sequence represented by SEQ ID NO: 118; a $V_H$ domain having an amino acid sequence represented by SEQ ID NO: 112 and a $V_L$ domain having an amino acid sequence represented by SEQ ID NO: 119; a $V_H$ domain having an amino acid sequence represented by SEQ ID NO: 112 and a $V_L$ domain having an amino acid sequence represented by SEQ ID NO: 120; a $V_H$ domain having an amino acid sequence represented by SEQ ID NO: 112 and a $V_L$ domain having an amino acid sequence represented by SEQ ID NO: 121; a $V_H$ domain having an amino acid sequence represented by SEQ ID NO: 113 and a $V_L$ domain having an amino acid sequence represented by SEQ ID NO: 116; a $V_H$ domain having an amino acid sequence represented by SEQ ID NO: 113 and a $V_L$ domain having an amino acid sequence represented by SEQ ID NO: 117; a $V_H$ domain having an amino acid sequence represented by SEQ ID NO: 113 and a $V_L$ domain having an amino acid sequence represented by SEQ ID NO: 118; a $V_H$ domain having an amino acid sequence represented by SEQ ID NO: 113 and a $V_L$ domain having an amino acid sequence represented by SEQ ID NO: 119; a $V_H$ domain having an amino acid sequence represented by SEQ ID NO: 113 and a $V_L$ domain having an amino acid sequence represented by SEQ ID NO: 120; a $V_H$ domain having an amino acid sequence represented by SEQ ID NO: 113 and a $V_L$ domain having an amino acid sequence represented by SEQ ID NO: 121; a $V_H$ domain having an amino acid sequence represented by SEQ ID NO: 114 and a $V_L$ domain having an amino acid sequence represented by SEQ ID NO: 116; a $V_H$ domain having an amino acid sequence represented by SEQ ID NO: 114 and a $V_L$ domain having an amino acid sequence represented by SEQ ID NO: 117; a $V_H$ domain having an amino acid sequence represented by SEQ ID NO: 114 and a $V_L$ domain having an amino acid sequence represented by SEQ ID NO: 118; a $V_H$ domain having an amino acid sequence represented by SEQ ID NO: 114 and a $V_L$ domain having an amino acid sequence represented by SEQ ID NO: 119; a $V_H$ domain having an amino acid sequence represented by SEQ ID NO: 114 and a $V_L$ domain having an amino acid sequence represented by SEQ ID NO: 120; a $V_H$ domain having an amino acid sequence represented by SEQ ID NO: 114 and a $V_L$ domain having an amino acid sequence represented by SEQ ID NO: 121; a $V_H$ domain having an amino acid sequence represented by SEQ ID NO: 115 and a $V_L$ domain having an amino acid sequence represented by SEQ ID NO: 116; a $V_H$ domain having an amino acid sequence represented by SEQ ID NO: 115 and a $V_L$ domain having an amino acid sequence represented by SEQ ID NO: 117; a $V_H$ domain having an amino acid sequence represented by SEQ ID NO: 115 and a $V_L$ domain having an amino acid sequence represented by SEQ ID NO: 118; a $V_H$ domain having an amino acid sequence represented by SEQ ID NO: 115 and a $V_L$ domain having an amino acid sequence represented by SEQ ID NO: 119; a $V_H$ domain having an amino acid sequence represented by SEQ ID NO: 115 and a $V_L$ domain having an amino acid sequence represented by SEQ ID NO: 120; or a $V_H$ domain having an amino acid sequence represented by SEQ ID NO: 115 and a $V_L$ domain having an amino acid sequence represented by SEQ ID NO: 121.

TABLE 6

Amino Acid Sequences of VH and VL Chains

| $V_H$ chain (including CDRs 1-3 and FRs 1-4) | $V_L$ chain (including CDRs 1-3 and FRs 1-4) |
|---|---|
| QVQLQQPGAELVKPGASVKLSCKAS**GYT**<br>**FTSYWMH**WVKQRPGQGLEWIG**MIHPNS**<br>**GSTNYNEKFKS**KATLTVDKSSSTAYMQL<br>SSLTSEDSAVYYCAR**GGYFDY**WGQGTT<br>LTVSS<br>(SEQ ID NO: 110) | DIVMTQSQKFMSTSVGDRVSVTC**KASQ**<br>**NVGTNVA**WYQQKPGQSPKALIY**SASYR**<br>**YS**GVPDRFTGSGSGTDFTLTISNVQSED<br>LAEYFC**QQYNSYPYT**FGGGTKLEIKR<br>(SEQ ID NO: 116) |
| QVQLQQPGAELVKPGASVKLSCKAS**GYT**<br>**FTSYWMH**WVKQRPGQGLEWIG**MIHPNS**<br>**GSTNYNEKFKS**KATLTVDKSSSTAYMQL<br>SSLTSEDSAVYYC**ARESRQLDY**WGQGT<br>TLTVSS<br>(SEQ ID NO: 111) | QIVLTQSPAIMSASPGEKVTMTC**SASSSI**<br>**SYMH**WYQQKPGTSPKRWIY**DTSKLAS**G<br>VPARFSGSGSGTSYSLTISSMEAEDAAT<br>YYC**HQRSSYPLT**FGAGTKLELK<br>(SEQ ID NO: 117) |
| QVQLQQPGAELVKPGASVKLSCKAS**GYT**<br>**FTNYWMH**WVKQRPGQGLEWIG**MIHPNS**<br>**GSTNYNEKFKS**KATLTVDKSSSTAYMQL<br>SSLTSEDSAVYYCAR**RGDGDY**WGQGTT<br>LTVSS<br>(SEQ ID NO: 112) | DIQMTRHPSSLSASMGERVSLTC**RASQE**<br>**ISGYLS**WLQQKPDGTIKRLIY**AASTLDS**G<br>VPKRFSGSRSGSDYSLTISSLESEDFADY<br>YC**LQYASYPYT**FGGGTKLEI<br>(SEQ ID NO: 118) |
| QVQLQQPGAELVKPGASVKMSCKAS**GY**<br>**TFTSYWIT**WVKQRPGQGLEWIG**DIYPGS**<br>**GSTNYNEKFKS**KATLTVDTSSSTAYMQL<br>SSLTSEDSAVYYC**ARGGTRFSPFAY**WG<br>QGTLVTVSAA<br>(SEQ ID NO: 113) | DVLMTQTPLSLPVSLGDQASISC**RSSQSI**<br>**VHSNGNTYLE**WYLQKPGQSPKLLIY**KVS**<br>**NRFS**GVPDRFSGSGSGTDFTLKISRVEA<br>EDLGVYYC**FQGSHVPWT**FGGGTKLEIKR<br>ADA<br>(SEQ ID NO: 119) |

TABLE 6-continued

Amino Acid Sequences of VH and VL Chains

| $V_H$ chain (including CDRs 1-3 and FRs 1-4) | $V_L$ chain (including CDRs 1-3 and FRs 1-4) |
|---|---|
| QVQLQQPGAELVKPGASVKLSCKAS**GYTFTSYWMH**WVKQRPGQGLEWIG**MIHPNSGSTNYNEKFKS**KATLTVDKSSSTAYMQLSSLTSEDSAVYYCARYYYGSSYAMDYWGQGTSVTVS (SEQ ID NO: 114) | QIVLTQSPAIMSASPGEKVTITC**SASSSVSYMH**WFQQKPGTSPKLWIY**STSNLAS**GVPARFSGSGSGTSYSLTISRMEAEDAATYYC**QQRSSYPYT**FGGGTKLEIKRAD (SEQ ID NO: 120) |
| QVQLQQPGAELVKPGASVKLSCKAS**GYTFTSYWMH**WVKQRPGQGLEWIG**MIHPNSGSTNYNEKFKS**KATLTVDKSSSTAYMQLSSLTSEDSAVYYCAN**YYGTNV**WGTGTTVTVS (SEQ ID NO: 115) | DIVLTQSPASLAVSLGQRATISYRAS**KSVSTSGYSYMH**WNQQKPGQPPRLLIY**LVSNLES**GVPARFSGSGSGTDFTLNIHPVEEEDAATYYC**QHIREAYT**FGRGDQSWK (SEQ ID NO: 121) |

Uses

The present disclosure also provides methods for treating a disease or condition, wherein the methods comprise administering to a subject in need thereof an effective amount of a host cell, composition, or unit dose of the present disclosure, wherein the disease or condition expresses or is otherwise associated with the antigen that is specifically bound by the CAR. In certain embodiments, the disease or condition is a hyperproliferative or proliferative disease, such as a cancer, an autoimmune disease, or an infectious disease (e.g., viral, bacterial, fungal, or parasitic).

Subjects that can be treated by the present invention are, in general, human and other primate subjects, such as monkeys and apes for veterinary medicine purposes. In any of the aforementioned embodiments, the subject may be a human subject. The subjects can be male or female and can be any suitable age, including infant, juvenile, adolescent, adult, and geriatric subjects. Cells according to the present disclosure may be administered in a manner appropriate to the disease, condition, or disorder to be treated as determined by persons skilled in the medical art. In any of the above embodiments, a cell comprising a CAR as described herein is administered intravenously, intraperitoneally, intratumorally, into the bone marrow, into a lymph node, or into the cerebrospinal fluid so as to encounter the target antigen or cells. An appropriate dose, suitable duration, and frequency of administration of the compositions will be determined by such factors as a condition of the patient; size, type, and severity of the disease, condition, or disorder; the undesired type or level or activity of the tagged cells, the particular form of the active ingredient; and the method of administration.

In any of the above embodiments, methods of the present disclosure comprise administering a host cell expressing a CAR of the present disclosure, or a composition comprising the host cell. The amount of cells in a composition is at least one cell (for example, one CAR-modified CD8+ T cell subpopulation; one CAR-modified CD4+ T cell subpopulation; one CAR-modified NK cell subpopulation) or is more typically greater than $10^2$ cells, for example, up to $10^6$, up to $10^7$, up to $10^8$ cells, up to $10^9$ cells, or $10^{10}$ cells or more, such as about $10^{11}$ cells/m$^2$. In certain embodiments, the cells are administered in a range from about $10^5$ to about $10^{11}$ cells/m$^2$, preferably in a range of about $10^5$ or about $10^6$ to about 109 or about $10^{10}$ cells/m$^2$. The number of cells will depend upon the ultimate use for which the composition is intended as well as the type of cells included therein. For example, cells modified to contain a CAR specific for a particular antigen will comprise a cell population containing at least 30%, 35%, 40%, 45%, 50%, 55%, 60%, 65%, 70%, 75%, 80%, 85%, 90%, 95% or more of such cells. For uses provided herein, cells are generally in a volume of a liter or less, 500 mLs or less, 250 mLs or less, or 100 mLs or less. In embodiments, the density of the desired cells is typically greater than $10^4$ cells/mL and generally is greater than $10^7$ cells/mL, generally $10^8$ cells/mL or greater. The cells may be administered as a single infusion or in multiple infusions over a range of time. A clinically relevant number of immune cells can be apportioned into multiple infusions that cumulatively equal or exceed $10^6$, $10^7$, $\mathbf{10^8}$, $10^9$, $\mathbf{10^{10}}$, or $10^{11}$ cells. In any of the presently disclosed embodiments, the host cell is an allogeneic cell, a syngeneic cell, or an autologous cell.

Unit doses are also provided herein which comprise a host cell (e.g., a modified immune cell comprising a polynucleotide of the present disclosure) or host cell composition of this disclosure. In some embodiments, a unit dose comprises (i) a composition comprising at least about 50% modified CD4+ T cells, combined with (ii) a composition comprising at least about 50% modified CD8+ T cells, in about a 1:1 ratio, wherein the unit dose contains a reduced amount or substantially no naïve T cells.

Also contemplated are pharmaceutical compositions that comprise cells expressing the CARs as disclosed herein and a pharmaceutically acceptable carrier, diluents, or excipient. Suitable excipients include water, saline, dextrose, glycerol, or the like and combinations thereof. In embodiments, compositions comprising host cells as disclosed herein further comprise a suitable infusion media.

Pharmaceutical compositions may be administered in a manner appropriate to the disease or condition to be treated (or prevented) as determined by persons skilled in the medical art. An appropriate dose and a suitable duration and frequency of administration of the compositions will be determined by such factors as the health condition of the patient, size of the patient (i.e., weight, mass, or body area), the type and severity of the patient's condition, the undesired type or level or activity of the tagged cells, the particular form of the active ingredient, and the method of administration. In general, an appropriate dose and treatment regimen provide the composition(s) in an amount sufficient to provide therapeutic and/or prophylactic benefit (such as described herein, including an improved clinical outcome, such as more frequent complete or partial remissions, or longer disease-free and/or overall survival, or a lessening of symptom severity). For prophylactic use, a dose should be sufficient to prevent, delay the onset of, or diminish the severity of a disease associated with disease or disorder. Prophylactic benefit of the immunogenic compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

Certain methods of treatment or prevention contemplated herein include administering a host cell (which may be autologous, allogeneic or syngeneic) comprising a desired polynucleotide as described herein that is stably integrated into the chromosome of the cell. For example, such a cellular composition may be generated ex vivo using autologous, allogeneic or syngeneic immune system cells (e.g., T cells, antigen-presenting cells, NK cells) in order to administer a desired, CAR-expressing T-cell composition to a subject as an adoptive immunotherapy. In certain embodiments, the host cell is a hematopoietic progenitor cell or a human immune cell. In certain embodiments, the immune system cell is a CD4+ T cell, a CD8+ T cell, a CD4− CD8− double-negative T cell, an NK cell, or any combination thereof. In certain embodiments, the immune system cell is a naïve T cell, a central memory T cell, a stem cell memory T cell, an effector memory T cell, an NK cell, or any combination thereof. In particular embodiments, the cell is a CD4+ T cell. In particular embodiments, the cell is a CD8+ T cell. In particular embodiments, the cell is an NK cell.

As used herein, administration of a composition refers to delivering the same to a subject, regardless of the route or mode of delivery. Administration may be affected continuously or intermittently, and parenterally. Administration may be for treating a subject already confirmed as having a recognized condition, disease or disease state, or for treating a subject susceptible to or at risk of developing such a condition, disease or disease state. Co-administration with an adjunctive therapy may include simultaneous and/or sequential delivery of multiple agents in any order and on any dosing schedule (e.g., CAR-expressing recombinant (i.e., engineered) host cells with one or more cytokines; immunosuppressive therapy such as calcineurin inhibitors, corticosteroids, microtubule inhibitors, low dose of a mycophenolic acid prodrug, or any combination thereof).

In certain embodiments, a plurality of doses of a recombinant host cell as described herein is administered to the subject, which may be administered at intervals between administrations of about two to about four weeks.

In still further embodiments, the subject being treated is further receiving immunosuppressive therapy, such as calcineurin inhibitors, corticosteroids, microtubule inhibitors, low dose of a mycophenolic acid prodrug, or any combination thereof. In yet further embodiments, the subject being treated has received a non-myeloablative or a myeloablative hematopoietic cell transplant, wherein the treatment may be administered at least two to at least three months after the non-myeloablative hematopoietic cell transplant.

An effective amount of a pharmaceutical composition (e.g., host cell, CAR, unit dose, or composition) refers to an amount sufficient, at dosages and for periods of time needed, to achieve the desired clinical results or beneficial treatment, as described herein. An effective amount may be delivered in one or more administrations.

Methods according to this disclosure may further include administering one or more additional agents to treat the disease or disorder in a combination therapy. For example, in certain embodiments, a combination therapy comprises administering a CAR (or an engineered host cell expressing the same) with (concurrently, simultaneously, or sequentially) an immune checkpoint inhibitor. In some embodiments, a combination therapy comprises administering CAR of the present disclosure (or an engineered host cell expressing the same) with an agonist of a stimulatory immune checkpoint agent. In further embodiments, a combination therapy comprises administering a CAR of the present disclosure (or an engineered host cell expressing the same) with a secondary therapy, such as chemotherapeutic agent, a radiation therapy, a surgery, an antibody, or any combination thereof.

Cytokines are used to manipulate host immune response towards anticancer activity (see, e.g., Floros & Tarhini, 2015). Cytokines useful for promoting immune anticancer or antitumor response include, for example, IFN-α, IL-2, IL-3, IL-4, IL-10, IL-12, IL-13, IL-15, IL-16, IL-17, IL-18, IL-21, IL-24, and GM-CSF, singly or in any combination with the binding proteins or cells expressing the same of this disclosure.

Various embodiments of the technology are described above. It will be appreciated that details set forth above are provided to describe the embodiments in a manner sufficient to enable a person skilled in the relevant art to make and use the disclosed embodiments. Several of the details and advantages, however, may not be necessary to practice some embodiments. Additionally, some well-known structures or functions may not be shown or described in detail, so as to avoid unnecessarily obscuring the relevant description of the various embodiments. Although some embodiments may be within the scope of the technology, they may not be described in detail with respect to the Figures. Furthermore, features, structures, or characteristics of various embodiments may be combined in any suitable manner. Moreover, one skilled in the art will recognize that there are a number of other technologies that could be used to perform functions similar to those described above. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel or may be performed at different times. The headings provided herein are for convenience only and do not interpret the scope or meaning of the described technology.

Any patents, applications and other references cited herein are incorporated herein by reference. Aspects of the described technology can be modified, if necessary, to employ the systems, functions, and concepts of the various references described above to provide yet further embodiments.

These and other changes can be made in light of the above Detailed Description. While the above description details certain embodiments and describes the best mode contemplated, no matter how detailed, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated.

The foregoing is merely intended to illustrate various embodiments of the present invention. The specific modifications discussed above are not to be construed as limitations on the scope of the invention. It will be apparent to one skilled in the art that various equivalents, changes, and modifications may be made without departing from the scope of the invention, and it is understood that such equivalent embodiments are to be included herein. All references cited herein are incorporated by reference as if fully set forth herein.

EXAMPLES

The following examples are illustrative of several embodiments of the present technology:

Example 1: Generation of and Characterization of B7-H3 Monoclonal Antibodies In this example, anti-B7-H3 monoclonal antibodies (mAbs) were generated, functionally tested, and sequenced. Portions of the $V_L$ and $V_H$ chains for each mAb were used to generate the CARs described in Example 2.

Generation of anti-B7-H3 mAbs. The functional domain for B7-H3 is IgV. Accordingly, a human B7-H3 IgV-Ig protein was generated by fusing the B7-H3 IgV coding region (amino acid residues E35-A139) to a human IgG1 Fc tag from plasmid pMT/BiP as previously described (Zhao, et al., 2013). The protein was expressed in an S2 system as previously described (Zhao, et al., 2013) and then purified. Mice were immunized with B7-H3 IgV-Ig protein and hybridomas were generated using standard techniques from splenocytes fused to NSO myeloma cells as previously described (Zhao, et al., 2013).

Characterizing mAbs 1G5, 15F9, 23B2, 8K12, 12B4, and 24D12. 1G5, 15F9, 81812, 124, and 24D12 are IgG3 mAbs having kappa chains, whereas 23B2 is an IgG1 mAb having a kappa chain. The binding affinities ($K_d$) of mAbs 1G5, 15F9, 231B2, 81B12, 1214, and 24D12 to human B7-H3 and to mouse B7-H3 protein were determined using standard techniques including by Surface Plasmon Resonance (SPM) and are shown in Table 7.

TABLE 7

Kinetic parameters from Surface Plasmon Resonance of various mAbs

| mAb clone | Isotype | Antigen | Kd (nM) |
|---|---|---|---|
| 1G5 | IgG3, K | Human B7-H3 | 4.86 |
| 1G5 | IgG3, K | Mouse B7-H3 | 0.81 |
| 15F9 | IgG3, K | Human B7-H3 | 4.51 |
| 15F9 | IgG3, K | Mouse B7-H3 | 1.76 |
| 23B2 | IgG1, K | Human B7-H3 | 11.08 |
| 23B2 | IgG1, K | Mouse B7-H3 | 10.18 |
| 8B12 | IgG3, K | Human B7-H3 | 0.32 |
| 8B12 | IgG3, K | Mouse B7-H3 | 4.01 |
| 12B4 | IgG3, K | Human B7-H3 | 5.62 |
| 12B4 | IgG3, K | Mouse B7-H3 | 1.71 |
| 24D12 | IgG3, K | Human B7-H3 | 4.51 |
| 24D12 | IgG3, K | Mouse B7-H3 | 1.76 |

Sequencing mAbs 1G5, 15F9, 23B2, 8812, 12B4, and 24D12. The hybridomas 1G5, 15F9, 23B2, 8B12, 12B4, and 24D12 were sequenced using standard techniques. Each hybridoma has a unique $V_H$ sequence and a unique $V_L$ sequence (see SEQ ID NOs: 7-18 of Table 1 for amino acid sequences and SEQ ID NOs: 25-36 of Table 2 for nucleic acid sequences).

Example 2: Generation of and Functional Testing of B7-H3 CAR-T Cells

Generation of B7-H3 CAR-T viral vectors with mAb 1G5, 15F9, 23B2, 8812, 12B4, and 24D12 as scFvs. As shown in FIGS. 1-4, eighteen B7-H3 CAR-T vectors were generated, six for each mAb 1G5, 15F9, 23B2, 8B12, 12B4, or 24D12. Each of the eighteen vectors includes polynucleotides encoding the following polypeptides, schematically from left to right, a IgG1 $V_K$ Leader sequence, a $V_L$ domain (from 1 G5, 15F9, 23B2, 8B12, 12B4, or 24D12), a linker domain, a $V_H$ domain from 1 G5, 15F9, 23B2, 8B12, 12B4, or 24D12), a CD8α hinge and CD8α transmembrane region, a CD28 intracellular tail, a 4-1 BB intracellular tail, and a CD3ζ domain. For all vectors, the mAb sequence used to generate the $V_L$ domain is the same mAb from which the $V_H$ sequence was derived. As shown, the B7-H3 CAR-T vector optionally includes GFP as a transduction marker. In this example, three vectors were generated for 1 G5 (one with EGFRt, one with GFP, and one without), three vectors were generated for 15F9 (one with EGFRt, one with GFP, and one without), three vectors were generated for 23B2 (one with EGFRt, one with GFP, and one without), three vectors were generated for 8B12 (one with EGFRt, one with GFP, and one without), three vectors were generated for 12B4 (one with EGFRt, one with GFP, and one without), and three vectors were generated for 24D12 (one with EGFRt, one with GFP, and one without). These eighteen vectors are illustrated schematically by the two vectors shown in FIGS. 1-4.

Figure 4A:
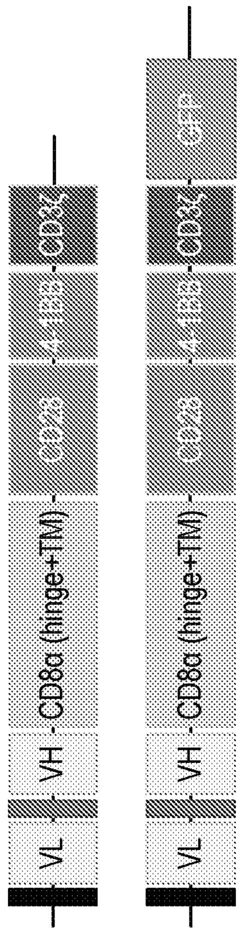
FIG. 4A is a schematic representation of two B7-H3 CARs in accordance with an embodiment of the present disclosure.
Figure 4B:
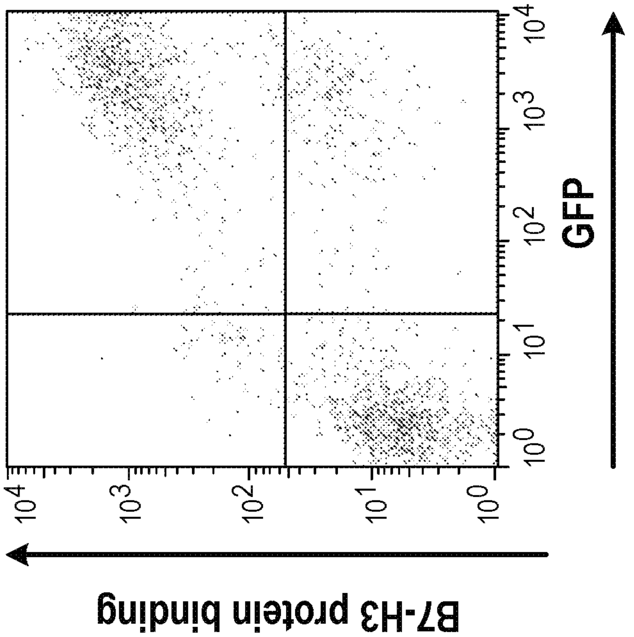
FIG. 4B depicts a representative fluorescence assisted cell sorting (FACS) plot for T cells expressing one of the B7-H3 CARs of FIG. 4A.

Human peripheral blood mononuclear cells (PBMCs) were transduced with each of the nine vectors. CAR positive T cells were sorted from the total PBMC population by fluorescence assisted cell sorting (FACS) since human T cells expressing the B7-H3 CAR illustrated in FIG. 4A were denoted by GFP positive T cells (GFP was used as a transduction marker) (FIG. 4B).

Figure 5:
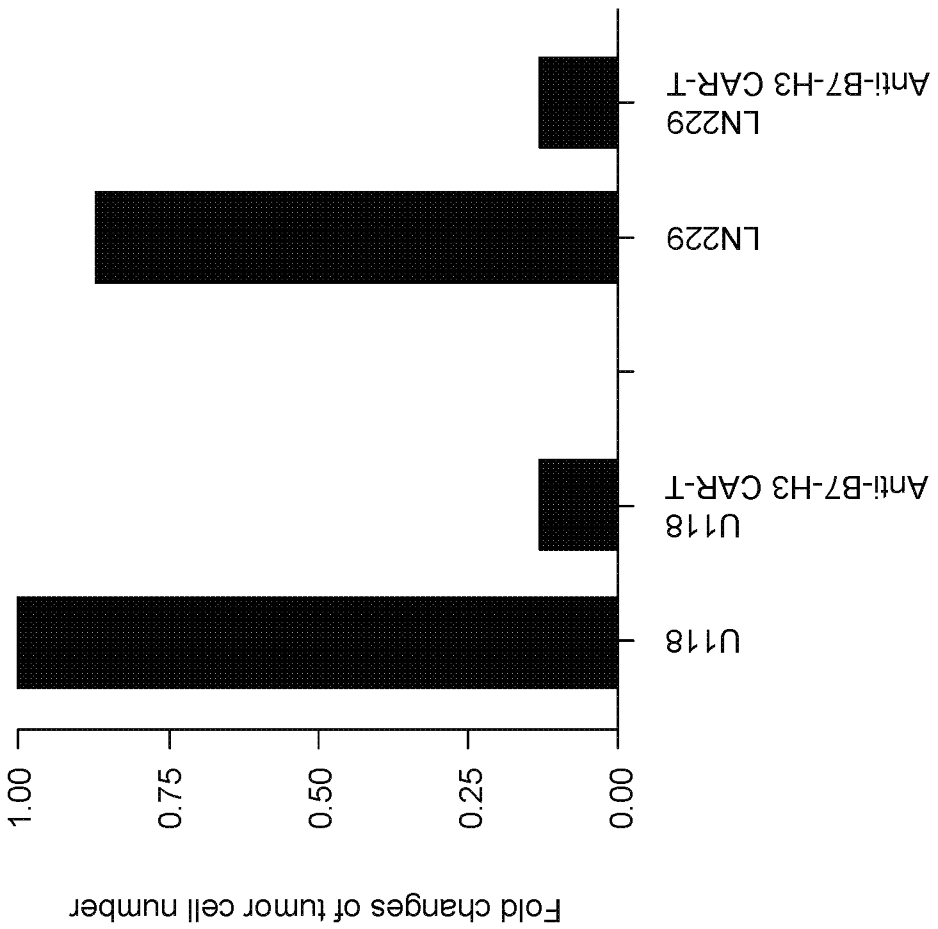
FIG. 5 depicts a representative graph showing that T cells expressing a B7-H3 CAR in accordance with an embodiment of the present disclosure kill at least two different types of tumor cells.

The B7-H3 CAR-T cells were mixed at a 1 to 1 ratio with normal T cells and then co-cultured with glioblastoma U118 and LB229 tumor cells at an effector: target ratio of 1:1. After five days, the co-cultures were analyzed by flow cytometry. The B7-H3 CAR-T cells are functional as they killed the majority of U118 or LB229 tumor cells (FIG. 5).

Example 3: Expression of B7-H3 CAR-T in Human Primary T Cells

Figure 6B:
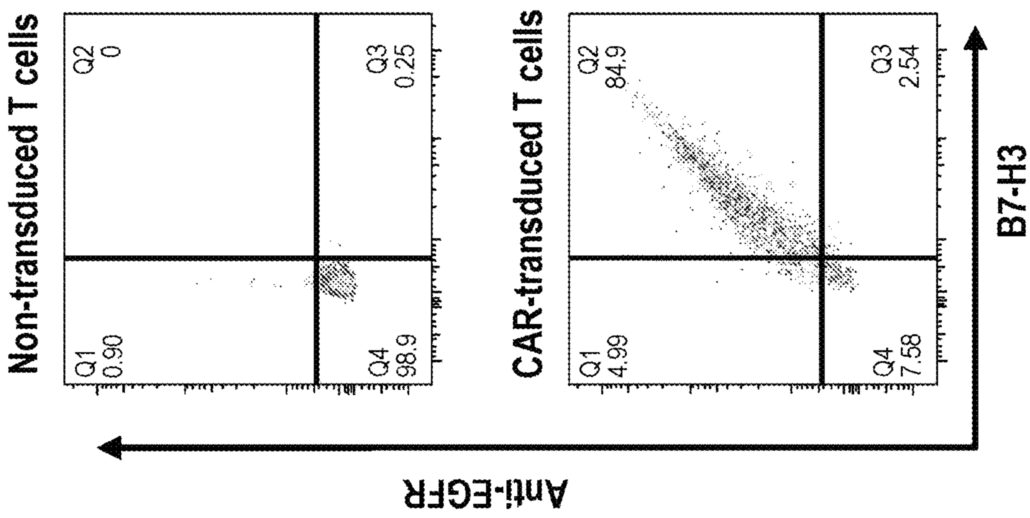
FIG. 6B is FACS showing that anti-B7-H3 CAR-T vector transduced human primary T cells expressed EGFR and recognized B7-H3 antigen. Non-transduced human primary T cells did not express EGFR and did not recognize B7-H3 antigen.
Figure 6A:
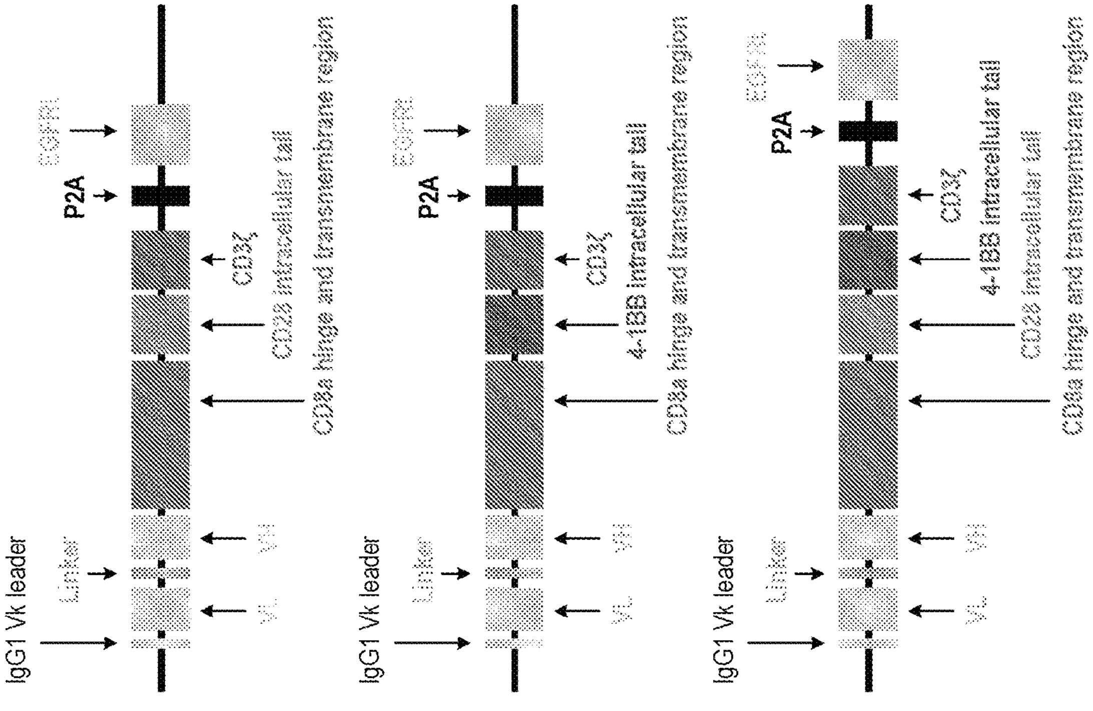
FIG. 6A is a schematic representation of different anti-B7-H3 CAR-T vectors generated from anti-B7-H3 mAbs.

FIG. 6 illustrates that six different anti-B7-H3 CAR-T vectors with six different anti-B7-H3 mAbs (1G5, 15F9, 23B2, 8B12, 12B4, and 24D12) were generated and used to transduce human primary T cells. The transduced human primary T cells expressed EGFR and recognized B7-H3 antigen; whereas non-transduced human primary T cells did not express any EGFR or recognize B7-H3 antigen, as shown by FACS (FIG. 6B).

From the foregoing, it will be appreciated that specific embodiments of the present disclosure have been described herein for purposes of illustration, but that various modifications may be made without deviating from the scope of the present disclosure. Accordingly, the present disclosure is not limited except as by the appended claims.

REFERENCES

1. Baral et al. B7-H3 and B7-H1 expression in cerebral spinal fluid and tumor tissue correlates with the malignancy grade of glioma patients. Oncol Lett 8:1195-1201 (2014)

2. Brentjens et al. Genetically targeted T cells eradicate systemic acute lymphoblastic leukemia xenografts. Clin Cancer Res 13(18 Pt 1):5426-5435 (2007)
3. Chen et al. The coexpression and clinical significance of costimulatory molecules B7-H1, B7-H3, and B7-H4 in human pancreatic cancer. Onco Targets Ther 7:1465-1472 (2014).
4. Dossett et al. Adoptive immunotherapy of disseminated leukemia with TCR-transduced, $CD8^{+}$ T cells expressing a known endogenous TCR. Mol Ther 17(4):742-749 (2009)
5. Floros & Tarhini. Anticancer Cytokines: Biology and Clinical Effects of Interferon-α2, Interleukin (IL)-2, IL-15, IL-21, and IL-12. Semin Oncol 42(4):539-548 (2015)
6. Guest et al. The role of extracellular spacer regions in the optimal design of chimeric immune receptors: evaluation of four different scFvs and antigens. J Immunother 28(3):203-211 (2005)
7. Harris & Kranz. Adoptive T Cell Therapies: A Comparison of T Cell Receptors and Chimeric Antigen Receptors. Trends Pharmacol Sci 37(3):220-230 (2016)
8. Hu et al. Expression of costimulatory molecule B7-H3 and its prognostic implications in human acute leukemia. Hematology 20:187-195 (2015)
9. Ingebrigtsen et al. B7-H3 expression in colorectal cancer: associations with clinicopathological parameters and patient outcome. BMC Cancer 14:602 (2014).
10. Kuball et al. Facilitating matched pairing and expression of TCR chains introduced into human T cells. Blood 109(6):2331-2338 (2007)
11. Leen et al. Improving T cell therapy for cancer. Annu Rev Immunol 25:243-265 (2007)
12. Patel et al. Impact of chimeric immune receptor extracellular protein domains on T cell function. Gene Therapy 6(3):412-419 (1999)
13. Picarda et al. Molecular Pathways: Targeting B7-H3 (CD276) for Human Cancer Immunotherapy. Clin Cancer Res 22:3425-3431 (2016)
14. Qin et al. B7-H3 is a new cancer-specific endothelial marker in clear cell renal cell carcinoma. Onco Targets Ther 6:1667-1673 (2013)
15. Sadelain et al. The basic principles of chimeric antigen receptor design. Cancer Discov 3(4):388-398 (2013)
16. Scatchard et al. The attractions of proteins for small molecules and ions. Ann. N.Y. Acad. Sci. 51:660 (1949)
16. Schmitt et al. T cell receptor gene therapy for cancer. Hum Gene Ther 20(11):1240-1248 (2009)
17. Scholten et al. Codon modification of T cell receptors allows enhanced functional expression in transgenic human T cells. Clin Immunol 119(2):135-145 (2006)
18. Stone et al. A novel T cell receptor single-chain signaling complex mediates antigen-specific T cell activity and tumor control. Cancer Immunol Immunother 63(11):1163-1176 (2014)
19. Sun et al. B7-H3 and B7-H4 expression in non-small-cell lung cancer. Lung Cancer 53:143-151 (2006)
20. Sun et al. B7-H3 is expressed in human hepatocellular carcinoma and is associated with tumor aggressiveness and postoperative recurrence. Cancer Immunol Immunother 61:2171-2182 (2012)
21. Sun et al. B7-H3 expression in breast cancer and upregulation of VEGF through gene silence. Onco Targets Ther 7:1979-1986 (2014)
22. Till et al. Adoptive immunotherapy for indolent non-Hodgkin lymphoma and mantle cell lymphoma using genetically modified autologous CD20-specific T cells. Blood 112(6):2261-2271 (2008)
23. Vigdorovich et al. Structure and T cell inhibition properties of B7 family member, B7-H3. Structure 21:707-717 (2013)
24. Walseng et al. A TCR-based Chimeric Antigen Receptor. Sci Rep 7(1):10713 (2017)
25. Wang et al. Optimizing adoptive polyclonal T cell immunotherapy of lymphomas, using a chimeric T cell receptor possessing CD28 and CD137 costimulatory domains. Hum Gene Ther 18:712-725 (2007)
26. Wang et al. B7-H3 associated with tumor progression and epigenetic regulatory activity in cutaneous melanoma. J Invest Dermatol 133:2050-2058 (2013)
27. Wang et al. B7-H3 is overexpressed in patients suffering osteosarcoma and associated with tumor aggressiveness and metastasis. PLoS One 8:e70689 (2013)
28. Wilson. Tech. Sight. Analyzing biomolecular interactions. Science 295(5562):2103-2105 (2002)
29. Wolff et al. Monoclonal antibody homodimers: enhanced antitumor activity in nude mice. Cancer Res 53(11):2560-2565 (1993)
30. Xylinas et al. Association of T-cell co-regulatory protein expression with clinical outcomes following radical cystectomy for urothelial carcinoma of the bladder. Eur J Surg Oncol 40:121-127 (2014)
31. Zang & Allison. The B7 family and cancer therapy: costimulation and coinhibition. Clin Cancer Res 13:5271-5279 (2007)
32. Zang et al. B7-H3 and B7x are highly expressed in human prostate cancer and associated with disease spread and poor outcome. Proc Natl Acad Sci USA 104:19458-19463 (2007)
33. Zang et al. Tumor associated endothelial expression of B7-H3 predicts survival in ovarian carcinomas. Mod Pathol 23:1104-1112 (2010)
34. Zhao et al. HHLA2 is a member of the B7 family and inhibits human CD4 and CD8 T-cell function. Proc Natl Acad Sci USA 110:9879-9884 (2013)

TABLE 8

| Amino Acid Sequences of CDRs | | |
|---|---|---|
| $V_H$ CDR Sequences | | |
| CDR1 | CDR2 | CDR3 |
| GYTFTSYWMH (SEQ ID NO: 37) | MIHPNSGSTNYNEKFKS (SEQ ID NO: 46) | GGYFDY (SEQ ID NO: 54) |
| GYTFTSYWMH (SEQ ID NO: 37) | MIHPNSGSTNYNEKFKS (SEQ ID NO: 46) | ARESRQLDY (SEQ ID NO: 55) |
| GYTFTSYWMH (SEQ ID NO: 37) | MIHPNSGSTNYNEKFKS (SEQ ID NO: 46) | RGDGDY (SEQ ID NO: 56) |
| GYTFTSYWMH (SEQ ID NO: 37) | MIHPNSGSTNYNEKFKS (SEQ ID NO: 46) | ARGGTRFSPFAY (SEQ ID NO: 57) |
| GYTFTSYWMH (SEQ ID NO: 37) | MIHPNSGSTNYNEKFKS (SEQ ID NO: 46) | YYYGSSYAMDY (SEQ ID NO: 58) |
| GYTFTSYWMH (SEQ ID NO: 37) | MIHPNSGSTNYNEKFKS (SEQ ID NO: 46) | YYGTNV (SEQ ID NO: 59) |
| GYTFTSYWMH (SEQ ID NO: 37) | DIYPGSGSTNYNEKFKS (SEQ ID NO: 47) | GGYFDY (SEQ ID NO: 54) |
| GYTFTSYWMH (SEQ ID NO: 37) | DIYPGSGSTNYNEKFKS (SEQ ID NO: 47) | ARESRQLDY (SEQ ID NO: 55) |

TABLE 8-continued

| Amino Acid Sequences of CDRs | | |
|---|---|---|
| GYTFTSYWMH (SEQ ID NO: 37) | DIYPGSGSTNYNEKFKS (SEQ ID NO: 47) | RGDGDY (SEQ ID NO: 56) |
| GYTFTSYWMH (SEQ ID NO: 37) | DIYPGSGSTNYNEKFKS (SEQ ID NO: 47) | ARGGTRFSPFAY (SEQ ID NO: 57) |
| GYTFTSYWMH (SEQ ID NO: 37) | DIYPGSGSTNYNEKFKS (SEQ ID NO: 47) | YYYGSSYAMDY (SEQ ID NO: 58) |
| GYTFTSYWMH (SEQ ID NO: 37) | DIYPGSGSTNYNEKFKS (SEQ ID NO: 47) | YYGTNV (SEQ ID NO: 59) |
| GYTFTNYWMH (SEQ ID NO: 38) | MIHPNSGSTNYNEKFKS (SEQ ID NO: 46) | GGYFDY (SEQ ID NO: 54) |
| GYTFTNYWMH (SEQ ID NO: 38) | MIHPNSGSTNYNEKFKS (SEQ ID NO: 46) | ARESRQLDY (SEQ ID NO: 55) |
| GYTFTNYWMH (SEQ ID NO: 38) | MIHPNSGSTNYNEKFKS (SEQ ID NO: 46) | RGDGDY (SEQ ID NO: 56) |
| GYTFTNYWMH (SEQ ID NO: 38) | MIHPNSGSTNYNEKFKS (SEQ ID NO: 46) | ARGGTRFSPFAY (SEQ ID NO: 57) |
| GYTFTNYWMH (SEQ ID NO: 38) | MIHPNSGSTNYNEKFKS (SEQ ID NO: 46) | YYYGSSYAMDY (SEQ ID NO: 58) |
| GYTFTNYWMH (SEQ ID NO: 38) | MIHPNSGSTNYNEKFKS (SEQ ID NO: 46) | YYGTNV (SEQ ID NO: 59) |
| GYTFTNYWMH (SEQ ID NO: 38) | DIYPGSGSTNYNEKFKS (SEQ ID NO: 47) | GGYFDY (SEQ ID NO: 54) |
| GYTFTNYWMH (SEQ ID NO: 38) | DIYPGSGSTNYNEKFKS (SEQ ID NO: 47) | ARESRQLDY (SEQ ID NO: 55) |
| GYTFTNYWMH (SEQ ID NO: 38) | DIYPGSGSTNYNEKFKS (SEQ ID NO: 47) | RGDGDY (SEQ ID NO: 56) |
| GYTFTNYWMH (SEQ ID NO: 38) | DIYPGSGSTNYNEKFKS (SEQ ID NO: 47) | ARGGTRFSPFAY (SEQ ID NO: 57) |
| GYTFTNYWMH (SEQ ID NO: 38) | DIYPGSGSTNYNEKFKS (SEQ ID NO: 47) | YYYGSSYAMDY (SEQ ID NO: 58) |
| GYTFTNYWMH (SEQ ID NO: 38) | DIYPGSGSTNYNEKFKS (SEQ ID NO: 47) | YYGTNV (SEQ ID NO: 59) |
| GYTFTSYWIT (SEQ ID NO: 39) | MIHPNSGSTNYNEKFKS (SEQ ID NO: 46) | GGYFDY (SEQ ID NO: 54) |
| GYTFTSYWIT (SEQ ID NO: 39) | MIHPNSGSTNYNEKFKS (SEQ ID NO: 46) | ARESRQLDY (SEQ ID NO: 55) |
| GYTFTSYWIT (SEQ ID NO: 39) | MIHPNSGSTNYNEKFKS (SEQ ID NO: 46) | RGDGDY (SEQ ID NO: 56) |
| GYTFTSYWIT (SEQ ID NO: 39) | MIHPNSGSTNYNEKFKS (SEQ ID NO: 46) | ARGGTRFSPFAY (SEQ ID NO: 57) |
| GYTFTSYWIT (SEQ ID NO: 39) | MIHPNSGSTNYNEKFKS (SEQ ID NO: 46) | YYYGSSYAMDY (SEQ ID NO: 58) |
| GYTFTSYWIT (SEQ ID NO: 39) | MIHPNSGSTNYNEKFKS (SEQ ID NO: 46) | YYGTNV (SEQ ID NO: 59) |
| GYTFTSYWIT (SEQ ID NO: 39) | DIYPGSGSTNYNEKFKS (SEQ ID NO: 47) | GGYFDY (SEQ ID NO: 54) |
| GYTFTSYWIT (SEQ ID NO: 39) | DIYPGSGSTNYNEKFKS (SEQ ID NO: 47) | ARESRQLDY (SEQ ID NO: 55) |
| GYTFTSYWIT (SEQ ID NO: 39) | DIYPGSGSTNYNEKFKS (SEQ ID NO: 47) | RGDGDY (SEQ ID NO: 56) |
| GYTFTSYWIT (SEQ ID NO: 39) | DIYPGSGSTNYNEKFKS (SEQ ID NO: 47) | ARGGTRFSPFAY (SEQ ID NO: 57) |

TABLE 8-continued

| Amino Acid Sequences of CDRs | | |
|---|---|---|
| GYTFTSYWIT (SEQ ID NO: 39) | DIYPGSGSTNYNEKFKS (SEQ ID NO: 47) | YYYGSSYAMDY (SEQ ID NO: 58) |
| GYTFTSYWIT (SEQ ID NO: 39) | DIYPGSGSTNYNEKFKS (SEQ ID NO: 47) | YYGTNV (SEQ ID NO: 59) |
| $V_L$ CDR Sequences | | |
| CDR1 | CDR2 | CDR3 |
| KASQNVGTNVA (SEQ ID NO: 40) | SASYRYS (SEQ ID NO: 48) | QQYNSYPYT (SEQ ID NO: 60) |
| KASQNVGTNVA (SEQ ID NO: 40) | SASYRYS (SEQ ID NO: 48) | HQRSSYPLT (SEQ ID NO: 61) |
| KASQNVGTNVA (SEQ ID NO: 40) | SASYRYS (SEQ ID NO: 48) | LQYASYPYT (SEQ ID NO: 62) |
| KASQNVGTNVA (SEQ ID NO: 40) | SASYRYS (SEQ ID NO: 48) | FQGSHVPWT (SEQ ID NO: 63) |
| KASQNVGTNVA (SEQ ID NO: 40) | SASYRYS (SEQ ID NO: 48) | QQRSSYPYT (SEQ ID NO: 64) |
| KASQNVGTNVA (SEQ ID NO: 40) | SASYRYS (SEQ ID NO: 48) | QHIREAYT (SEQ ID NO: 65) |
| KASQNVGTNVA (SEQ ID NO: 40) | DTSKLAS (SEQ ID NO: 49) | QQYNSYPYT (SEQ ID NO: 60) |
| KASQNVGTNVA (SEQ ID NO: 40) | DTSKLAS (SEQ ID NO: 49) | HQRSSYPLT (SEQ ID NO: 61) |
| KASQNVGTNVA (SEQ ID NO: 40) | DTSKLAS (SEQ ID NO: 49) | LQYASYPYT (SEQ ID NO: 62) |
| KASQNVGTNVA (SEQ ID NO: 40) | DTSKLAS (SEQ ID NO: 49) | FQGSHVPWT (SEQ ID NO: 63) |
| KASQNVGTNVA (SEQ ID NO: 40) | DTSKLAS (SEQ ID NO: 49) | QQRSSYPYT (SEQ ID NO: 64) |
| KASQNVGTNVA (SEQ ID NO: 40) | DTSKLAS (SEQ ID NO: 49) | QHIREAYT (SEQ ID NO: 65) |
| KASQNVGTNVA (SEQ ID NO: 40) | AASTLDS (SEQ ID NO: 50) | QQYNSYPYT (SEQ ID NO: 60) |
| KASQNVGTNVA (SEQ ID NO: 40) | AASTLDS (SEQ ID NO: 50) | HQRSSYPLT (SEQ ID NO: 61) |
| KASQNVGTNVA (SEQ ID NO: 40) | AASTLDS (SEQ ID NO: 50) | LQYASYPYT (SEQ ID NO: 62) |
| KASQNVGTNVA (SEQ ID NO: 40) | AASTLDS (SEQ ID NO: 50) | FQGSHVPWT (SEQ ID NO: 63) |
| KASQNVGTNVA (SEQ ID NO: 40) | AASTLDS (SEQ ID NO: 50) | QQRSSYPYT (SEQ ID NO: 64) |
| KASQNVGTNVA (SEQ ID NO: 40) | AASTLDS (SEQ ID NO: 50) | QHIREAYT (SEQ ID NO: 65) |
| KASQNVGTNVA (SEQ ID NO: 40) | KVSNRFS (SEQ ID NO: 51) | QQYNSYPYT (SEQ ID NO: 60) |
| KASQNVGTNVA (SEQ ID NO: 40) | KVSNRFS (SEQ ID NO: 51) | HQRSSYPLT (SEQ ID NO: 61) |
| KASQNVGTNVA (SEQ ID NO: 40) | KVSNRFS (SEQ ID NO: 51) | LQYASYPYT (SEQ ID NO: 62) |
| KASQNVGTNVA (SEQ ID NO: 40) | KVSNRFS (SEQ ID NO: 51) | FQGSHVPWT (SEQ ID NO: 63) |

TABLE 8-continued

| Amino Acid Sequences of CDRs | | |
|---|---|---|
| KASQNVGTNVA (SEQ ID NO: 40) | KVSNRFS (SEQ ID NO: 51) | QQRSSYPYT (SEQ ID NO: 64) |
| KASQNVGTNVA (SEQ ID NO: 40) | KVSNRFS (SEQ ID NO: 51) | QHIREAYT (SEQ ID NO: 65) |
| KASQNVGTNVA (SEQ ID NO: 40) | STSNLAS (SEQ ID NO: 52) | QQYNSYPYT (SEQ ID NO: 60) |
| KASQNVGTNVA (SEQ ID NO: 40) | STSNLAS (SEQ ID NO: 52) | HQRSSYPLT (SEQ ID NO: 61) |
| KASQNVGTNVA (SEQ ID NO: 40) | STSNLAS (SEQ ID NO: 52) | LQYASYPYT (SEQ ID NO: 62) |
| KASQNVGTNVA (SEQ ID NO: 40) | STSNLAS (SEQ ID NO: 52) | FQGSHVPWT (SEQ ID NO: 63) |
| KASQNVGTNVA (SEQ ID NO: 40) | STSNLAS (SEQ ID NO: 52) | QQRSSYPYT (SEQ ID NO: 64) |
| KASQNVGTNVA (SEQ ID NO: 40) | STSNLAS (SEQ ID NO: 52) | QHIREAYT (SEQ ID NO: 65) |
| KASQNVGTNVA (SEQ ID NO: 40) | LVSNLES (SEQ ID NO: 53) | QQYNSYPYT (SEQ ID NO: 60) |
| KASQNVGTNVA (SEQ ID NO: 40) | LVSNLES (SEQ ID NO: 53) | HQRSSYPLT (SEQ ID NO: 61) |
| KASQNVGTNVA (SEQ ID NO: 40) | LVSNLES (SEQ ID NO: 53) | LQYASYPYT (SEQ ID NO: 62) |
| KASQNVGTNVA (SEQ ID NO: 40) | LVSNLES (SEQ ID NO: 53) | FQGSHVPWT (SEQ ID NO: 63) |
| KASQNVGTNVA (SEQ ID NO: 40) | LVSNLES (SEQ ID NO: 53) | QQRSSYPYT (SEQ ID NO: 64) |
| KASQNVGTNVA (SEQ ID NO: 40) | LVSNLES (SEQ ID NO: 53) | QHIREAYT (SEQ ID NO: 65) |
| SASSSISYMH (SEQ ID NO: 41) | SASYRYS (SEQ ID NO: 48) | QQYNSYPYT (SEQ ID NO: 60) |
| SASSSISYMH (SEQ ID NO: 41) | SASYRYS (SEQ ID NO: 48) | HQRSSYPLT (SEQ ID NO: 61) |
| SASSSISYMH (SEQ ID NO: 41) | SASYRYS (SEQ ID NO: 48) | LQYASYPYT (SEQ ID NO: 62) |
| SASSSISYMH (SEQ ID NO: 41) | SASYRYS (SEQ ID NO: 48) | FQGSHVPWT (SEQ ID NO: 63) |
| SASSSISYMH (SEQ ID NO: 41) | SASYRYS (SEQ ID NO: 48) | QQRSSYPYT (SEQ ID NO: 64) |
| SASSSISYMH (SEQ ID NO: 41) | SASYRYS (SEQ ID NO: 48) | QHIREAYT (SEQ ID NO: 65) |
| SASSSISYMH (SEQ ID NO: 41) | DTSKLAS (SEQ ID NO: 49) | QQYNSYPYT (SEQ ID NO: 60) |
| SASSSISYMH (SEQ ID NO: 41) | DTSKLAS (SEQ ID NO: 49) | HQRSSYPLT (SEQ ID NO: 61) |
| SASSSISYMH (SEQ ID NO: 41) | DTSKLAS (SEQ ID NO: 49) | LQYASYPYT (SEQ ID NO: 62) |
| SASSSISYMH (SEQ ID NO: 41) | DTSKLAS (SEQ ID NO: 49) | FQGSHVPWT (SEQ ID NO: 63) |
| SASSSISYMH (SEQ ID NO: 41) | DTSKLAS (SEQ ID NO: 49) | QQRSSYPYT (SEQ ID NO: 64) |
| SASSSISYMH (SEQ ID NO: 41) | DTSKLAS (SEQ ID NO: 49) | QHIREAYT (SEQ ID NO: 65) |

TABLE 8-continued

| Amino Acid Sequences of CDRs | | |
|---|---|---|
| SASSSISYMH (SEQ ID NO: 41) | AASTLDS (SEQ ID NO: 50) | QQYNSYPYT (SEQ ID NO: 60) |
| SASSSISYMH (SEQ ID NO: 41) | AASTLDS (SEQ ID NO: 50) | HQRSSYPLT (SEQ ID NO: 61) |
| SASSSISYMH (SEQ ID NO: 41) | AASTLDS (SEQ ID NO: 50) | LQYASYPYT (SEQ ID NO: 62) |
| SASSSISYMH (SEQ ID NO: 41) | AASTLDS (SEQ ID NO: 50) | FQGSHVPWT (SEQ ID NO: 63) |
| SASSSISYMH (SEQ ID NO: 41) | AASTLDS (SEQ ID NO: 50) | QQRSSYPYT (SEQ ID NO: 64) |
| SASSSISYMH (SEQ ID NO: 41) | AASTLDS (SEQ ID NO: 50) | QHIREAYT (SEQ ID NO: 65) |
| SASSSISYMH (SEQ ID NO: 41) | KVSNRFS (SEQ ID NO: 51) | QQYNSYPYT (SEQ ID NO: 60) |
| SASSSISYMH (SEQ ID NO: 41) | KVSNRFS (SEQ ID NO: 51) | HQRSSYPLT (SEQ ID NO: 61) |
| SASSSISYMH (SEQ ID NO: 41) | KVSNRFS (SEQ ID NO: 51) | LQYASYPYT (SEQ ID NO: 62) |
| SASSSISYMH (SEQ ID NO: 41) | KVSNRFS (SEQ ID NO: 51) | FQGSHVPWT (SEQ ID NO: 63) |
| SASSSISYMH (SEQ ID NO: 41) | KVSNRFS (SEQ ID NO: 51) | QQRSSYPYT (SEQ ID NO: 64) |
| SASSSISYMH (SEQ ID NO: 41) | KVSNRFS (SEQ ID NO: 51) | QHIREAYT (SEQ ID NO: 65) |
| SASSSISYMH (SEQ ID NO: 41) | STSNLAS (SEQ ID NO: 52) | QQYNSYPYT (SEQ ID NO: 60) |
| SASSSISYMH (SEQ ID NO: 41) | STSNLAS (SEQ ID NO: 52) | HQRSSYPLT (SEQ ID NO: 61) |
| SASSSISYMH (SEQ ID NO: 41) | STSNLAS (SEQ ID NO: 52) | LQYASYPYT (SEQ ID NO: 62) |
| SASSSISYMH (SEQ ID NO: 41) | STSNLAS (SEQ ID NO: 52) | FQGSHVPWT (SEQ ID NO: 63) |
| SASSSISYMH (SEQ ID NO: 41) | STSNLAS (SEQ ID NO: 52) | QQRSSYPYT (SEQ ID NO: 64) |
| SASSSISYMH (SEQ ID NO: 41) | STSNLAS (SEQ ID NO: 52) | QHIREAYT (SEQ ID NO: 65) |
| SASSSISYMH (SEQ ID NO: 41) | LVSNLES (SEQ ID NO: 53) | QQYNSYPYT (SEQ ID NO: 60) |
| SASSSISYMH (SEQ ID NO: 41) | LVSNLES (SEQ ID NO: 53) | HQRSSYPLT (SEQ ID NO: 61) |
| SASSSISYMH (SEQ ID NO: 41) | LVSNLES (SEQ ID NO: 53) | LQYASYPYT (SEQ ID NO: 62) |
| SASSSISYMH (SEQ ID NO: 41) | LVSNLES (SEQ ID NO: 53) | FQGSHVPWT (SEQ ID NO: 63) |
| SASSSISYMH (SEQ ID NO: 41) | LVSNLES (SEQ ID NO: 53) | QQRSSYPYT (SEQ ID NO: 64) |
| SASSSISYMH (SEQ ID NO: 41) | LVSNLES (SEQ ID NO: 53) | QHIREAYT (SEQ ID NO: 65) |
| RASQEISGYLS (SEQ ID NO: 42) | SASYRYS (SEQ ID NO: 48) | QQYNSYPYT (SEQ ID NO: 60) |
| RASQEISGYLS (SEQ ID NO: 42) | SASYRYS (SEQ ID NO: 48) | HQRSSYPLT (SEQ ID NO: 61) |

TABLE 8-continued

| Amino Acid Sequences of CDRs | | |
|---|---|---|
| RASQEISGYLS (SEQ ID NO: 42) | SASYRYS (SEQ ID NO: 48) | LQYASYPYT (SEQ ID NO: 62) |
| RASQEISGYLS (SEQ ID NO: 42) | SASYRYS (SEQ ID NO: 48) | FQGSHVPWT (SEQ ID NO: 63) |
| RASQEISGYLS (SEQ ID NO: 42) | SASYRYS (SEQ ID NO: 48) | QQRSSYPYT (SEQ ID NO: 64) |
| RASQEISGYLS (SEQ ID NO: 42) | SASYRYS (SEQ ID NO: 48) | QHIREAYT (SEQ ID NO: 65) |
| RASQEISGYLS (SEQ ID NO: 42) | DTSKLAS (SEQ ID NO: 49) | QQYNSYPYT (SEQ ID NO: 60) |
| RASQEISGYLS (SEQ ID NO: 42) | DTSKLAS (SEQ ID NO: 49) | HQRSSYPLT (SEQ ID NO: 61) |
| RASQEISGYLS (SEQ ID NO: 42) | DTSKLAS (SEQ ID NO: 49) | LQYASYPYT (SEQ ID NO: 62) |
| RASQEISGYLS (SEQ ID NO: 42) | DTSKLAS (SEQ ID NO: 49) | FQGSHVPWT (SEQ ID NO: 63) |
| RASQEISGYLS (SEQ ID NO: 42) | DTSKLAS (SEQ ID NO: 49) | QQRSSYPYT (SEQ ID NO: 64) |
| RASQEISGYLS (SEQ ID NO: 42) | DTSKLAS (SEQ ID NO: 49) | QHIREAYT (SEQ ID NO: 65) |
| RASQEISGYLS (SEQ ID NO: 42) | AASTLDS (SEQ ID NO: 50) | QQYNSYPYT (SEQ ID NO: 60) |
| RASQEISGYLS (SEQ ID NO: 42) | AASTLDS (SEQ ID NO: 50) | HQRSSYPLT (SEQ ID NO: 61) |
| RASQEISGYLS (SEQ ID NO: 42) | AASTLDS (SEQ ID NO: 50) | LQYASYPYT (SEQ ID NO: 62) |
| RASQEISGYLS (SEQ ID NO: 42) | AASTLDS (SEQ ID NO: 50) | FQGSHVPWT (SEQ ID NO: 63) |
| RASQEISGYLS (SEQ ID NO: 42) | AASTLDS (SEQ ID NO: 50) | QQRSSYPYT (SEQ ID NO: 64) |
| RASQEISGYLS (SEQ ID NO: 42) | AASTLDS (SEQ ID NO: 50) | QHIREAYT (SEQ ID NO: 65) |
| RASQEISGYLS (SEQ ID NO: 42) | KVSNRFS (SEQ ID NO: 51) | QQYNSYPYT (SEQ ID NO: 60) |
| RASQEISGYLS (SEQ ID NO: 42) | KVSNRFS (SEQ ID NO: 51) | HQRSSYPLT (SEQ ID NO: 61) |
| RASQEISGYLS (SEQ ID NO: 42) | KVSNRFS (SEQ ID NO: 51) | LQYASYPYT (SEQ ID NO: 62) |
| RASQEISGYLS (SEQ ID NO: 42) | KVSNRFS (SEQ ID NO: 51) | FQGSHVPWT (SEQ ID NO: 63) |
| RASQEISGYLS (SEQ ID NO: 42) | KVSNRFS (SEQ ID NO: 51) | QQRSSYPYT (SEQ ID NO: 64) |
| RASQEISGYLS (SEQ ID NO: 42) | KVSNRFS (SEQ ID NO: 51) | QHIREAYT (SEQ ID NO: 65) |
| RASQEISGYLS (SEQ ID NO: 42) | STSNLAS (SEQ ID NO: 52) | QQYNSYPYT (SEQ ID NO: 60) |
| RASQEISGYLS (SEQ ID NO: 42) | STSNLAS (SEQ ID NO: 52) | HQRSSYPLT (SEQ ID NO: 61) |
| RASQEISGYLS (SEQ ID NO: 42) | STSNLAS (SEQ ID NO: 52) | LQYASYPYT (SEQ ID NO: 62) |
| RASQEISGYLS (SEQ ID NO: 42) | STSNLAS (SEQ ID NO: 52) | FQGSHVPWT (SEQ ID NO: 63) |

TABLE 8-continued

| Amino Acid Sequences of CDRs | | |
|---|---|---|
| RASQEISGYLS (SEQ ID NO: 42) | STSNLAS (SEQ ID NO: 52) | QQRSSYPYT (SEQ ID NO: 64) |
| RASQEISGYLS (SEQ ID NO: 42) | STSNLAS (SEQ ID NO: 52) | QHIREAYT (SEQ ID NO: 65) |
| RASQEISGYLS (SEQ ID NO: 42) | LVSNLES (SEQ ID NO: 53) | QQYNSYPYT (SEQ ID NO: 60) |
| RASQEISGYLS (SEQ ID NO: 42) | LVSNLES (SEQ ID NO: 53) | HQRSSYPLT (SEQ ID NO: 61) |
| RASQEISGYLS (SEQ ID NO: 42) | LVSNLES (SEQ ID NO: 53) | LQYASYPYT (SEQ ID NO: 62) |
| RASQEISGYLS (SEQ ID NO: 42) | LVSNLES (SEQ ID NO: 53) | FQGSHVPWT (SEQ ID NO: 63) |
| RASQEISGYLS (SEQ ID NO: 42) | LVSNLES (SEQ ID NO: 53) | QQRSSYPYT (SEQ ID NO: 64) |
| RASQEISGYLS (SEQ ID NO: 42) | LVSNLES (SEQ ID NO: 53) | QHIREAYT (SEQ ID NO: 65) |
| RSSQSIVHSNGNTYLE (SEQ ID NO: 43) | SASYRYS (SEQ ID NO: 48) | QQYNSYPYT (SEQ ID NO: 60) |
| RSSQSIVHSNGNTYLE (SEQ ID NO: 43) | SASYRYS (SEQ ID NO: 48) | HQRSSYPLT (SEQ ID NO: 61) |
| RSSQSIVHSNGNTYLE (SEQ ID NO: 43) | SASYRYS (SEQ ID NO: 48) | LQYASYPYT (SEQ ID NO: 62) |
| RSSQSIVHSNGNTYLE (SEQ ID NO: 43) | SASYRYS (SEQ ID NO: 48) | FQGSHVPWT (SEQ ID NO: 63) |
| RSSQSIVHSNGNTYLE (SEQ ID NO: 43) | SASYRYS (SEQ ID NO: 48) | QQRSSYPYT (SEQ ID NO: 64) |
| RSSQSIVHSNGNTYLE (SEQ ID NO: 43) | SASYRYS (SEQ ID NO: 48) | QHIREAYT (SEQ ID NO: 65) |
| RSSQSIVHSNGNTYLE (SEQ ID NO: 43) | DTSKLAS (SEQ ID NO: 49) | QQYNSYPYT (SEQ ID NO: 60) |
| RSSQSIVHSNGNTYLE (SEQ ID NO: 43) | DTSKLAS (SEQ ID NO: 49) | HQRSSYPLT (SEQ ID NO: 61) |
| RSSQSIVHSNGNTYLE (SEQ ID NO: 43) | DTSKLAS (SEQ ID NO: 49) | LQYASYPYT (SEQ ID NO: 62) |
| RSSQSIVHSNGNTYLE (SEQ ID NO: 43) | DTSKLAS (SEQ ID NO: 49) | FQGSHVPWT (SEQ ID NO: 63) |
| RSSQSIVHSNGNTYLE (SEQ ID NO: 43) | DTSKLAS (SEQ ID NO: 49) | QQRSSYPYT (SEQ ID NO: 64) |
| RSSQSIVHSNGNTYLE (SEQ ID NO: 43) | DTSKLAS (SEQ ID NO: 49) | QHIREAYT (SEQ ID NO: 65) |
| RSSQSIVHSNGNTYLE (SEQ ID NO: 43) | AASTLDS (SEQ ID NO: 50) | QQYNSYPYT (SEQ ID NO: 60) |
| RSSQSIVHSNGNTYLE (SEQ ID NO: 43) | AASTLDS (SEQ ID NO: 50) | HQRSSYPLT (SEQ ID NO: 61) |
| RSSQSIVHSNGNTYLE (SEQ ID NO: 43) | AASTLDS (SEQ ID NO: 50) | LQYASYPYT (SEQ ID NO: 62) |
| RSSQSIVHSNGNTYLE (SEQ ID NO: 43) | AASTLDS (SEQ ID NO: 50) | FQGSHVPWT (SEQ ID NO: 63) |
| RSSQSIVHSNGNTYLE (SEQ ID NO: 43) | AASTLDS (SEQ ID NO: 50) | QQRSSYPYT (SEQ ID NO: 64) |
| RSSQSIVHSNGNTYLE (SEQ ID NO: 43) | AASTLDS (SEQ ID NO: 50) | QHIREAYT (SEQ ID NO: 65) |

TABLE 8-continued

| Amino Acid Sequences of CDRs | | |
|---|---|---|
| RSSQSIVHSNGNTYLE (SEQ ID NO: 43) | KVSNRFS (SEQ ID NO: 51) | QQYNSYPYT (SEQ ID NO: 60) |
| RSSQSIVHSNGNTYLE (SEQ ID NO: 43) | KVSNRFS (SEQ ID NO: 51) | HQRSSYPLT (SEQ ID NO: 61) |
| RSSQSIVHSNGNTYLE (SEQ ID NO: 43) | KVSNRFS (SEQ ID NO: 51) | LQYASYPYT (SEQ ID NO: 62) |
| RSSQSIVHSNGNTYLE (SEQ ID NO: 43) | KVSNRFS (SEQ ID NO: 51) | FQGSHVPWT (SEQ ID NO: 63) |
| RSSQSIVHSNGNTYLE (SEQ ID NO: 43) | KVSNRFS (SEQ ID NO: 51) | QQRSSYPYT (SEQ ID NO: 64) |
| RSSQSIVHSNGNTYLE (SEQ ID NO: 43) | KVSNRFS (SEQ ID NO: 51) | QHIREAYT (SEQ ID NO: 65) |
| RSSQSIVHSNGNTYLE (SEQ ID NO: 43) | STSNLAS (SEQ ID NO: 52) | QQYNSYPYT (SEQ ID NO: 60) |
| RSSQSIVHSNGNTYLE (SEQ ID NO: 43) | STSNLAS (SEQ ID NO: 52) | HQRSSYPLT (SEQ ID NO: 61) |
| RSSQSIVHSNGNTYLE (SEQ ID NO: 43) | STSNLAS (SEQ ID NO: 52) | LQYASYPYT (SEQ ID NO: 62) |
| RSSQSIVHSNGNTYLE (SEQ ID NO: 43) | STSNLAS (SEQ ID NO: 52) | FQGSHVPWT (SEQ ID NO: 63) |
| RSSQSIVHSNGNTYLE (SEQ ID NO: 43) | STSNLAS (SEQ ID NO: 52) | QQRSSYPYT (SEQ ID NO: 64) |
| RSSQSIVHSNGNTYLE (SEQ ID NO: 43) | STSNLAS (SEQ ID NO: 52) | QHIREAYT (SEQ ID NO: 65) |
| RSSQSIVHSNGNTYLE (SEQ ID NO: 43) | LVSNLES (SEQ ID NO: 53) | QQYNSYPYT (SEQ ID NO: 60) |
| RSSQSIVHSNGNTYLE (SEQ ID NO: 43) | LVSNLES (SEQ ID NO: 53) | HQRSSYPLT (SEQ ID NO: 61) |
| RSSQSIVHSNGNTYLE (SEQ ID NO: 43) | LVSNLES (SEQ ID NO: 53) | LQYASYPYT (SEQ ID NO: 62) |
| RSSQSIVHSNGNTYLE (SEQ ID NO: 43) | LVSNLES (SEQ ID NO: 53) | FQGSHVPWT (SEQ ID NO: 63) |
| RSSQSIVHSNGNTYLE (SEQ ID NO: 43) | LVSNLES (SEQ ID NO: 53) | QQRSSYPYT (SEQ ID NO: 64) |
| RSSQSIVHSNGNTYLE (SEQ ID NO: 43) | LVSNLES (SEQ ID NO: 53) | QHIREAYT (SEQ ID NO: 65) |
| SASSSVSYMH (SEQ ID NO: 44) | SASYRYS (SEQ ID NO: 48) | QQYNSYPYT (SEQ ID NO: 60) |
| SASSSVSYMH (SEQ ID NO: 44) | SASYRYS (SEQ ID NO: 48) | HQRSSYPLT (SEQ ID NO: 61) |
| SASSSVSYMH (SEQ ID NO: 44) | SASYRYS (SEQ ID NO: 48) | LQYASYPYT (SEQ ID NO: 62) |
| SASSSVSYMH (SEQ ID NO: 44) | SASYRYS (SEQ ID NO: 48) | FQGSHVPWT (SEQ ID NO: 63) |
| SASSSVSYMH (SEQ ID NO: 44) | SASYRYS (SEQ ID NO: 48) | QQRSSYPYT (SEQ ID NO: 64) |
| SASSSVSYMH (SEQ ID NO: 44) | SASYRYS (SEQ ID NO: 48) | QHIREAYT (SEQ ID NO: 65) |
| SASSSVSYMH (SEQ ID NO: 44) | DTSKLAS (SEQ ID NO: 49) | QQYNSYPYT (SEQ ID NO: 60) |
| SASSSVSYMH (SEQ ID NO: 44) | DTSKLAS (SEQ ID NO: 49) | HQRSSYPLT (SEQ ID NO: 61) |

TABLE 8-continued

| Amino Acid Sequences of CDRs | | |
|---|---|---|
| SASSSVSYMH (SEQ ID NO: 44) | DTSKLAS (SEQ ID NO: 49) | LQYASYPYT (SEQ ID NO: 62) |
| SASSSVSYMH (SEQ ID NO: 44) | DTSKLAS (SEQ ID NO: 49) | FQGSHVPWT (SEQ ID NO: 63) |
| SASSSVSYMH (SEQ ID NO: 44) | DTSKLAS (SEQ ID NO: 49) | QQRSSYPYT (SEQ ID NO: 64) |
| SASSSVSYMH (SEQ ID NO: 44) | DTSKLAS (SEQ ID NO: 49) | QHIREAYT (SEQ ID NO: 65) |
| SASSSVSYMH (SEQ ID NO: 44) | AASTLDS (SEQ ID NO: 50) | QQYNSYPYT (SEQ ID NO: 60) |
| SASSSVSYMH (SEQ ID NO: 44) | AASTLDS (SEQ ID NO: 50) | HQRSSYPLT (SEQ ID NO: 61) |
| SASSSVSYMH (SEQ ID NO: 44) | AASTLDS (SEQ ID NO: 50) | LQYASYPYT (SEQ ID NO: 62) |
| SASSSVSYMH (SEQ ID NO: 44) | AASTLDS (SEQ ID NO: 50) | FQGSHVPWT (SEQ ID NO: 63) |
| SASSSVSYMH (SEQ ID NO: 44) | AASTLDS (SEQ ID NO: 50) | QQRSSYPYT (SEQ ID NO: 64) |
| SASSSVSYMH (SEQ ID NO: 44) | AASTLDS (SEQ ID NO: 50) | QHIREAYT (SEQ ID NO: 65) |
| SASSSVSYMH (SEQ ID NO: 44) | KVSNRFS (SEQ ID NO: 51) | QQYNSYPYT (SEQ ID NO: 60) |
| SASSSVSYMH (SEQ ID NO: 44) | KVSNRFS (SEQ ID NO: 51) | HQRSSYPLT (SEQ ID NO: 61) |
| SASSSVSYMH (SEQ ID NO: 44) | KVSNRFS (SEQ ID NO: 51) | LQYASYPYT (SEQ ID NO: 62) |
| SASSSVSYMH (SEQ ID NO: 44) | KVSNRFS (SEQ ID NO: 51) | FQGSHVPWT (SEQ ID NO: 63) |
| SASSSVSYMH (SEQ ID NO: 44) | KVSNRFS (SEQ ID NO: 51) | QQRSSYPYT (SEQ ID NO: 64) |
| SASSSVSYMH (SEQ ID NO: 44) | KVSNRFS (SEQ ID NO: 51) | QHIREAYT (SEQ ID NO: 65) |
| SASSSVSYMH (SEQ ID NO: 44) | STSNLAS (SEQ ID NO: 52) | QQYNSYPYT (SEQ ID NO: 60) |
| SASSSVSYMH (SEQ ID NO: 44) | STSNLAS (SEQ ID NO: 52) | HQRSSYPLT (SEQ ID NO: 61) |
| SASSSVSYMH (SEQ ID NO: 44) | STSNLAS (SEQ ID NO: 52) | LQYASYPYT (SEQ ID NO: 62) |
| SASSSVSYMH (SEQ ID NO: 44) | STSNLAS (SEQ ID NO: 52) | FQGSHVPWT (SEQ ID NO: 63) |
| SASSSVSYMH (SEQ ID NO: 44) | STSNLAS (SEQ ID NO: 52) | QQRSSYPYT (SEQ ID NO: 64) |
| SASSSVSYMH (SEQ ID NO: 44) | STSNLAS (SEQ ID NO: 52) | QHIREAYT (SEQ ID NO: 65) |
| SASSSVSYMH (SEQ ID NO: 44) | LVSNLES (SEQ ID NO: 53) | QQYNSYPYT (SEQ ID NO: 60) |
| SASSSVSYMH (SEQ ID NO: 44) | LVSNLES (SEQ ID NO: 53) | HQRSSYPLT (SEQ ID NO: 61) |
| SASSSVSYMH (SEQ ID NO: 44) | LVSNLES (SEQ ID NO: 53) | LQYASYPYT (SEQ ID NO: 62) |
| SASSSVSYMH (SEQ ID NO: 44) | LVSNLES (SEQ ID NO: 53) | FQGSHVPWT (SEQ ID NO: 63) |

TABLE 8-continued

| Amino Acid Sequences of CDRs | | |
|---|---|---|
| SASSSVSYMH (SEQ ID NO: 44) | LVSNLES (SEQ ID NO: 53) | QQRSSYPYT (SEQ ID NO: 64) |
| SASSSVSYMH (SEQ ID NO: 44) | LVSNLES (SEQ ID NO: 53) | QHIREAYT (SEQ ID NO: 65) |
| KSVSTSGYSYMH (SEQ ID NO: 45) | SASYRYS (SEQ ID NO: 48) | QQYNSYPYT (SEQ ID NO: 60) |
| KSVSTSGYSYMH (SEQ ID NO: 45) | SASYRYS (SEQ ID NO: 48) | HQRSSYPLT (SEQ ID NO: 61) |
| KSVSTSGYSYMH (SEQ ID NO: 45) | SASYRYS (SEQ ID NO: 48) | LQYASYPYT (SEQ ID NO: 62) |
| KSVSTSGYSYMH (SEQ ID NO: 45) | SASYRYS (SEQ ID NO: 48) | FQGSHVPWT (SEQ ID NO: 63) |
| KSVSTSGYSYMH (SEQ ID NO: 45) | SASYRYS (SEQ ID NO: 48) | QQRSSYPYT (SEQ ID NO: 64) |
| KSVSTSGYSYMH (SEQ ID NO: 45) | SASYRYS (SEQ ID NO: 48) | QHIREAYT (SEQ ID NO: 65) |
| KSVSTSGYSYMH (SEQ ID NO: 45) | DTSKLAS (SEQ ID NO: 49) | QQYNSYPYT (SEQ ID NO: 60) |
| KSVSTSGYSYMH (SEQ ID NO: 45) | DTSKLAS (SEQ ID NO: 49) | HQRSSYPLT (SEQ ID NO: 61) |
| KSVSTSGYSYMH (SEQ ID NO: 45) | DTSKLAS (SEQ ID NO: 49) | LQYASYPYT (SEQ ID NO: 62) |
| KSVSTSGYSYMH (SEQ ID NO: 45) | DTSKLAS (SEQ ID NO: 49) | FQGSHVPWT (SEQ ID NO: 63) |
| KSVSTSGYSYMH (SEQ ID NO: 45) | DTSKLAS (SEQ ID NO: 49) | QQRSSYPYT (SEQ ID NO: 64) |
| KSVSTSGYSYMH (SEQ ID NO: 45) | DTSKLAS (SEQ ID NO: 49) | QHIREAYT (SEQ ID NO: 65) |
| KSVSTSGYSYMH (SEQ ID NO: 45) | AASTLDS (SEQ ID NO: 50) | QQYNSYPYT (SEQ ID NO: 60) |
| KSVSTSGYSYMH (SEQ ID NO: 45) | AASTLDS (SEQ ID NO: 50) | HQRSSYPLT (SEQ ID NO: 61) |
| KSVSTSGYSYMH (SEQ ID NO: 45) | AASTLDS (SEQ ID NO: 50) | LQYASYPYT (SEQ ID NO: 62) |
| KSVSTSGYSYMH (SEQ ID NO: 45) | AASTLDS (SEQ ID NO: 50) | FQGSHVPWT (SEQ ID NO: 63) |
| KSVSTSGYSYMH (SEQ ID NO: 45) | AASTLDS (SEQ ID NO: 50) | QQRSSYPYT (SEQ ID NO: 64) |
| KSVSTSGYSYMH (SEQ ID NO: 45) | AASTLDS (SEQ ID NO: 50) | QHIREAYT (SEQ ID NO: 65) |
| KSVSTSGYSYMH (SEQ ID NO: 45) | KVSNRFS (SEQ ID NO: 51) | QQYNSYPYT (SEQ ID NO: 60) |
| KSVSTSGYSYMH (SEQ ID NO: 45) | KVSNRFS (SEQ ID NO: 51) | HQRSSYPLT (SEQ ID NO: 61) |
| KSVSTSGYSYMH (SEQ ID NO: 45) | KVSNRFS (SEQ ID NO: 51) | LQYASYPYT (SEQ ID NO: 62) |
| KSVSTSGYSYMH (SEQ ID NO: 45) | KVSNRFS (SEQ ID NO: 51) | FQGSHVPWT (SEQ ID NO: 63) |
| KSVSTSGYSYMH (SEQ ID NO: 45) | KVSNRFS (SEQ ID NO: 51) | QQRSSYPYT (SEQ ID NO: 64) |
| KSVSTSGYSYMH (SEQ ID NO: 45) | KVSNRFS (SEQ ID NO: 51) | QHIREAYT (SEQ ID NO: 65) |
| KSVSTSGYSYMH (SEQ ID NO: 45) | STSNLAS (SEQ ID NO: 52) | QQYNSYPYT (SEQ ID NO: 60) |
| KSVSTSGYSYMH (SEQ ID NO: 45) | STSNLAS (SEQ ID NO: 52) | HQRSSYPLT (SEQ ID NO: 61) |
| KSVSTSGYSYMH (SEQ ID NO: 45) | STSNLAS (SEQ ID NO: 52) | LQYASYPYT (SEQ ID NO: 62) |
| KSVSTSGYSYMH (SEQ ID NO: 45) | STSNLAS (SEQ ID NO: 52) | FQGSHVPWT (SEQ ID NO: 63) |
| KSVSTSGYSYMH (SEQ ID NO: 45) | STSNLAS (SEQ ID NO: 52) | QQRSSYPYT (SEQ ID NO: 64) |
| KSVSTSGYSYMH (SEQ ID NO: 45) | STSNLAS (SEQ ID NO: 52) | QHIREAYT (SEQ ID NO: 65) |
| KSVSTSGYSYMH (SEQ ID NO: 45) | LVSNLES (SEQ ID NO: 53) | QQYNSYPYT (SEQ ID NO: 60) |
| KSVSTSGYSYMH (SEQ ID NO: 45) | LVSNLES (SEQ ID NO: 53) | HQRSSYPLT (SEQ ID NO: 61) |
| KSVSTSGYSYMH (SEQ ID NO: 45) | LVSNLES (SEQ ID NO: 53) | LQYASYPYT (SEQ ID NO: 62) |
| KSVSTSGYSYMH (SEQ ID NO: 45) | LVSNLES (SEQ ID NO: 53) | FQGSHVPWT (SEQ ID NO: 63) |
| KSVSTSGYSYMH (SEQ ID NO: 45) | LVSNLES (SEQ ID NO: 53) | QQRSSYPYT (SEQ ID NO: 64) |
| KSVSTSGYSYMH (SEQ ID NO: 45) | LVSNLES (SEQ ID NO: 53) | QHIREAYT (SEQ ID NO: 65) |

What is claimed:

1. A chimeric antigen receptor (CAR), comprising:

(a) an extracellular region comprising a binding domain that specifically binds to at least a portion of B7-H3 wherein the binding domain comprises (i) a light chain variable region ($V_L$) of an antibody that comprises an amino acid sequence selected from SEQ ID NO: 8, SEQ ID NO: 10, or SEQ ID NO:12, and (ii) a heavy chain variable region ($V_H$) chain of an antibody that comprises an amino acid sequence selected from SEQ NO: 7, SEQ ID NO:9, or SEQ ID NO:11;

(b) a transmembrane region; and (c) an intracellular region comprising an effector domain and a costimulatory domain.

2. The CAR of claim 1, wherein the binding domain is an scFv.

3. The CAR of claim 2, wherein the extracellular region further comprises a linker.

4. The CAR of claim 3, wherein the linker is a glycine-serine linker.

5. The CAR of claim 4, wherein the extracellular region further comprises a leader.

6. The CAR of claim 5, wherein the transmembrane region comprises or is a combination of (i) a CD8α hinge and (ii) a CD8α transmembrane region.

7. The CAR of claim 6, wherein the effector domain is CD3ζ or a portion or variant thereof.

8. The CAR of claim 7, wherein the costimulatory domain is a CD28 costimulatory domain, a 4-1BB costimulatory domain, or a combination thereof.

9. The CAR claim 8, wherein the costimulatory domain comprises a CD28 costimulatory domain and the effector domain comprises CD3ζ.

10. The CAR of claim 8, wherein the costimulatory domain comprises a 4-1BB costimulatory domain and the effector domain comprises CD3ζ.

11. The CAR of claim 8, wherein the costimulatory domain comprises a CD28 costimulatory domain and a 4-1BB costimulatory domain, and the effector domain comprises CD3 ζ.

12. The CAR claim 11, wherein the binding domain is chimeric, human, or humanized.

13. An expression vector, comprising an isolated polynucleotide encoding the CAR of claim 11 operably linked to an expression control sequence.

14. The expression vector of claim 13, further comprising an isolated polynucleotide encoding a self-cleaving peptide.

15. The expression vector of claim 14, wherein the self-cleaving peptide is a 2A self-cleaving peptide or a P2A peptide.

16. The expression vector of claim 13, further comprising an isolated polynucleotide encoding a transduction marker polypeptide.

17. The expression vector of claim 16, wherein the transduction marker polypeptide is a truncated form of epidermal growth factor receptor (EGFRt) or GFP.

18. A chimeric antigen receptor (CAR), comprising:

(a) an extracellular region comprising a binding domain that specifically binds to at least a portion of B7-H3 wherein the binding domain comprises (i) a $V_L$ of an antibody that comprises an amino acid sequence selected from SEQ ID NO:14, SEQ ID NO:16, or SEQ ID NO: 18, and (ii) a $V_H$ of an antibody that comprises an amino acid sequence selected from SEQ ID NO: 13, SEQ ID NO:15, or SEQ ID NO: 17;

(b) a transmembrane region; and (c) an intracellular region comprising an effector domain and a costimulatory domain.

* * * * *

SEQUENCE LISTING

<160> NUMBER OF SEQ ID NOS: 121

<210> SEQ ID NO 1
<211> LENGTH: 69
<212> TYPE: PRT
<213> ORGANISM: Homo sapiens

<400> SEQUENCE: 1

Thr Thr Thr Pro Ala Pro Arg Pro Pro Thr Pro Ala Pro Thr Ile Ala
1               5                   10                  15

```
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65


<210> SEQ ID NO 2
<211> LENGTH: 41
<212> TYPE: PRT
<213> ORGANISM: Homo sapiens

<400> SEQUENCE: 2

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 3
<211> LENGTH: 42
<212> TYPE: PRT
<213> ORGANISM: Homo sapiens

<400> SEQUENCE: 3

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40


<210> SEQ ID NO 4
<211> LENGTH: 113
<212> TYPE: PRT
<213> ORGANISM: Homo sapiens

<400> SEQUENCE: 4

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg
```

<210> SEQ ID NO 5
<211> LENGTH: 22
<212> TYPE: PRT
<213> ORGANISM: Homo sapiens

<400> SEQUENCE: 5

```
Gly Ser Gly Ala Thr Asn Phe Ser Leu Leu Lys Gln Ala Gly Asp Val
1               5                   10                  15

Glu Glu Asn Pro Gly Pro
            20
```

<210> SEQ ID NO 6
<211> LENGTH: 335
<212> TYPE: PRT
<213> ORGANISM: Homo sapiens

<400> SEQUENCE: 6

```
Arg Lys Val Cys Asn Gly Ile Gly Ile Gly Glu Phe Lys Asp Ser Leu
1               5                   10                  15

Ser Ile Asn Ala Thr Asn Ile Lys His Phe Lys Asn Cys Thr Ser Ile
            20                  25                  30

Ser Gly Asp Leu His Ile Leu Pro Val Ala Phe Arg Gly Asp Ser Phe
        35                  40                  45

Thr His Thr Pro Pro Leu Asp Pro Gln Glu Leu Asp Ile Leu Lys Thr
    50                  55                  60

Val Lys Glu Ile Thr Gly Phe Leu Leu Ile Gln Ala Trp Pro Glu Asn
65                  70                  75                  80

Arg Thr Asp Leu His Ala Phe Glu Asn Leu Glu Ile Ile Arg Gly Arg
                85                  90                  95

Thr Lys Gln His Gly Gln Phe Ser Leu Ala Val Val Ser Leu Asn Ile
            100                 105                 110

Thr Ser Leu Gly Leu Arg Ser Leu Lys Glu Ile Ser Asp Gly Asp Val
        115                 120                 125

Ile Ile Ser Gly Asn Lys Asn Leu Cys Tyr Ala Asn Thr Ile Asn Trp
    130                 135                 140

Lys Lys Leu Phe Gly Thr Ser Gly Gln Lys Thr Lys Ile Ile Ser Asn
145                 150                 155                 160

Arg Gly Glu Asn Ser Cys Lys Ala Thr Gly Gln Val Cys His Ala Leu
                165                 170                 175

Cys Ser Pro Glu Gly Cys Trp Gly Pro Glu Pro Arg Asp Cys Val Ser
            180                 185                 190

Cys Arg Asn Val Ser Arg Gly Arg Glu Cys Val Asp Lys Cys Asn Leu
        195                 200                 205

Leu Glu Gly Glu Pro Arg Glu Phe Val Glu Asn Ser Glu Cys Ile Gln
    210                 215                 220

Cys His Pro Glu Cys Leu Pro Gln Ala Met Asn Ile Thr Cys Thr Gly
225                 230                 235                 240

Arg Gly Pro Asp Asn Cys Ile Gln Cys Ala His Tyr Ile Asp Gly Pro
                245                 250                 255

His Cys Val Lys Thr Cys Pro Ala Gly Val Met Gly Glu Asn Asn Thr
            260                 265                 270

Leu Val Trp Lys Tyr Ala Asp Ala Gly His Val Cys His Leu Cys His
        275                 280                 285

Pro Asn Cys Thr Tyr Gly Cys Thr Gly Pro Gly Leu Glu Gly Cys Pro
    290                 295                 300
```

```
Thr Asn Gly Pro Lys Ile Pro Ser Ile Ala Thr Gly Met Val Gly Ala
305                 310                 315                 320

Leu Leu Leu Leu Leu Val Val Ala Leu Gly Ile Gly Leu Phe Met
                325                 330                 335


<210> SEQ ID NO 7
<211> LENGTH: 134
<212> TYPE: PRT
<213> ORGANISM: Artificial Sequence
<220> FEATURE:
<223> OTHER INFORMATION: 1G5 mAb VH chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(44)
<223> OTHER INFORMATION: FR1
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (55)..(68)
<223> OTHER INFORMATION: FR2
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MISC_FEATURE
<222> LOCATION: (86)..(117)
<223> OTHER INFORMATION: FR3
<220> FEATURE:
<221> NAME/KEY: MISC_FEATURE
<222> LOCATION: (118)..(123)
<223> OTHER INFORMATION: CDR3
<220> FEATURE:
<221> NAME/KEY: MISC_FEATURE
<222> LOCATION: (124)..(134)
<223> OTHER INFORMATION: FR4

<400> SEQUENCE: 7

Met Gly Trp Ser Tyr Ile Ile Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Met Ile His Pro Asn Ser Gly Ser Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Gly Gly Tyr Phe Asp Tyr Trp Gly Gln Gly Thr
        115                 120                 125

Thr Leu Thr Val Ser Ser
    130


<210> SEQ ID NO 8
<211> LENGTH: 128
```

<212> TYPE: PRT
<213> ORGANISM: Artificial Sequence
<220> FEATURE:
<223> OTHER INFORMATION: 1G5 mAb VL chain
<220> FEATURE:
<221> NAME/KEY: MISC_FEATURE
<222> LOCATION: (1)..(20)
<223> OTHER INFORMATION: Leader sequence
<220> FEATURE:
<221> NAME/KEY: MISC_FEATURE
<222> LOCATION: (21)..(43)
<223> OTHER INFORMATION: FR1
<220> FEATURE:
<221> NAME/KEY: MISC_FEATURE
<222> LOCATION: (44)..(54)
<223> OTHER INFORMATION: CDR1
<220> FEATURE:
<221> NAME/KEY: MISC_FEATURE
<222> LOCATION: (55)..(69)
<223> OTHER INFORMATION: FR2
<220> FEATURE:
<221> NAME/KEY: MISC_FEATURE
<222> LOCATION: (70)..(76)
<223> OTHER INFORMATION: CDR2
<220> FEATURE:
<221> NAME/KEY: MISC_FEATURE
<222> LOCATION: (77)..(108)
<223> OTHER INFORMATION: FR3
<220> FEATURE:
<221> NAME/KEY: MISC_FEATURE
<222> LOCATION: (109)..(117)
<223> OTHER INFORMATION: CDR3
<220> FEATURE:
<221> NAME/KEY: MISC_FEATURE
<222> LOCATION: (118)..(128)
<223> OTHER INFORMATION: FR4

<400> SEQUENCE: 8

```
Met Lys Thr Gln Thr Gln Val Phe Val Tyr Met Leu Leu Trp Leu Ser
1               5                   10                  15

Gly Val Asp Gly Asp Ile Val Met Thr Gln Ser Gln Lys Phe Met Ser
            20                  25                  30

Thr Ser Val Gly Asp Arg Val Ser Val Thr Cys Lys Ala Ser Gln Asn
        35                  40                  45

Val Gly Thr Asn Val Ala Trp Tyr Gln Gln Lys Pro Gly Gln Ser Pro
    50                  55                  60

Lys Ala Leu Ile Tyr Ser Ala Ser Tyr Arg Tyr Ser Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Glu Tyr Phe Cys Gln Gln Tyr Asn
            100                 105                 110

Ser Tyr Pro Tyr Thr Phe Gly Gly Gly Thr Lys Leu Glu Ile Lys Arg
        115                 120                 125
```

<210> SEQ ID NO 9
<211> LENGTH: 135
<212> TYPE: PRT
<213> ORGANISM: Artificial Sequence
<220> FEATURE:
<223> OTHER INFORMATION: 23B2 mAb VH chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(44)
<223> OTHER INFORMATION: FR1
<220> FEATURE:

<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (55)..(68)
<223> OTHER INFORMATION: FR2
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MISC_FEATURE
<222> LOCATION: (86)..(115)
<223> OTHER INFORMATION: FR3
<220> FEATURE:
<221> NAME/KEY: MISC_FEATURE
<222> LOCATION: (116)..(124)
<223> OTHER INFORMATION: CDR3
<220> FEATURE:
<221> NAME/KEY: MISC_FEATURE
<222> LOCATION: (125)..(135)
<223> OTHER INFORMATION: FR4

<400> SEQUENCE: 9

```
Met Gly Trp Ser Cys Ile Met Leu Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Met Ile His Pro Asn Ser Gly Ser Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Glu Ser Arg Gln Leu Asp Tyr Trp Gly Gln Gly
        115                 120                 125

Thr Thr Leu Thr Val Ser Ser
    130                 135
```

<210> SEQ ID NO 10
<211> LENGTH: 128
<212> TYPE: PRT
<213> ORGANISM: Artificial Sequence
<220> FEATURE:
<223> OTHER INFORMATION: 23B2 mAb VL chain
<220> FEATURE:
<221> NAME/KEY: MISC_FEATURE
<222> LOCATION: (1)..(22)
<223> OTHER INFORMATION: Leader sequence
<220> FEATURE:
<221> NAME/KEY: MISC_FEATURE
<222> LOCATION: (23)..(45)
<223> OTHER INFORMATION: FR1
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (56)..(70)
<223> OTHER INFORMATION: FR2
<220> FEATURE:
<221> NAME/KEY: MISC_FEATURE
<222> LOCATION: (71)..(77)

<223> OTHER INFORMATION: CDR2
<220> FEATURE:
<221> NAME/KEY: MISC_FEATURE
<222> LOCATION: (78)..(109)
<223> OTHER INFORMATION: FR3
<220> FEATURE:
<221> NAME/KEY: MISC_FEATURE
<222> LOCATION: (110)..(118)
<223> OTHER INFORMATION: CDR3
<220> FEATURE:
<221> NAME/KEY: MISC_FEATURE
<222> LOCATION: (119)..(128)
<223> OTHER INFORMATION: FR4

<400> SEQUENCE: 10

```
Met Asp Leu Gln Val Gln Ile Phe Ser Phe Leu Leu Ile Ser Ala Ser
1               5                   10                  15

Val Ile Leu Ser Arg Gly Gln Ile Val Leu Thr Gln Ser Pro Ala Ile
            20                  25                  30

Met Ser Ala Ser Pro Gly Glu Lys Val Thr Met Thr Cys Ser Ala Ser
        35                  40                  45

Ser Ser Ile Ser Tyr Met His Trp Tyr Gln Gln Lys Pro Gly Thr Ser
    50                  55                  60

Pro Lys Arg Trp Ile Tyr Asp Thr Ser Lys Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Ser Met Glu Ala Glu Asp Ala Ala Thr Tyr Tyr Cys His Gln Arg
            100                 105                 110

Ser Ser Tyr Pro Leu Thr Phe Gly Ala Gly Thr Lys Leu Glu Leu Lys
        115                 120                 125
```

<210> SEQ ID NO 11
<211> LENGTH: 134
<212> TYPE: PRT
<213> ORGANISM: Artificial Sequence
<220> FEATURE:
<223> OTHER INFORMATION: 15F9 mAb VH chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(44)
<223> OTHER INFORMATION: FR1
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (55)..(68)
<223> OTHER INFORMATION: FR2
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MISC_FEATURE
<222> LOCATION: (86)..(117)
<223> OTHER INFORMATION: FR3
<220> FEATURE:
<221> NAME/KEY: MISC_FEATURE
<222> LOCATION: (118)..(123)
<223> OTHER INFORMATION: CDR3
<220> FEATURE:
<221> NAME/KEY: MISC_FEATURE
<222> LOCATION: (124)..(134)
<223> OTHER INFORMATION: FR4

<400> SEQUENCE: 11

Met Gly Trp Ser Cys Ile Met Phe Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Asn Tyr Trp Met His Trp Val Lys Gln Arg Pro Gly Gln Gly Leu
    50                  55                  60

Glu Trp Ile Gly Met Ile His Pro Asn Ser Gly Ser Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Arg Gly Asp Gly Asp Tyr Trp Gly Gln Gly Thr
        115                 120                 125

Thr Leu Thr Val Ser Ser
    130

<210> SEQ ID NO 12
<211> LENGTH: 121
<212> TYPE: PRT
<213> ORGANISM: Artificial Sequence
<220> FEATURE:
<223> OTHER INFORMATION: 15F9 mAb VL chain
<220> FEATURE:
<221> NAME/KEY: MISC_FEATURE
<222> LOCATION: (1)..(15)
<223> OTHER INFORMATION: Leader sequence
<220> FEATURE:
<221> NAME/KEY: MISC_FEATURE
<222> LOCATION: (16)..(38)
<223> OTHER INFORMATION: FR1
<220> FEATURE:
<221> NAME/KEY: MISC_FEATURE
<222> LOCATION: (39)..(49)
<223> OTHER INFORMATION: CDR1
<220> FEATURE:
<221> NAME/KEY: MISC_FEATURE
<222> LOCATION: (50)..(64)
<223> OTHER INFORMATION: FR2
<220> FEATURE:
<221> NAME/KEY: MISC_FEATURE
<222> LOCATION: (65)..(71)
<223> OTHER INFORMATION: CDR2
<220> FEATURE:
<221> NAME/KEY: MISC_FEATURE
<222> LOCATION: (72)..(103)
<223> OTHER INFORMATION: FR3
<220> FEATURE:
<221> NAME/KEY: MISC_FEATURE
<222> LOCATION: (104)..(112)
<223> OTHER INFORMATION: CDR3
<220> FEATURE:
<221> NAME/KEY: MISC_FEATURE
<222> LOCATION: (113)..(121)
<223> OTHER INFORMATION: FR4

<400> SEQUENCE: 12

Met Val Leu Ile Ser Leu Leu Phe Trp Phe Pro Gly Thr Arg Cys Asp
1               5                   10                  15

Ile Gln Met Thr Arg His Pro Ser Ser Leu Ser Ala Ser Met Gly Glu
            20                  25                  30

```
Arg Val Ser Leu Thr Cys Arg Ala Ser Gln Glu Ile Ser Gly Tyr Leu
        35                  40                  45

Ser Trp Leu Gln Gln Lys Pro Asp Gly Thr Ile Lys Arg Leu Ile Tyr
    50                  55                  60

Ala Ala Ser Thr Leu Asp Ser Gly Val Pro Lys Arg Phe Ser Gly Ser
65                  70                  75                  80

Arg Ser Gly Ser Asp Tyr Ser Leu Thr Ile Ser Ser Leu Glu Ser Glu
                85                  90                  95

Asp Phe Ala Asp Tyr Tyr Cys Leu Gln Tyr Ala Ser Tyr Pro Tyr Thr
            100                 105                 110

Phe Gly Gly Gly Thr Lys Leu Glu Ile
        115                 120


<210> SEQ ID NO 13
<211> LENGTH: 139
<212> TYPE: PRT
<213> ORGANISM: Artificial Sequence
<220> FEATURE:
<223> OTHER INFORMATION: 8B12 mAb VH chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(44)
<223> OTHER INFORMATION: FR1
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (55)..(68)
<223> OTHER INFORMATION: FR2
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MISC_FEATURE
<222> LOCATION: (86)..(115)
<223> OTHER INFORMATION: FR3
<220> FEATURE:
<221> NAME/KEY: MISC_FEATURE
<222> LOCATION: (116)..(127)
<223> OTHER INFORMATION: CDR3
<220> FEATURE:
<221> NAME/KEY: MISC_FEATURE
<222> LOCATION: (128)..(139)
<223> OTHER INFORMATION: FR4

<400> SEQUENCE: 13

Met Glu Trp Ser Trp Val Ile Leu Ile Leu Val Ala Ala Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Trp Ile Thr Trp Val Lys Gln Arg Pro Gly Gln Gly Leu
    50                  55                  60

Glu Trp Ile Gly Asp Ile Tyr Pro Gly Ser Gly Ser Thr Asn Tyr Asn
65                  70                  75                  80

Glu Lys Phe Lys Ser Lys Ala Thr Leu Thr Val Asp Thr Ser Ser Ser
                85                  90                  95
```

```
Thr Ala Tyr Met Gln Leu Ser Ser Leu Thr Ser Glu Asp Ser Ala Val
            100                 105                 110

Tyr Tyr Cys Ala Arg Gly Gly Thr Arg Phe Ser Pro Phe Ala Tyr Trp
        115                 120                 125

Gly Gln Gly Thr Leu Val Thr Val Ser Ala Ala
    130                 135


<210> SEQ ID NO 14
<211> LENGTH: 135
<212> TYPE: PRT
<213> ORGANISM: Artificial Sequence
<220> FEATURE:
<223> OTHER INFORMATION: 8B12 mAb VL chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(42)
<223> OTHER INFORMATION: FR1
<220> FEATURE:
<221> NAME/KEY: MISC_FEATURE
<222> LOCATION: (43)..(58)
<223> OTHER INFORMATION: CDR1
<220> FEATURE:
<221> NAME/KEY: MISC_FEATURE
<222> LOCATION: (59)..(73)
<223> OTHER INFORMATION: FR2
<220> FEATURE:
<221> NAME/KEY: MISC_FEATURE
<222> LOCATION: (74)..(80)
<223> OTHER INFORMATION: CDR2
<220> FEATURE:
<221> NAME/KEY: MISC_FEATURE
<222> LOCATION: (81)..(112)
<223> OTHER INFORMATION: FR3
<220> FEATURE:
<221> NAME/KEY: MISC_FEATURE
<222> LOCATION: (113)..(121)
<223> OTHER INFORMATION: CDR3
<220> FEATURE:
<221> NAME/KEY: MISC_FEATURE
<222> LOCATION: (122)..(135)
<223> OTHER INFORMATION: FR4

<400> SEQUENCE: 14

Met Lys Met Pro Val Arg Leu Leu Val Leu Met Phe Trp Ile Pro Ala
1               5                   10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Trp Thr Phe Gly Gly Gly Thr Lys Leu
        115                 120                 125

Glu Ile Lys Arg Ala Asp Ala
    130                 135
```

<210> SEQ ID NO 15
<211> LENGTH: 138
<212> TYPE: PRT
<213> ORGANISM: Artificial Sequence
<220> FEATURE:
<223> OTHER INFORMATION: 12B4 mAb VH chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(44)
<223> OTHER INFORMATION: FR1
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (55)..(68)
<223> OTHER INFORMATION: FR2
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MISC_FEATURE
<222> LOCATION: (86)..(117)
<223> OTHER INFORMATION: FR3
<220> FEATURE:
<221> NAME/KEY: MISC_FEATURE
<222> LOCATION: (118)..(128)
<223> OTHER INFORMATION: CDR3
<220> FEATURE:
<221> NAME/KEY: MISC_FEATURE
<222> LOCATION: (129)..(138)
<223> OTHER INFORMATION: FR4

<400> SEQUENCE: 15

```
Met Gly Trp Ser Cys Ile Met Phe Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Met Ile His Pro Asn Ser Gly Ser Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Tyr Tyr Tyr Gly Ser Ser Tyr Ala Met Asp Tyr
        115                 120                 125

Trp Gly Gln Gly Thr Ser Val Thr Val Ser
    130                 135
```

<210> SEQ ID NO 16
<211> LENGTH: 131
<212> TYPE: PRT
<213> ORGANISM: Artificial Sequence
<220> FEATURE:
<223> OTHER INFORMATION: 12B4 mAb VL chain
<220> FEATURE:
<221> NAME/KEY: MISC_FEATURE
<222> LOCATION: (1)..(22)
<223> OTHER INFORMATION: Leader sequence
<220> FEATURE:
<221> NAME/KEY: MISC_FEATURE
<222> LOCATION: (23)..(45)
<223> OTHER INFORMATION: FR1
<220> FEATURE:
<221> NAME/KEY: MISC_FEATURE
<222> LOCATION: (46)..(55)
<223> OTHER INFORMATION: CDR1
<220> FEATURE:
<221> NAME/KEY: MISC_FEATURE
<222> LOCATION: (56)..(70)
<223> OTHER INFORMATION: FR2
<220> FEATURE:
<221> NAME/KEY: MISC_FEATURE
<222> LOCATION: (71)..(77)
<223> OTHER INFORMATION: CDR2
<220> FEATURE:
<221> NAME/KEY: MISC_FEATURE
<222> LOCATION: (78)..(109)
<223> OTHER INFORMATION: FR3
<220> FEATURE:
<221> NAME/KEY: MISC_FEATURE
<222> LOCATION: (110)..(118)
<223> OTHER INFORMATION: CDR3
<220> FEATURE:
<221> NAME/KEY: MISC_FEATURE
<222> LOCATION: (119)..(131)
<223> OTHER INFORMATION: FR4

<400> SEQUENCE: 16

```
Met Asp Phe Gln Val Gln Ile Phe Ser Phe Leu Leu Ile Ser Ala Ser
1               5                   10                  15

Val Ile Met Ser Arg Gly Gln Ile Val Leu Thr Gln Ser Pro Ala Ile
            20                  25                  30

Met Ser Ala Ser Pro Gly Glu Lys Val Thr Ile Thr Cys Ser Ala Ser
        35                  40                  45

Ser Ser Val Ser Tyr Met His Trp Phe Gln Gln Lys Pro Gly Thr Ser
    50                  55                  60

Pro Lys Leu Trp Ile Tyr Ser Thr Ser Asn Leu Ala Ser Gly Val Pro
65                  70                  75                  80

Ala Arg Phe Ser Gly Ser Gly Ser Gly Thr Ser Tyr Ser Leu Thr Ile
                85                  90                  95

Ser Arg Met Glu Ala Glu Asp Ala Ala Thr Tyr Tyr Cys Gln Gln Arg
            100                 105                 110

Ser Ser Tyr Pro Tyr Thr Phe Gly Gly Gly Thr Lys Leu Glu Ile Lys
        115                 120                 125

Arg Ala Asp
    130
```

<210> SEQ ID NO 17
<211> LENGTH: 133
<212> TYPE: PRT
<213> ORGANISM: Artificial Sequence
<220> FEATURE:
<223> OTHER INFORMATION: 24D12 mAb VH chain
<220> FEATURE:
<221> NAME/KEY: MISC_FEATURE
<222> LOCATION: (1)..(19)
<223> OTHER INFORMATION: Leader sequence
<220> FEATURE:
<221> NAME/KEY: MISC_FEATURE
<222> LOCATION: (20)..(44)
<223> OTHER INFORMATION: FR1
<220> FEATURE:
<221> NAME/KEY: MISC_FEATURE
<222> LOCATION: (45)..(54)
<223> OTHER INFORMATION: CDR1
<220> FEATURE:
<221> NAME/KEY: MISC_FEATURE
<222> LOCATION: (55)..(68)
<223> OTHER INFORMATION: FR2
<220> FEATURE:
<221> NAME/KEY: MISC_FEATURE
<222> LOCATION: (69)..(85)
<223> OTHER INFORMATION: CDR2
<220> FEATURE:
<221> NAME/KEY: MISC_FEATURE
<222> LOCATION: (86)..(117)
<223> OTHER INFORMATION: FR3
<220> FEATURE:
<221> NAME/KEY: MISC_FEATURE
<222> LOCATION: (118)..(123)
<223> OTHER INFORMATION: CDR3
<220> FEATURE:
<221> NAME/KEY: MISC_FEATURE
<222> LOCATION: (124)..(133)
<223> OTHER INFORMATION: FR4

<400> SEQUENCE: 17

```
Met Gly Trp Ser Cys Ile Met Phe Phe Leu Val Ala Thr Ala Thr Gly
1               5                   10                  15

Val His Ser Gln Val Gln Leu Gln Gln Pro Gly Ala Glu Leu Val Lys
            20                  25                  30

Pro Gly Ala Ser Val Lys Leu Ser Cys Lys Ala Ser Gly Tyr Thr Phe
        35                  40                  45

Thr Ser Tyr Trp Met His Trp Val Lys Gln Arg Pro Gly Gln Gly Leu
    50                  55                  60

Glu Trp Ile Gly Met Ile His Pro Asn Ser Gly Ser Thr Asn Tyr Asn
65                  70                  75                  80

Glu Lys Phe Lys Ser Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Asn Tyr Tyr Gly Thr Asn Val Trp Gly Thr Gly Thr
        115                 120                 125

Thr Val Thr Val Ser
    130
```

<210> SEQ ID NO 18
<211> LENGTH: 129
<212> TYPE: PRT
<213> ORGANISM: Artificial Sequence
<220> FEATURE:
<223> OTHER INFORMATION: 24D12 mAb VL chain
<220> FEATURE:
<221> NAME/KEY: MISC_FEATURE
<222> LOCATION: (1)..(20)
<223> OTHER INFORMATION: Leader sequence
<220> FEATURE:
<221> NAME/KEY: MISC_FEATURE
<222> LOCATION: (21)..(46)
<223> OTHER INFORMATION: FR1
<220> FEATURE:
<221> NAME/KEY: MISC_FEATURE
<222> LOCATION: (47)..(58)
<223> OTHER INFORMATION: CDR1
<220> FEATURE:
<221> NAME/KEY: MISC_FEATURE
<222> LOCATION: (59)..(73)
<223> OTHER INFORMATION: FR2
<220> FEATURE:
<221> NAME/KEY: MISC_FEATURE
<222> LOCATION: (74)..(80)
<223> OTHER INFORMATION: CDR2
<220> FEATURE:
<221> NAME/KEY: MISC_FEATURE
<222> LOCATION: (81)..(112)
<223> OTHER INFORMATION: FR3

<220> FEATURE:
<221> NAME/KEY: MISC_FEATURE
<222> LOCATION: (113)..(120)
<223> OTHER INFORMATION: CDR3
<220> FEATURE:
<221> NAME/KEY: MISC_FEATURE
<222> LOCATION: (121)..(129)
<223> OTHER INFORMATION: FR4

<400> SEQUENCE: 18

```
Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Ala Tyr Thr Phe Gly Arg Gly Asp Gln Ser Trp
        115                 120                 125

Lys
```

<210> SEQ ID NO 19
<211> LENGTH: 207
<212> TYPE: DNA
<213> ORGANISM: Homo sapiens

<400> SEQUENCE: 19

```
accacgacgc cagcgccgcg accaccaaca ccggcgccca ccatcgcgtc gcagcccctg     60

tccctgcgcc cagaggcgtg ccggccagcg gcggggggcg cagtgcacac gagggggctg    120

gacttcgcct gtgatatcta catctgggcg cccttggccg ggacttgtgg ggtccttctc    180

ctgtcactgg ttatcaccct ttactgc                                        207
```

<210> SEQ ID NO 20
<211> LENGTH: 123
<212> TYPE: DNA
<213> ORGANISM: Homo sapiens

<400> SEQUENCE: 20

```
aggagtaaga ggagcaggct cctgcacagt gactacatga acatgactcc ccgccgcccc     60

gggcccaccc gcaagcatta ccagccctat gccccaccac gcgacttcgc agcctatcgc    120

tcc                                                                  123
```

<210> SEQ ID NO 21
<211> LENGTH: 126
<212> TYPE: DNA
<213> ORGANISM: Homo sapiens

<400> SEQUENCE: 21
aaacggggca gaaagaaact cctgtatata ttcaaacaac catttatgag accagtacaa 60
actactcaag aggaagatgg ctgtagctgc cgatttccag aagaagaaga aggaggatgt 120
gaactg 126

<210> SEQ ID NO 22
<211> LENGTH: 342
<212> TYPE: DNA
<213> ORGANISM: Homo sapiens

<400> SEQUENCE: 22
agagtgaagt tcagcaggag cgcagacgcc cccgcgtacc agcagggcca gaaccagctc 60
tataacgagc tcaatctagg acgaagagag gagtacgatg ttttggacaa gagacgtggc 120
cgggaccctg agatgggggg aaagccgcag agaaggaaga accctcagga aggcctgtac 180
aatgaactgc agaaagataa gatggcggag gcctacagtg agattgggat gaaaggcgag 240
cgccggaggg gcaaggggca cgatggcctt taccagggtc tcagtacagc caccaaggac 300
acctacgacg cccttcacat gcaggccctg ccccctcgct aa 342

<210> SEQ ID NO 23
<211> LENGTH: 66
<212> TYPE: DNA
<213> ORGANISM: Homo sapiens

<400> SEQUENCE: 23
ggaagcggag ctactaactt cagcctgctg aagcaggctg gagacgtgga ggagaaccct 60
ggacct 66

<210> SEQ ID NO 24
<211> LENGTH: 1005
<212> TYPE: DNA
<213> ORGANISM: Homo sapiens

<400> SEQUENCE: 24
cgcaaagtgt gtaacggaat aggtattggt gaatttaaag actcactctc cataaatgct 60
acgaatatta aacacttcaa aaactgcacc tccatcagtg gcgatctcca catcctgccg 120
gtggcattta ggggtgactc cttcacacat actcctcctc tggatccaca ggaactggat 180
attctgaaaa ccgtaaagga aatcacaggg tttttgctga ttcaggcttg gcctgaaaac 240
aggacggacc tccatgcctt tgagaaccta gaaatcatac gcggcaggac caagcaacat 300
ggtcagtttt ctcttgcagt cgtcagcctg aacataacat ccttgggatt acgctccctc 360
aaggagataa gtgatggaga tgtgataatt tcaggaaaca aaaatttgtg ctatgcaaat 420
acaataaact ggaaaaaact gtttgggacc tccggtcaga aaaccaaaat tataagcaac 480
agaggtgaaa acagctgcaa ggccacaggc caggtctgcc atgccttgtg ctcccccgag 540
ggctgctggg gcccggagcc cagggactgc gtctcttgcc ggaatgtcag ccgaggcagg 600
gaatgcgtgg acaagtgcaa ccttctggag ggtgagccaa gggagtttgt ggagaactct 660
gagtgcatac agtgccaccc agagtgcctg cctcaggcca tgaacatcac ctgcacagga 720
cggggaccag acaactgtat ccagtgtgcc cactacattg acggccccca ctgcgtcaag 780
acctgcccgg caggagtcat gggagaaaac aacaccctgg tctggaagta cgcagacgcc 840
ggccatgtgt gccacctgtg ccatccaaac tgcacctacg gatgcactgg gccaggtctt 900

```
gaaggctgtc caacgaatgg gcctaagatc ccgtccatcg ccactgggat ggtgggggcc     960

ctcctcttgc tgctggtggt ggccctgggg atcggcctct tcatg                    1005


<210> SEQ ID NO 25
<211> LENGTH: 402
<212> TYPE: DNA
<213> ORGANISM: Artificial Sequence
<220> FEATURE:
<223> OTHER INFORMATION: 1G5 mAb VH chain

<400> SEQUENCE: 25

atgggatgga gctatatcat cctctttttg gtagcaacag ctacaggtgt ccactcccag      60

gtccaactgc agcagcctgg ggctgagctg gtaaagcctg gggcttcagt gaagttgtcc     120

tgcaaggctt ctggctacac tttcaccagc tactggatgc actgggtgaa gcagaggcct     180

ggacaaggcc ttgagtggat tggaatgatt catcctaata gtggtagtac taactacaat     240

gagaagttca agagcaaggc cacactgact gtagacaaat cctccagcac agcctacatg     300

caactcagca gcctgacatc tgaggactct gcggtctatt actgtgcaag gggggggtac     360

tttgactact ggggccaagg caccactctc acagtctcct ca                        402


<210> SEQ ID NO 26
<211> LENGTH: 384
<212> TYPE: DNA
<213> ORGANISM: Artificial Sequence
<220> FEATURE:
<223> OTHER INFORMATION: 1G5 mAb VL chain

<400> SEQUENCE: 26

atgaagacac agactcaggt ctttgtatac atgttgctgt ggttgtctgg tgttgatgga      60

gacattgtga tgacccagtc tcaaaaattc atgtccacat cagtaggaga cagggtcagc     120

gtcacctgca aggccagtca gaatgtgggt actaatgtag cctggtatca acagaaacca     180

gggcaatctc ctaaagcact gatttactcg gcatcctacc ggtacagtgg agtccctgat     240

cgcttcacag gcagtggatc tgggacagat ttcactctca ccatcagcaa tgtgcagtct     300

gaagacttgg cagagtattt ctgtcagcaa tataacagct atccgtacac gttcggaggg     360

gggaccaagc tggaaataaa acgg                                            384


<210> SEQ ID NO 27
<211> LENGTH: 405
<212> TYPE: DNA
<213> ORGANISM: Artificial Sequence
<220> FEATURE:
<223> OTHER INFORMATION: 23B2 mAb VL chain

<400> SEQUENCE: 27

atgggatgga gctgtatcat gctctttttg gtagcaacag ctacaggtgt ccactcccag      60

gtccaactgc agcagcctgg ggctgagctg gtaaagcctg gggcttcagt gaagttgtcc     120

tgcaaggctt ctggctacac tttcaccagc tactggatgc actgggtgaa gcagaggcct     180

ggacaaggcc ttgagtggat tggaatgatt catcctaata gtggtagtac taactacaat     240

gagaagttca agagcaaggc cacactgact gtagacaaat cctccagcac agcctacatg     300

caactcagca gcctgacatc tgaggactct gcggtctatt actgtgcaag agagagtaga     360

cagctcgact actggggcca aggcaccact ctcacagtct cctca                     405


<210> SEQ ID NO 28
<211> LENGTH: 384
```

```
<212> TYPE: DNA
<213> ORGANISM: Artificial Sequence
<220> FEATURE:
<223> OTHER INFORMATION: 23B2 mAb VL chain

<400> SEQUENCE: 28

atggatttac aagtgcagat tttcagcttc ctgctaatca gtgcctcagt catactgtcc     60

agaggacaaa ttgttctcac ccagtctcca gcaatcatgt ctgcatctcc aggggagaag    120

gtcaccatga cctgcagtgc cagctcaagt ataagttaca tgcactggta ccagcagaag    180

ccaggcacct cccccaaaag atggatttat gacacatcca aactggcttc tggagtccct    240

gctcgcttca gtggcagtgg gtctgggacc tcttattctc tcacaatcag cagcatggag    300

gctgaagatg ctgccactta ttactgccat cagcggagta gttacccgct cacgttcggt    360

gctgggacca agctggagct gaaa                                           384


<210> SEQ ID NO 29
<211> LENGTH: 403
<212> TYPE: DNA
<213> ORGANISM: Artificial Sequence
<220> FEATURE:
<223> OTHER INFORMATION: 15F9 mAb VH chain

<400> SEQUENCE: 29

atgggatgga gctgtatcat gttctttttg gtagcaacag ctacaggtgt ccactcccag     60

gtccaactgc agcagcctgg ggctgagctg gtaaagcctg gggcttcagt gaagttgtcc    120

tgcaaggctt ctggctacac tttcaccaac tactggatgc actgggtgaa gcagaggcct    180

ggacaaggcc ttgagtggat tggaatgatt catcctaata gtggtagtac taactacaat    240

gagaagttca agagcaaggc cacactgact gtagacaaat cctccagcac agcctacatg    300

caactcagca gcctgacatc tgaggactct gcggtctatt actgtgcaag gcgaggggac    360

ggggactact ggggccaagg caccactctc acagtctcct cag                      403


<210> SEQ ID NO 30
<211> LENGTH: 363
<212> TYPE: DNA
<213> ORGANISM: Artificial Sequence
<220> FEATURE:
<223> OTHER INFORMATION: 15F9 mAb VL chain

<400> SEQUENCE: 30

atggttctta tttccttgct gttctggttt ccaggtacca gatgtgacat ccagatgacc     60

cggcatcctt cttctttatc tgcctctatg ggagaaagag tcagtctcac ttgtcgggca    120

agtcaggaaa ttagtggtta cttaagctgg cttcagcaga aaccagatgg aactattaaa    180

cgcctgattt acgccgcatc cactttagat tctggtgtcc caaaaaggtt cagtggcagt    240

aggtctgggt cagattattc tctcaccatc agcagccttg agtctgaaga ttttgcagac    300

tattactgtc tacaatatgc tagttatccg tacacgttcg gaggggggac caagctggaa    360

ata                                                                  363


<210> SEQ ID NO 31
<211> LENGTH: 419
<212> TYPE: DNA
<213> ORGANISM: Artificial Sequence
<220> FEATURE:
<223> OTHER INFORMATION: 8B12 mAb VH chain
```

<400> SEQUENCE: 31
atggaatgga gctgggtcat cctcattttg gtagcagcag ctacaggtgt ccactcccag 60
gtccaactgc agcagcctgg ggctgagctt gtgaagcctg gggcttcagt gaagatgtcc 120
tgcaaggctt ctggctacac cttcaccagc tactggataa cctgggtgaa gcagaggcct 180
ggacaaggcc ttgagtggat tggagatatt tatcctggta gtggtagtac taactacaat 240
gagaagttca agagcaaggc cactctgact gtagacacat cctccagcac agcctacatg 300
cagctcagca gcctgacatc tgaggactct gcggtctatt actgtgcaag agggggtact 360
agattcagcc cctttgctta ctggggccaa gggactctgg tcactgtctc tgcagctac 419

<210> SEQ ID NO 32
<211> LENGTH: 405
<212> TYPE: DNA
<213> ORGANISM: Artificial Sequence
<220> FEATURE:
<223> OTHER INFORMATION: 8B12 mAb VL chain

<400> SEQUENCE: 32
atgaagatgc ctgttaggct gttggtgctg atgttctgga ttcctgcttc cagcagtgat 60
gttttgatga cccaaactcc actctccctg cctgtcagtc ttggagatca agcctccatc 120
tcttgcagat ctagtcagag cattgtacat agtaatggaa acacctattt agaatggtac 180
ctgcagaaac caggccagtc tccaaagctc ctgatctaca aagtttccaa ccgattttct 240
ggggtcccag acaggttcag tggcagtgga tcagggacag atttcacact caagatcagc 300
agagtggagg ctgaggatct gggagtttat tactgctttc aaggttcaca tgttccgtgg 360
acgttcggtg gaggcaccaa gctggaaatc aaacgggctg atgct 405

<210> SEQ ID NO 33
<211> LENGTH: 416
<212> TYPE: DNA
<213> ORGANISM: Artificial Sequence
<220> FEATURE:
<223> OTHER INFORMATION: 12B4 mAb VH chain

<400> SEQUENCE: 33
atgggatgga gctgtatcat gttctttttg gtagcaacag ctacaggtgt ccactcccag 60
gtccaactgc agcagcctgg ggctgagctg gtaaagcctg gggcttcagt gaagttgtcc 120
tgcaaggctt ctggctacac tttcaccagc tactggatgc actgggtgaa gcagaggcct 180
ggacaaggcc ttgagtggat tggaatgatt catcctaata gtggtagtac taactacaat 240
gagaagttca agagcaaggc cacactgact gtagacaaat cctccagcac agcctacatg 300
caactcagca gcctgacatc tgaggactct gcggtctatt actgtgcaag atattactac 360
ggtagtagct atgctatgga ctactggggt caaggaacct cagtcaccgt ctctca 416

<210> SEQ ID NO 34
<211> LENGTH: 394
<212> TYPE: DNA
<213> ORGANISM: Artificial Sequence
<220> FEATURE:
<223> OTHER INFORMATION: 12B4 mAb VL chain

<400> SEQUENCE: 34
atggattttc aggtgcagat tttcagcttc ctgctaatca gtgcctcagt cataatgtcc 60
agaggacaaa ttgttctcac ccagtctcca gcaatcatgt ctgcatctcc aggggagaag 120
gtcaccataa cctgcagtgc cagctcaagt gtaagttaca tgcactggtt ccagcagaag 180
ccaggcactt ctcccaaact ctggatttat agcacatcca acctggcttc tggagtccct 240
gctcgcttca gtggcagtgg atctgggacc tcttactctc tcacaatcag ccgaatggag 300
gctgaagatg ctgccactta ttactgccag caaaggagta gttacccgta cacgttcgga 360
ggggggacca agctggaaat aaaacgggct gatg 394

<210> SEQ ID NO 35
<211> LENGTH: 399
<212> TYPE: DNA
<213> ORGANISM: Artificial Sequence
<220> FEATURE:
<223> OTHER INFORMATION: 24D12 mAb VH chain

<400> SEQUENCE: 35
atgggatgga gctgtatcat gttctttttg gtagcaacag ctacaggtgt ccactcccag 60
gtccaactgc agcagcctgg ggctgagctg gtaaagcctg gggcttcagt gaagttgtcc 120
tgcaaggctt ctggctacac tttcaccagc tactggatgc actgggtgaa gcagaggcct 180
ggacaaggcc ttgagtggat tggaatgatt catcctaata gtggtagtac taactacaat 240
gagaagttca agagcaaggc cacactgact gtagacaaat cctccagcac agcctacatg 300
caactcagca gcctgacatc tgaggactct gcggtctatt actgtgcaaa ttactacggt 360
actaatgtct ggggcacagg gaccacggtc accgtctct 399

<210> SEQ ID NO 36
<211> LENGTH: 387
<212> TYPE: DNA
<213> ORGANISM: Artificial Sequence
<220> FEATURE:
<223> OTHER INFORMATION: 24D12 mAb VL chain

<400> SEQUENCE: 36
atggagacag acacactgct gctatgggta ctgctgctct gggttccagg ttccactggt 60
gacattgtgc tgacacagtc tcctgcttcc ttagctgtat ctctggggca gagggccacc 120
atctcataca gggccagcaa aagtgtcagt acatctggct atagttatat gcactggaac 180
caacagaaac caggacagcc acccagactc ctcatctatc ttgtatccaa cctagaatct 240
ggggtccctg ccaggttcag tggcagtggg tctgggacag acttcaccct caacatccat 300
cctgtggagg aggaggatgc tgcaacctat tactgtcagc acattaggga agcttacacg 360
ttcggaaggg gggaccaaag ctggaaa 387

<210> SEQ ID NO 37
<211> LENGTH: 10
<212> TYPE: PRT
<213> ORGANISM: Artificial Sequence
<220> FEATURE:
<223> OTHER INFORMATION: VH CDR1

<400> SEQUENCE: 37

Gly Tyr Thr Phe Thr Ser Tyr Trp Met His
1 5 10

<210> SEQ ID NO 38
<211> LENGTH: 10
<212> TYPE: PRT
<213> ORGANISM: Artificial Sequence
<220> FEATURE:
<223> OTHER INFORMATION: VH CDR1

<400> SEQUENCE: 38

Gly Tyr Thr Phe Thr Asn Tyr Trp Met His
1               5                   10

<210> SEQ ID NO 39
<211> LENGTH: 10
<212> TYPE: PRT
<213> ORGANISM: Artificial Sequence
<220> FEATURE:
<223> OTHER INFORMATION: VH CDR1

<400> SEQUENCE: 39

Gly Tyr Thr Phe Thr Ser Tyr Trp Ile Thr
1               5                   10

<210> SEQ ID NO 40
<211> LENGTH: 11
<212> TYPE: PRT
<213> ORGANISM: Artificial Sequence
<220> FEATURE:
<223> OTHER INFORMATION: VL CDR1

<400> SEQUENCE: 40

Lys Ala Ser Gln Asn Val Gly Thr Asn Val Ala
1               5                   10

<210> SEQ ID NO 41
<211> LENGTH: 10
<212> TYPE: PRT
<213> ORGANISM: Artificial Sequence
<220> FEATURE:
<223> OTHER INFORMATION: VL CDR1

<400> SEQUENCE: 41

Ser Ala Ser Ser Ser Ile Ser Tyr Met His
1               5                   10

<210> SEQ ID NO 42
<211> LENGTH: 11
<212> TYPE: PRT
<213> ORGANISM: Artificial Sequence
<220> FEATURE:
<223> OTHER INFORMATION: VL CDR1

<400> SEQUENCE: 42

Arg Ala Ser Gln Glu Ile Ser Gly Tyr Leu Ser
1               5                   10

<210> SEQ ID NO 43
<211> LENGTH: 16
<212> TYPE: PRT
<213> ORGANISM: Artificial Sequence
<220> FEATURE:
<223> OTHER INFORMATION: VL CDR1

<400> SEQUENCE: 43

Arg Ser Ser Gln Ser Ile Val His Ser Asn Gly Asn Thr Tyr Leu Glu
1               5                   10                  15

<210> SEQ ID NO 44
<211> LENGTH: 10
<212> TYPE: PRT
<213> ORGANISM: Artificial Sequence
<220> FEATURE:
<223> OTHER INFORMATION: VL CDR1

<400> SEQUENCE: 44

Ser Ala Ser Ser Ser Val Ser Tyr Met His
1 5 10

<210> SEQ ID NO 45
<211> LENGTH: 12
<212> TYPE: PRT
<213> ORGANISM: Artificial Sequence
<220> FEATURE:
<223> OTHER INFORMATION: VL CDR1

<400> SEQUENCE: 45

Lys Ser Val Ser Thr Ser Gly Tyr Ser Tyr Met His
1 5 10

<210> SEQ ID NO 46
<211> LENGTH: 17
<212> TYPE: PRT
<213> ORGANISM: Artificial Sequence
<220> FEATURE:
<223> OTHER INFORMATION: VH CDR2

<400> SEQUENCE: 46

Met Ile His Pro Asn Ser Gly Ser Thr Asn Tyr Asn Glu Lys Phe Lys
1 5 10 15

Ser

<210> SEQ ID NO 47
<211> LENGTH: 17
<212> TYPE: PRT
<213> ORGANISM: Artificial Sequence
<220> FEATURE:
<223> OTHER INFORMATION: VH CDR2

<400> SEQUENCE: 47

Asp Ile Tyr Pro Gly Ser Gly Ser Thr Asn Tyr Asn Glu Lys Phe Lys
1 5 10 15

Ser

<210> SEQ ID NO 48
<211> LENGTH: 7
<212> TYPE: PRT
<213> ORGANISM: Artificial Sequence
<220> FEATURE:
<223> OTHER INFORMATION: VL CDR2

<400> SEQUENCE: 48

Ser Ala Ser Tyr Arg Tyr Ser
1 5

<210> SEQ ID NO 49
<211> LENGTH: 7
<212> TYPE: PRT
<213> ORGANISM: Artificial Sequence
<220> FEATURE:
<223> OTHER INFORMATION: VL CDR2

<400> SEQUENCE: 49

Asp Thr Ser Lys Leu Ala Ser
1 5

<210> SEQ ID NO 50
<211> LENGTH: 7
<212> TYPE: PRT

```
<213> ORGANISM: Artificial Sequence
<220> FEATURE:
<223> OTHER INFORMATION: VL CDR2

<400> SEQUENCE: 50

Ala Ala Ser Thr Leu Asp Ser
1               5


<210> SEQ ID NO 51
<211> LENGTH: 7
<212> TYPE: PRT
<213> ORGANISM: Artificial Sequence
<220> FEATURE:
<223> OTHER INFORMATION: VL CDR2

<400> SEQUENCE: 51

Lys Val Ser Asn Arg Phe Ser
1               5


<210> SEQ ID NO 52
<211> LENGTH: 7
<212> TYPE: PRT
<213> ORGANISM: Artificial Sequence
<220> FEATURE:
<223> OTHER INFORMATION: VL CDR2

<400> SEQUENCE: 52

Ser Thr Ser Asn Leu Ala Ser
1               5


<210> SEQ ID NO 53
<211> LENGTH: 7
<212> TYPE: PRT
<213> ORGANISM: Artificial Sequence
<220> FEATURE:
<223> OTHER INFORMATION: VL CDR2

<400> SEQUENCE: 53

Leu Val Ser Asn Leu Glu Ser
1               5


<210> SEQ ID NO 54
<211> LENGTH: 6
<212> TYPE: PRT
<213> ORGANISM: Artificial Sequence
<220> FEATURE:
<223> OTHER INFORMATION: VH CDR3

<400> SEQUENCE: 54

Gly Gly Tyr Phe Asp Tyr
1               5


<210> SEQ ID NO 55
<211> LENGTH: 9
<212> TYPE: PRT
<213> ORGANISM: Artificial Sequence
<220> FEATURE:
<223> OTHER INFORMATION: VH CDR3

<400> SEQUENCE: 55

Ala Arg Glu Ser Arg Gln Leu Asp Tyr
1               5


<210> SEQ ID NO 56
<211> LENGTH: 6
<212> TYPE: PRT
<213> ORGANISM: Artificial Sequence
```

```
<220> FEATURE:
<223> OTHER INFORMATION: VH CDR3

<400> SEQUENCE: 56

Arg Gly Asp Gly Asp Tyr
1               5


<210> SEQ ID NO 57
<211> LENGTH: 12
<212> TYPE: PRT
<213> ORGANISM: Artificial Sequence
<220> FEATURE:
<223> OTHER INFORMATION: VH CDR3

<400> SEQUENCE: 57

Ala Arg Gly Gly Thr Arg Phe Ser Pro Phe Ala Tyr
1               5                   10


<210> SEQ ID NO 58
<211> LENGTH: 11
<212> TYPE: PRT
<213> ORGANISM: Artificial Sequence
<220> FEATURE:
<223> OTHER INFORMATION: VH CDR3

<400> SEQUENCE: 58

Tyr Tyr Tyr Gly Ser Ser Tyr Ala Met Asp Tyr
1               5                   10


<210> SEQ ID NO 59
<211> LENGTH: 6
<212> TYPE: PRT
<213> ORGANISM: Artificial Sequence
<220> FEATURE:
<223> OTHER INFORMATION: VH CDR3

<400> SEQUENCE: 59

Tyr Tyr Gly Thr Asn Val
1               5


<210> SEQ ID NO 60
<211> LENGTH: 9
<212> TYPE: PRT
<213> ORGANISM: Artificial Sequence
<220> FEATURE:
<223> OTHER INFORMATION: VL CDR3

<400> SEQUENCE: 60

Gln Gln Tyr Asn Ser Tyr Pro Tyr Thr
1               5


<210> SEQ ID NO 61
<211> LENGTH: 9
<212> TYPE: PRT
<213> ORGANISM: Artificial Sequence
<220> FEATURE:
<223> OTHER INFORMATION: VL CDR3

<400> SEQUENCE: 61

His Gln Arg Ser Ser Tyr Pro Leu Thr
1               5


<210> SEQ ID NO 62
<211> LENGTH: 9
<212> TYPE: PRT
<213> ORGANISM: Artificial Sequence
<220> FEATURE:
```

<223> OTHER INFORMATION: VL CDR3

<400> SEQUENCE: 62

Leu Gln Tyr Ala Ser Tyr Pro Tyr Thr
1 5

<210> SEQ ID NO 63
<211> LENGTH: 9
<212> TYPE: PRT
<213> ORGANISM: Artificial Sequence
<220> FEATURE:
<223> OTHER INFORMATION: VL CDR3

<400> SEQUENCE: 63

Phe Gln Gly Ser His Val Pro Trp Thr
1 5

<210> SEQ ID NO 64
<211> LENGTH: 9
<212> TYPE: PRT
<213> ORGANISM: Artificial Sequence
<220> FEATURE:
<223> OTHER INFORMATION: VL CDR3

<400> SEQUENCE: 64

Gln Gln Arg Ser Ser Tyr Pro Tyr Thr
1 5

<210> SEQ ID NO 65
<211> LENGTH: 8
<212> TYPE: PRT
<213> ORGANISM: Artificial Sequence
<220> FEATURE:
<223> OTHER INFORMATION: VL CDR3

<400> SEQUENCE: 65

Gln His Ile Arg Glu Ala Tyr Thr
1 5

<210> SEQ ID NO 66
<211> LENGTH: 25
<212> TYPE: PRT
<213> ORGANISM: Artificial Sequence
<220> FEATURE:
<223> OTHER INFORMATION: VH FR1

<400> SEQUENCE: 66

Gln Val Gln Leu Gln Gln Pro Gly Ala Glu Leu Val Lys Pro Gly Ala
1 5 10 15

Ser Val Lys Leu Ser Cys Lys Ala Ser
20 25

<210> SEQ ID NO 67
<211> LENGTH: 25
<212> TYPE: PRT
<213> ORGANISM: Artificial Sequence
<220> FEATURE:
<223> OTHER INFORMATION: VH FR1

<400> SEQUENCE: 67

Gln Val Gln Leu Gln Gln Pro Gly Ala Glu Leu Val Lys Pro Gly Ala
1 5 10 15

Ser Val Lys Met Ser Cys Lys Ala Ser
20 25

<210> SEQ ID NO 68
<211> LENGTH: 23
<212> TYPE: PRT
<213> ORGANISM: Artificial Sequence
<220> FEATURE:
<223> OTHER INFORMATION: VL FR1

<400> SEQUENCE: 68

```
Asp Ile Val Met Thr Gln Ser Gln Lys Phe Met Ser Thr Ser Val Gly
1               5                   10                  15

Asp Arg Val Ser Val Thr Cys
            20
```

<210> SEQ ID NO 69
<211> LENGTH: 23
<212> TYPE: PRT
<213> ORGANISM: Artificial Sequence
<220> FEATURE:
<223> OTHER INFORMATION: VL FR1

<400> SEQUENCE: 69

```
Gln Ile Val Leu Thr Gln Ser Pro Ala Ile Met Ser Ala Ser Pro Gly
1               5                   10                  15

Glu Lys Val Thr Met Thr Cys
            20
```

<210> SEQ ID NO 70
<211> LENGTH: 23
<212> TYPE: PRT
<213> ORGANISM: Artificial Sequence
<220> FEATURE:
<223> OTHER INFORMATION: VL FR1

<400> SEQUENCE: 70

```
Asp Ile Gln Met Thr Arg His Pro Ser Ser Leu Ser Ala Ser Met Gly
1               5                   10                  15

Glu Arg Val Ser Leu Thr Cys
            20
```

<210> SEQ ID NO 71
<211> LENGTH: 23
<212> TYPE: PRT
<213> ORGANISM: Artificial Sequence
<220> FEATURE:
<223> OTHER INFORMATION: VL FR1

<400> SEQUENCE: 71

```
Asp Val Leu Met Thr Gln Thr Pro Leu Ser Leu Pro Val Ser Leu Gly
1               5                   10                  15

Asp Gln Ala Ser Ile Ser Cys
            20
```

<210> SEQ ID NO 72
<211> LENGTH: 23
<212> TYPE: PRT
<213> ORGANISM: Artificial Sequence
<220> FEATURE:
<223> OTHER INFORMATION: VL FR1

<400> SEQUENCE: 72

```
Gln Ile Val Leu Thr Gln Ser Pro Ala Ile Met Ser Ala Ser Pro Gly
1               5                   10                  15

Glu Lys Val Thr Ile Thr Cys
            20
```

<210> SEQ ID NO 73
<211> LENGTH: 26
<212> TYPE: PRT
<213> ORGANISM: Artificial Sequence
<220> FEATURE:
<223> OTHER INFORMATION: VL FR1

<400> SEQUENCE: 73

Asp Ile Val Leu Thr Gln Ser Pro Ala Ser Leu Ala Val Ser Leu Gly
1 5 10 15

Gln Arg Ala Thr Ile Ser Tyr Arg Ala Ser
20 25

<210> SEQ ID NO 74
<211> LENGTH: 14
<212> TYPE: PRT
<213> ORGANISM: Artificial Sequence
<220> FEATURE:
<223> OTHER INFORMATION: VH FR2

<400> SEQUENCE: 74

Trp Val Lys Gln Arg Pro Gly Gln Gly Leu Glu Trp Ile Gly
1 5 10

<210> SEQ ID NO 75
<211> LENGTH: 15
<212> TYPE: PRT
<213> ORGANISM: Artificial Sequence
<220> FEATURE:
<223> OTHER INFORMATION: VL FR2

<400> SEQUENCE: 75

Trp Tyr Gln Gln Lys Pro Gly Gln Ser Pro Lys Ala Leu Ile Tyr
1 5 10 15

<210> SEQ ID NO 76
<211> LENGTH: 15
<212> TYPE: PRT
<213> ORGANISM: Artificial Sequence
<220> FEATURE:
<223> OTHER INFORMATION: VL FR2

<400> SEQUENCE: 76

Trp Tyr Gln Gln Lys Pro Gly Thr Ser Pro Lys Arg Trp Ile Tyr
1 5 10 15

<210> SEQ ID NO 77
<211> LENGTH: 15
<212> TYPE: PRT
<213> ORGANISM: Artificial Sequence
<220> FEATURE:
<223> OTHER INFORMATION: VL FR2

<400> SEQUENCE: 77

Trp Leu Gln Gln Lys Pro Asp Gly Thr Ile Lys Arg Leu Ile Tyr
1 5 10 15

<210> SEQ ID NO 78
<211> LENGTH: 15
<212> TYPE: PRT
<213> ORGANISM: Artificial Sequence
<220> FEATURE:
<223> OTHER INFORMATION: VL FR2

<400> SEQUENCE: 78

Trp Tyr Leu Gln Lys Pro Gly Gln Ser Pro Lys Leu Leu Ile Tyr
1               5                   10                  15

<210> SEQ ID NO 79
<211> LENGTH: 15
<212> TYPE: PRT
<213> ORGANISM: Artificial Sequence
<220> FEATURE:
<223> OTHER INFORMATION: VL FR2

<400> SEQUENCE: 79

Trp Phe Gln Gln Lys Pro Gly Thr Ser Pro Lys Leu Trp Ile Tyr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: VL FR2

<400> SEQUENCE: 80

Trp Asn Gln Gln Lys Pro Gly Gln Pro Pro Arg Leu Leu Ile Tyr
1               5                   10                  15

<210> SEQ ID NO 81
<211> LENGTH: 32
<212> TYPE: PRT
<213> ORGANISM: Artificial Sequence
<220> FEATURE:
<223> OTHER INFORMATION: VH FR3

<400> SEQUENCE: 81

Lys Ala Thr Leu Thr Val Asp Lys Ser Ser Ser Thr Ala Tyr Met Gln
1               5                   10                  15

Leu Ser Ser Leu Thr Ser Glu Asp Ser Ala Val Tyr Tyr Cys Ala Arg
            20                  25                  30

<210> SEQ ID NO 82
<211> LENGTH: 30
<212> TYPE: PRT
<213> ORGANISM: Artificial Sequence
<220> FEATURE:
<223> OTHER INFORMATION: VH FR3

<400> SEQUENCE: 82

Lys Ala Thr Leu Thr Val Asp Lys Ser Ser Ser Thr Ala Tyr Met Gln
1               5                   10                  15

Leu Ser Ser Leu Thr Ser Glu Asp Ser Ala Val Tyr Tyr Cys
            20                  25                  30

<210> SEQ ID NO 83
<211> LENGTH: 32
<212> TYPE: PRT
<213> ORGANISM: Artificial Sequence
<220> FEATURE:
<223> OTHER INFORMATION: VH FR3

<400> SEQUENCE: 83

Lys Ala Thr Leu Thr Val Asp Lys Ser Ser Ser Thr Ala Tyr Met Gln
1               5                   10                  15

Leu Ser Ser Leu Thr Ser Glu Asp Ser Ala Val Tyr Tyr Cys Ala Asn
            20                  25                  30

<210> SEQ ID NO 84
<211> LENGTH: 32
<212> TYPE: PRT
<213> ORGANISM: Artificial Sequence
<220> FEATURE:
<223> OTHER INFORMATION: VL FR3

<400> SEQUENCE: 84

Gly Val Pro Asp Arg Phe Thr Gly Ser Gly Ser Gly Thr Asp Phe Thr
1 5 10 15

Leu Thr Ile Ser Asn Val Gln Ser Glu Asp Leu Ala Glu Tyr Phe Cys
20 25 30

<210> SEQ ID NO 85
<211> LENGTH: 32
<212> TYPE: PRT
<213> ORGANISM: Artificial Sequence
<220> FEATURE:
<223> OTHER INFORMATION: VL FR3

<400> SEQUENCE: 85

Gly Val Pro Ala Arg Phe Ser Gly Ser Gly Ser Gly Thr Ser Tyr Ser
1 5 10 15

Leu Thr Ile Ser Ser Met Glu Ala Glu Asp Ala Ala Thr Tyr Tyr Cys
20 25 30

<210> SEQ ID NO 86
<211> LENGTH: 32
<212> TYPE: PRT
<213> ORGANISM: Artificial Sequence
<220> FEATURE:
<223> OTHER INFORMATION: VL FR3

<400> SEQUENCE: 86

Gly Val Pro Lys Arg Phe Ser Gly Ser Arg Ser Gly Ser Asp Tyr Ser
1 5 10 15

Leu Thr Ile Ser Ser Leu Glu Ser Glu Asp Phe Ala Asp Tyr Tyr Cys
20 25 30

<210> SEQ ID NO 87
<211> LENGTH: 32
<212> TYPE: PRT
<213> ORGANISM: Artificial Sequence
<220> FEATURE:
<223> OTHER INFORMATION: VL FR3

<400> SEQUENCE: 87

Gly Val Pro Asp Arg Phe Ser Gly Ser Gly Ser Gly Thr Asp Phe Thr
1 5 10 15

Leu Lys Ile Ser Arg Val Glu Ala Glu Asp Leu Gly Val Tyr Tyr Cys
20 25 30

<210> SEQ ID NO 88
<211> LENGTH: 32
<212> TYPE: PRT
<213> ORGANISM: Artificial Sequence
<220> FEATURE:
<223> OTHER INFORMATION: VL FR3

<400> SEQUENCE: 88

Gly Val Pro Ala Arg Phe Ser Gly Ser Gly Ser Gly Thr Ser Tyr Ser
1 5 10 15

Leu Thr Ile Ser Arg Met Glu Ala Glu Asp Ala Ala Thr Tyr Tyr Cys
            20                  25                  30

<210> SEQ ID NO 89
<211> LENGTH: 32
<212> TYPE: PRT
<213> ORGANISM: Artificial Sequence
<220> FEATURE:
<223> OTHER INFORMATION: VL FR3

<400> SEQUENCE: 89

Gly Val Pro Ala Arg Phe Ser Gly Ser Gly Ser Gly Thr Asp Phe Thr
1               5                   10                  15

Leu Asn Ile His Pro Val Glu Glu Glu Asp Ala Ala Thr Tyr Tyr Cys
            20                  25                  30

<210> SEQ ID NO 90
<211> LENGTH: 11
<212> TYPE: PRT
<213> ORGANISM: Artificial Sequence
<220> FEATURE:
<223> OTHER INFORMATION: VH FR4

<400> SEQUENCE: 90

Trp Gly Gln Gly Thr Thr Leu Thr Val Ser Ser
1               5                   10

<210> SEQ ID NO 91
<211> LENGTH: 12
<212> TYPE: PRT
<213> ORGANISM: Artificial Sequence
<220> FEATURE:
<223> OTHER INFORMATION: VH FR4

<400> SEQUENCE: 91

Trp Gly Gln Gly Thr Leu Val Thr Val Ser Ala Ala
1               5                   10

<210> SEQ ID NO 92
<211> LENGTH: 10
<212> TYPE: PRT
<213> ORGANISM: Artificial Sequence
<220> FEATURE:
<223> OTHER INFORMATION: VH FR4

<400> SEQUENCE: 92

Trp Gly Gln Gly Thr Ser Val Thr Val Ser
1               5                   10

<210> SEQ ID NO 93
<211> LENGTH: 10
<212> TYPE: PRT
<213> ORGANISM: Artificial Sequence
<220> FEATURE:
<223> OTHER INFORMATION: VH FR4

<400> SEQUENCE: 93

Trp Gly Thr Gly Thr Thr Val Thr Val Ser
1               5                   10

<210> SEQ ID NO 94
<211> LENGTH: 11
<212> TYPE: PRT
<213> ORGANISM: Artificial Sequence
<220> FEATURE:
<223> OTHER INFORMATION: VL FR4

<400> SEQUENCE: 94

Phe Gly Gly Gly Thr Lys Leu Glu Ile Lys Arg
1 5 10

<210> SEQ ID NO 95
<211> LENGTH: 10
<212> TYPE: PRT
<213> ORGANISM: Artificial Sequence
<220> FEATURE:
<223> OTHER INFORMATION: VL FR4

<400> SEQUENCE: 95

Phe Gly Ala Gly Thr Lys Leu Glu Leu Lys
1 5 10

<210> SEQ ID NO 96
<211> LENGTH: 9
<212> TYPE: PRT
<213> ORGANISM: Artificial Sequence
<220> FEATURE:
<223> OTHER INFORMATION: VL FR4

<400> SEQUENCE: 96

Phe Gly Gly Gly Thr Lys Leu Glu Ile
1 5

<210> SEQ ID NO 97
<211> LENGTH: 14
<212> TYPE: PRT
<213> ORGANISM: Artificial Sequence
<220> FEATURE:
<223> OTHER INFORMATION: VL FR4

<400> SEQUENCE: 97

Phe Gly Gly Gly Thr Lys Leu Glu Ile Lys Arg Ala Asp Ala
1 5 10

<210> SEQ ID NO 98
<211> LENGTH: 13
<212> TYPE: PRT
<213> ORGANISM: Artificial Sequence
<220> FEATURE:
<223> OTHER INFORMATION: VL FR4

<400> SEQUENCE: 98

Phe Gly Gly Gly Thr Lys Leu Glu Ile Lys Arg Ala Asp
1 5 10

<210> SEQ ID NO 99
<211> LENGTH: 9
<212> TYPE: PRT
<213> ORGANISM: Artificial Sequence
<220> FEATURE:
<223> OTHER INFORMATION: VL FR4

<400> SEQUENCE: 99

Phe Gly Arg Gly Asp Gln Ser Trp Lys
1 5

<210> SEQ ID NO 100
<211> LENGTH: 19
<212> TYPE: PRT
<213> ORGANISM: Artificial Sequence
<220> FEATURE:
<223> OTHER INFORMATION: Leader sequence

<400> SEQUENCE: 100

Met Gly Trp Ser Tyr Ile Ile Leu Phe Leu Val Ala Thr Ala Thr Gly
1 5 10 15

Val His Ser

<210> SEQ ID NO 101
<211> LENGTH: 19
<212> TYPE: PRT
<213> ORGANISM: Artificial Sequence
<220> FEATURE:
<223> OTHER INFORMATION: Leader sequence

<400> SEQUENCE: 101

Met Gly Trp Ser Cys Ile Met Leu Phe Leu Val Ala Thr Ala Thr Gly
1 5 10 15

Val His Ser

<210> SEQ ID NO 102
<211> LENGTH: 19
<212> TYPE: PRT
<213> ORGANISM: Artificial Sequence
<220> FEATURE:
<223> OTHER INFORMATION: Leader sequence

<400> SEQUENCE: 102

Met Gly Trp Ser Cys Ile Met Phe Phe Leu Val Ala Thr Ala Thr Gly
1 5 10 15

Val His Ser

<210> SEQ ID NO 103
<211> LENGTH: 19
<212> TYPE: PRT
<213> ORGANISM: Artificial Sequence
<220> FEATURE:
<223> OTHER INFORMATION: Leader sequence

<400> SEQUENCE: 103

Met Glu Trp Ser Trp Val Ile Leu Ile Leu Val Ala Ala Ala Thr Gly
1 5 10 15

Val His Ser

<210> SEQ ID NO 104
<211> LENGTH: 20
<212> TYPE: PRT
<213> ORGANISM: Artificial Sequence
<220> FEATURE:
<223> OTHER INFORMATION: Leader sequence

<400> SEQUENCE: 104

Met Lys Thr Gln Thr Gln Val Phe Val Tyr Met Leu Leu Trp Leu Ser
1 5 10 15

Gly Val Asp Gly
20

<210> SEQ ID NO 105
<211> LENGTH: 22
<212> TYPE: PRT
<213> ORGANISM: Artificial Sequence
<220> FEATURE:
<223> OTHER INFORMATION: Leader sequence

<400> SEQUENCE: 105

Met Asp Leu Gln Val Gln Ile Phe Ser Phe Leu Leu Ile Ser Ala Ser
1 5 10 15

Val Ile Leu Ser Arg Gly
20

<210> SEQ ID NO 106
<211> LENGTH: 15
<212> TYPE: PRT
<213> ORGANISM: Artificial Sequence
<220> FEATURE:
<223> OTHER INFORMATION: Leader sequence

<400> SEQUENCE: 106

Met Val Leu Ile Ser Leu Leu Phe Trp Phe Pro Gly Thr Arg Cys
1 5 10 15

<210> SEQ ID NO 107
<211> LENGTH: 19
<212> TYPE: PRT
<213> ORGANISM: Artificial Sequence
<220> FEATURE:
<223> OTHER INFORMATION: Leader sequence

<400> SEQUENCE: 107

Met Lys Met Pro Val Arg Leu Leu Val Leu Met Phe Trp Ile Pro Ala
1 5 10 15

Ser Ser Ser

<210> SEQ ID NO 108
<211> LENGTH: 22
<212> TYPE: PRT
<213> ORGANISM: Artificial Sequence
<220> FEATURE:
<223> OTHER INFORMATION: Leader sequence

<400> SEQUENCE: 108

Met Asp Phe Gln Val Gln Ile Phe Ser Phe Leu Leu Ile Ser Ala Ser
1 5 10 15

Val Ile Met Ser Arg Gly
20

<210> SEQ ID NO 109
<211> LENGTH: 20
<212> TYPE: PRT
<213> ORGANISM: Artificial Sequence
<220> FEATURE:
<223> OTHER INFORMATION: Leader sequence

<400> SEQUENCE: 109

Met Glu Thr Asp Thr Leu Leu Leu Trp Val Leu Leu Leu Trp Val Pro
1 5 10 15

Gly Ser Thr Gly
20

<210> SEQ ID NO 110
<211> LENGTH: 115
<212> TYPE: PRT
<213> ORGANISM: Artificial Sequence
<220> FEATURE:
<223> OTHER INFORMATION: VH chain
<220> FEATURE:
<221> NAME/KEY: MISC_FEATURE
<222> LOCATION: (1)..(25)

<223> OTHER INFORMATION: FR1
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
<222> LOCATION: (105)..(115)
<223> OTHER INFORMATION: FR4

<400> SEQUENCE: 110

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Tyr Phe Asp Tyr Trp Gly Gln Gly Thr Thr Leu Thr
            100                 105                 110

Val Ser Ser
        115
```

<210> SEQ ID NO 111
<211> LENGTH: 116
<212> TYPE: PRT
<213> ORGANISM: Artificial Sequence
<220> FEATURE:
<223> OTHER INFORMATION: VH chain
<220> FEATURE:
<221> NAME/KEY: MISC_FEATURE
<222> LOCATION: (1)..(25)
<223> OTHER INFORMATION: FR1
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(96)
<223> OTHER INFORMATION: FR3

<220> FEATURE:
<221> NAME/KEY: MISC_FEATURE
<222> LOCATION: (97)..(105)
<223> OTHER INFORMATION: CDR3
<220> FEATURE:
<221> NAME/KEY: MISC_FEATURE
<222> LOCATION: (106)..(116)
<223> OTHER INFORMATION: FR4

<400> SEQUENCE: 111

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Ser Arg Gln Leu Asp Tyr Trp Gly Gln Gly Thr Thr Leu
            100                 105                 110

Thr Val Ser Ser
        115
```

<210> SEQ ID NO 112
<211> LENGTH: 115
<212> TYPE: PRT
<213> ORGANISM: Artificial Sequence
<220> FEATURE:
<223> OTHER INFORMATION: VH chain
<220> FEATURE:
<221> NAME/KEY: MISC_FEATURE
<222> LOCATION: (1)..(25)
<223> OTHER INFORMATION: FR1
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
<222> LOCATION: (105)..(115)
<223> OTHER INFORMATION: FR4

<400> SEQUENCE: 112

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Asn Tyr
            20                  25                  30
```

```
Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Arg Gly Asp Gly Asp Tyr Trp Gly Gln Gly Thr Thr Leu Thr
            100                 105                 110

Val Ser Ser
        115


<210> SEQ ID NO 113
<211> LENGTH: 120
<212> TYPE: PRT
<213> ORGANISM: Artificial Sequence
<220> FEATURE:
<223> OTHER INFORMATION: VH chain
<220> FEATURE:
<221> NAME/KEY: MISC_FEATURE
<222> LOCATION: (1)..(25)
<223> OTHER INFORMATION: FR1
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(96)
<223> OTHER INFORMATION: FR3
<220> FEATURE:
<221> NAME/KEY: MISC_FEATURE
<222> LOCATION: (97)..(108)
<223> OTHER INFORMATION: CDR3
<220> FEATURE:
<221> NAME/KEY: MISC_FEATURE
<222> LOCATION: (109)..(120)
<223> OTHER INFORMATION: FR4

<400> SEQUENCE: 113

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Trp Ile Thr Trp Val Lys Gln Arg Pro Gly Gln Gly Leu Glu Trp Ile
        35                  40                  45

Gly Asp Ile Tyr Pro Gly Ser Gly Ser Thr Asn Tyr Asn Glu Lys Phe
    50                  55                  60

Lys Ser Lys Ala Thr Leu Thr Val Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Gly Gly Thr Arg Phe Ser Pro Phe Ala Tyr Trp Gly Gln Gly
            100                 105                 110

Thr Leu Val Thr Val Ser Ala Ala
        115                 120
```

<210> SEQ ID NO 114
<211> LENGTH: 119
<212> TYPE: PRT
<213> ORGANISM: Artificial Sequence
<220> FEATURE:
<223> OTHER INFORMATION: VH chain
<220> FEATURE:
<221> NAME/KEY: MISC_FEATURE
<222> LOCATION: (1)..(25)
<223> OTHER INFORMATION: FR1
<220> FEATURE:
<221> NAME/KEY: MISC_FEATURE
<222> LOCATION: (26)..(35)
<223> OTHER INFORMATION: CDR1
<220> FEATURE:
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(109)
<223> OTHER INFORMATION: CDR3
<220> FEATURE:
<221> NAME/KEY: MISC_FEATURE
<222> LOCATION: (110)..(119)
<223> OTHER INFORMATION: FR4

<400> SEQUENCE: 114

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Tyr Gly Ser Ser Tyr Ala Met Asp Tyr Trp Gly Gln
            100                 105                 110

Gly Thr Ser Val Thr Val Ser
        115
```

<210> SEQ ID NO 115
<211> LENGTH: 114
<212> TYPE: PRT
<213> ORGANISM: Artificial Sequence
<220> FEATURE:
<223> OTHER INFORMATION: VH chain
<220> FEATURE:
<221> NAME/KEY: MISC_FEATURE
<222> LOCATION: (1)..(25)
<223> OTHER INFORMATION: FR1
<220> FEATURE:
<221> NAME/KEY: MISC_FEATURE
<222> LOCATION: (26)..(35)
<223> OTHER INFORMATION: CDR1
<220> FEATURE:

```
<221> NAME/KEY: MISC_FEATURE
<222> LOCATION: (36)..(49)
<223> OTHER INFORMATION: FR2
<220> FEATURE:
<221> NAME/KEY: MISC_FEATURE
<222> LOCATION: (50)..(66)
<223> OTHER INFORMATION: CDR2
<220> FEATURE:
<221> NAME/KEY: MISC_FEATURE
<222> LOCATION: (67)..(98)
<223> OTHER INFORMATION: FR3
<220> FEATURE:
<221> NAME/KEY: MISC_FEATURE
<222> LOCATION: (99)..(104)
<223> OTHER INFORMATION: CDR3
<220> FEATURE:
<221> NAME/KEY: MISC_FEATURE
<222> LOCATION: (105)..(114)
<223> OTHER INFORMATION: FR4

<400> SEQUENCE: 115

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Met Ile His Pro Asn Ser Gly Ser Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Asn Tyr Tyr Gly Thr Asn Val Trp Gly Thr Gly Thr Thr Val Thr
            100                 105                 110

Val Ser


<210> SEQ ID NO 116
<211> LENGTH: 108
<212> TYPE: PRT
<213> ORGANISM: Artificial Sequence
<220> FEATURE:
<223> OTHER INFORMATION: VL chain
<220> FEATURE:
<221> NAME/KEY: MISC_FEATURE
<222> LOCATION: (1)..(23)
<223> OTHER INFORMATION: FR1
<220> FEATURE:
<221> NAME/KEY: MISC_FEATURE
<222> LOCATION: (24)..(34)
<223> OTHER INFORMATION: CDR1
<220> FEATURE:
<221> NAME/KEY: MISC_FEATURE
<222> LOCATION: (35)..(49)
<223> OTHER INFORMATION: FR2
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (57)..(88)
<223> OTHER INFORMATION: FR3
<220> FEATURE:
<221> NAME/KEY: MISC_FEATURE
<222> LOCATION: (89)..(97)
<223> OTHER INFORMATION: CDR3
<220> FEATURE:
<221> NAME/KEY: MISC_FEATURE
<222> LOCATION: (98)..(108)
```

<223> OTHER INFORMATION: FR4

<400> SEQUENCE: 116

Asp Ile Val Met Thr Gln Ser Gln Lys Phe Met Ser Thr Ser Val Gly
1 5 10 15

Asp Arg Val Ser Val Thr Cys Lys Ala Ser Gln Asn Val Gly Thr Asn
20 25 30

Val Ala Trp Tyr Gln Gln Lys Pro Gly Gln Ser Pro Lys Ala Leu Ile
35 40 45

Tyr Ser Ala Ser Tyr Arg Tyr Ser Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Glu Tyr Phe Cys Gln Gln Tyr Asn Ser Tyr Pro Tyr
85 90 95

Thr Phe Gly Gly Gly Thr Lys Leu Glu Ile Lys Arg
100 105

<210> SEQ ID NO 117
<211> LENGTH: 106
<212> TYPE: PRT
<213> ORGANISM: Artificial Sequence
<220> FEATURE:
<223> OTHER INFORMATION: VL chain
<220> FEATURE:
<221> NAME/KEY: MISC_FEATURE
<222> LOCATION: (1)..(23)
<223> OTHER INFORMATION: FR1
<220> FEATURE:
<221> NAME/KEY: MISC_FEATURE
<222> LOCATION: (24)..(33)
<223> OTHER INFORMATION: CDR1
<220> FEATURE:
<221> NAME/KEY: MISC_FEATURE
<222> LOCATION: (34)..(48)
<223> OTHER INFORMATION: FR2
<220> FEATURE:
<221> NAME/KEY: MISC_FEATURE
<222> LOCATION: (49)..(55)
<223> OTHER INFORMATION: CDR2
<220> FEATURE:
<221> NAME/KEY: MISC_FEATURE
<222> LOCATION: (56)..(87)
<223> OTHER INFORMATION: FR3
<220> FEATURE:
<221> NAME/KEY: MISC_FEATURE
<222> LOCATION: (88)..(96)
<223> OTHER INFORMATION: CDR3
<220> FEATURE:
<221> NAME/KEY: MISC_FEATURE
<222> LOCATION: (97)..(106)
<223> OTHER INFORMATION: FR4

<400> SEQUENCE: 117

Gln Ile Val Leu Thr Gln Ser Pro Ala Ile Met Ser Ala Ser Pro Gly
1 5 10 15

Glu Lys Val Thr Met Thr Cys Ser Ala Ser Ser Ser Ile Ser Tyr Met
20 25 30

His Trp Tyr Gln Gln Lys Pro Gly Thr Ser Pro Lys Arg Trp Ile Tyr
35 40 45

Asp Thr Ser Lys Leu Ala Ser Gly Val Pro Ala Arg Phe Ser Gly Ser
50 55 60

Gly Ser Gly Thr Ser Tyr Ser Leu Thr Ile Ser Ser Met Glu Ala Glu
65 70 75 80

```
Asp Ala Ala Thr Tyr Tyr Cys His Gln Arg Ser Ser Tyr Pro Leu Thr
                85                  90                  95

Phe Gly Ala Gly Thr Lys Leu Glu Leu Lys
            100                 105


<210> SEQ ID NO 118
<211> LENGTH: 106
<212> TYPE: PRT
<213> ORGANISM: Artificial Sequence
<220> FEATURE:
<223> OTHER INFORMATION: VL chain
<220> FEATURE:
<221> NAME/KEY: MISC_FEATURE
<222> LOCATION: (1)..(23)
<223> OTHER INFORMATION: FR1
<220> FEATURE:
<221> NAME/KEY: MISC_FEATURE
<222> LOCATION: (24)..(34)
<223> OTHER INFORMATION: CDR1
<220> FEATURE:
<221> NAME/KEY: MISC_FEATURE
<222> LOCATION: (35)..(49)
<223> OTHER INFORMATION: FR2
<220> FEATURE:
<221> NAME/KEY: MISC_FEATURE
<222> LOCATION: (50)..(56)
<223> OTHER INFORMATION: CDR2
<220> FEATURE:
<221> NAME/KEY: MISC_FEATURE
<222> LOCATION: (57)..(88)
<223> OTHER INFORMATION: FR3
<220> FEATURE:
<221> NAME/KEY: MISC_FEATURE
<222> LOCATION: (89)..(97)
<223> OTHER INFORMATION: CDR3
<220> FEATURE:
<221> NAME/KEY: MISC_FEATURE
<222> LOCATION: (98)..(106)
<223> OTHER INFORMATION: FR4

<400> SEQUENCE: 118

Asp Ile Gln Met Thr Arg His Pro Ser Ser Leu Ser Ala Ser Met Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
        35                  40                  45

Tyr Ala Ala Ser Thr Leu Asp Ser Gly Val Pro Lys Arg Phe Ser Gly
    50                  55                  60

Ser Arg Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Ala Ser Tyr Pro Tyr
                85                  90                  95

Thr Phe Gly Gly Gly Thr Lys Leu Glu Ile
            100                 105


<210> SEQ ID NO 119
<211> LENGTH: 116
<212> TYPE: PRT
<213> ORGANISM: Artificial Sequence
<220> FEATURE:
<223> OTHER INFORMATION: VL chain
<220> FEATURE:
<221> NAME/KEY: MISC_FEATURE
<222> LOCATION: (1)..(23)
<223> OTHER INFORMATION: FR1
<220> FEATURE:
<221> NAME/KEY: MISC_FEATURE
```

<222> LOCATION: (24)..(39)
<223> OTHER INFORMATION: CDR1
<220> FEATURE:
<221> NAME/KEY: MISC_FEATURE
<222> LOCATION: (40)..(54)
<223> OTHER INFORMATION: FR2
<220> FEATURE:
<221> NAME/KEY: MISC_FEATURE
<222> LOCATION: (55)..(61)
<223> OTHER INFORMATION: CDR2
<220> FEATURE:
<221> NAME/KEY: MISC_FEATURE
<222> LOCATION: (62)..(93)
<223> OTHER INFORMATION: FR3
<220> FEATURE:
<221> NAME/KEY: MISC_FEATURE
<222> LOCATION: (94)..(102)
<223> OTHER INFORMATION: CDR3
<220> FEATURE:
<221> NAME/KEY: MISC_FEATURE
<222> LOCATION: (103)..(116)
<223> OTHER INFORMATION: FR4

<400> SEQUENCE: 119

```
Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Trp Thr Phe Gly Gly Gly Thr Lys Leu Glu Ile Lys
            100                 105                 110

Arg Ala Asp Ala
        115
```

<210> SEQ ID NO 120
<211> LENGTH: 109
<212> TYPE: PRT
<213> ORGANISM: Artificial Sequence
<220> FEATURE:
<223> OTHER INFORMATION: VL chain
<220> FEATURE:
<221> NAME/KEY: MISC_FEATURE
<222> LOCATION: (1)..(23)
<223> OTHER INFORMATION: FR1
<220> FEATURE:
<221> NAME/KEY: MISC_FEATURE
<222> LOCATION: (24)..(33)
<223> OTHER INFORMATION: CDR1
<220> FEATURE:
<221> NAME/KEY: MISC_FEATURE
<222> LOCATION: (34)..(48)
<223> OTHER INFORMATION: FR2
<220> FEATURE:
<221> NAME/KEY: MISC_FEATURE
<222> LOCATION: (49)..(55)
<223> OTHER INFORMATION: CDR2
<220> FEATURE:
<221> NAME/KEY: MISC_FEATURE
<222> LOCATION: (56)..(87)
<223> OTHER INFORMATION: FR3
<220> FEATURE:
<221> NAME/KEY: MISC_FEATURE
<222> LOCATION: (88)..(96)

```
<223> OTHER INFORMATION: CDR3
<220> FEATURE:
<221> NAME/KEY: MISC_FEATURE
<222> LOCATION: (97)..(109)
<223> OTHER INFORMATION: FR4

<400> SEQUENCE: 120

Gln Ile Val Leu Thr Gln Ser Pro Ala Ile Met Ser Ala Ser Pro Gly
1               5                   10                  15

Glu Lys Val Thr Ile Thr Cys Ser Ala Ser Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Tyr Thr
                85                  90                  95

Phe Gly Gly Gly Thr Lys Leu Glu Ile Lys Arg Ala Asp
            100                 105


<210> SEQ ID NO 121
<211> LENGTH: 109
<212> TYPE: PRT
<213> ORGANISM: Artificial Sequence
<220> FEATURE:
<223> OTHER INFORMATION: VL chain
<220> FEATURE:
<221> NAME/KEY: MISC_FEATURE
<222> LOCATION: (1)..(26)
<223> OTHER INFORMATION: FR1
<220> FEATURE:
<221> NAME/KEY: MISC_FEATURE
<222> LOCATION: (27)..(38)
<223> OTHER INFORMATION: CDR1
<220> FEATURE:
<221> NAME/KEY: MISC_FEATURE
<222> LOCATION: (39)..(53)
<223> OTHER INFORMATION: FR2
<220> FEATURE:
<221> NAME/KEY: MISC_FEATURE
<222> LOCATION: (54)..(60)
<223> OTHER INFORMATION: CDR2
<220> FEATURE:
<221> NAME/KEY: MISC_FEATURE
<222> LOCATION: (61)..(92)
<223> OTHER INFORMATION: FR3
<220> FEATURE:
<221> NAME/KEY: MISC_FEATURE
<222> LOCATION: (93)..(100)
<223> OTHER INFORMATION: CDR3
<220> FEATURE:
<221> NAME/KEY: MISC_FEATURE
<222> LOCATION: (101)..(109)
<223> OTHER INFORMATION: FR4

<400> SEQUENCE: 121

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60
```

-continued

```
Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Ala Tyr Thr Phe Gly Arg Gly Asp Gln Ser Trp Lys
            100                 105
```